US008123686B2

(12) United States Patent
Fennell et al.

(10) Patent No.: US 8,123,686 B2
(45) Date of Patent: Feb. 28, 2012

(54) METHOD AND APPARATUS FOR PROVIDING ROLLING DATA IN COMMUNICATION SYSTEMS

(75) Inventors: Martin J. Fennell, Concord, CA (US); Mark K. Sloan, Redwood City, CA (US)

(73) Assignee: Abbott Diabetes Care Inc., Alameda, CA (US)

( * ) Notice: Subject to any disclaimer, the term of this patent is extended or adjusted under 35 U.S.C. 154(b) by 0 days.

(21) Appl. No.: 11/681,133

(22) Filed: Mar. 1, 2007

(65) Prior Publication Data
US 2008/0214900 A1 Sep. 4, 2008

(51) Int. Cl.
A61B 5/05 (2006.01)
G06F 15/16 (2006.01)
H04L 12/43 (2006.01)
H04J 3/00 (2006.01)
H04W 4/00 (2009.01)

(52) U.S. Cl. ........ 600/365; 709/230; 709/231; 709/232; 709/200; 709/203; 709/217; 370/458; 370/314; 370/345

(58) Field of Classification Search .......... 600/300, 600/322, 345–366, 309; 435/14; 709/200, 709/203, 217, 230–232, 236; 370/314, 336, 370/345, 913, 395.21, 395.42, 395.43, 389, 370/392, 401, 458
See application file for complete search history.

(56) References Cited

U.S. PATENT DOCUMENTS

| | | | |
|---|---|---|---|
| 2,755,036 A | 7/1956 | Mikko | |
| 3,260,656 A | 7/1966 | Ross, Jr. | |
| 3,304,413 A | 2/1967 | Lehmann et al. | |
| 3,581,062 A | 5/1971 | Aston | |
| 3,651,318 A | 3/1972 | Czekajewski | |
| 3,653,841 A | 4/1972 | Klein | |
| 3,698,386 A | 10/1972 | Fried | |
| 3,719,564 A | 3/1973 | Lilly, Jr. et al. | |
| 3,768,014 A | 10/1973 | Smith et al. | |
| 3,776,832 A | 12/1973 | Oswin et al. | |
| 3,837,339 A | 9/1974 | Aisenberg et al. | |
| 3,919,051 A | 11/1975 | Koch et al. | |
| 3,926,760 A | 12/1975 | Allen et al. | |
| 3,949,388 A | 4/1976 | Fuller | |
| 3,972,320 A | 8/1976 | Kalman | |
| 3,979,274 A | 9/1976 | Newman | |
| 4,003,379 A | 1/1977 | Ellinwood, Jr. | |
| 4,008,717 A | 2/1977 | Kowarski | |
| 4,016,866 A | 4/1977 | Lawton | |
| 4,021,718 A * | 5/1977 | Konrad | 340/636.16 |

(Continued)

FOREIGN PATENT DOCUMENTS

CA 2143172 7/2005

(Continued)

OTHER PUBLICATIONS

Abruna, H. D., et al., "Rectifying Interfaces Using Two-Layer Films of Electrochemically Polymerized Vinylpyridine and Vinylbipyridine Complexes of Ruthenium and Iron on Electrodes", *Journal of the American Chemical Society*, vol. 103, No. 1, 1981, pp. 1-5.

(Continued)

*Primary Examiner* — Navin Natnithithadha
(74) *Attorney, Agent, or Firm* — Jackson & Co., LLP

(57) ABSTRACT

Methods and systems for providing data communication in medical systems are disclosed.

29 Claims, 5 Drawing Sheets

U.S. PATENT DOCUMENTS

| | | |
|---|---|---|
| 4,036,749 A | 7/1977 | Anderson |
| 4,055,175 A | 10/1977 | Clemens et al. |
| 4,059,406 A | 11/1977 | Fleet |
| 4,068,536 A | 1/1978 | Stackhouse |
| 4,076,596 A | 2/1978 | Connery et al. |
| 4,098,574 A | 7/1978 | Dappen |
| 4,100,048 A | 7/1978 | Pompei et al. |
| 4,129,128 A | 12/1978 | McFarlane |
| 4,151,845 A | 5/1979 | Clemens |
| 4,154,231 A | 5/1979 | Russell |
| 4,168,205 A | 9/1979 | Danniger et al. |
| 4,172,770 A | 10/1979 | Semersky et al. |
| 4,178,916 A | 12/1979 | McNamara |
| 4,193,026 A * | 3/1980 | Finger et al. ............... 324/428 |
| 4,206,755 A | 6/1980 | Klein |
| 4,224,125 A | 9/1980 | Nakamura et al. |
| 4,240,438 A | 12/1980 | Updike et al. |
| 4,240,889 A | 12/1980 | Yoda et al. |
| 4,245,634 A | 1/1981 | Albisser et al. |
| 4,247,297 A | 1/1981 | Berti et al. |
| 4,271,449 A | 6/1981 | Grogan |
| 4,318,784 A | 3/1982 | Higgins et al. |
| 4,327,725 A | 5/1982 | Cortese et al. |
| 4,331,869 A | 5/1982 | Rollo |
| 4,340,458 A | 7/1982 | Lerner et al. |
| 4,344,438 A | 8/1982 | Schultz |
| 4,349,728 A | 9/1982 | Phillips et al. |
| 4,352,960 A | 10/1982 | Dormer et al. |
| 4,356,074 A | 10/1982 | Johnson |
| 4,365,637 A | 12/1982 | Johnson |
| 4,366,033 A | 12/1982 | Richter et al. |
| 4,375,399 A | 3/1983 | Havas et al. |
| 4,384,586 A | 5/1983 | Christiansen |
| 4,390,621 A | 6/1983 | Bauer |
| 4,392,933 A | 7/1983 | Nakamura et al. |
| 4,401,122 A | 8/1983 | Clark, Jr. |
| 4,404,066 A | 9/1983 | Johnson |
| 4,407,959 A | 10/1983 | Tsuji et al. |
| 4,417,588 A | 11/1983 | Houghton et al. |
| 4,418,148 A | 11/1983 | Oberhardt |
| 4,420,564 A | 12/1983 | Tsuji et al. |
| 4,425,920 A | 1/1984 | Bourland et al. |
| 4,427,004 A | 1/1984 | Miller et al. |
| 4,427,770 A | 1/1984 | Chen et al. |
| 4,431,004 A | 2/1984 | Bessman et al. |
| 4,436,094 A | 3/1984 | Cerami |
| 4,440,175 A | 4/1984 | Wilkins |
| 4,441,968 A | 4/1984 | Emmer et al. |
| 4,444,892 A | 4/1984 | Malmros |
| 4,450,842 A | 5/1984 | Zick et al. |
| 4,458,686 A | 7/1984 | Clark, Jr. |
| 4,461,691 A | 7/1984 | Frank |
| 4,467,811 A | 8/1984 | Clark, Jr. |
| 4,469,110 A | 9/1984 | Slama |
| 4,477,314 A | 10/1984 | Richter et al. |
| 4,478,976 A | 10/1984 | Goertz et al. |
| 4,483,924 A | 11/1984 | Tsuji et al. |
| 4,484,987 A | 11/1984 | Gough |
| 4,494,950 A | 1/1985 | Fischell |
| 4,509,531 A | 4/1985 | Ward |
| 4,512,348 A | 4/1985 | Uchigaki et al. |
| 4,522,690 A | 6/1985 | Venkatsetty |
| 4,524,114 A | 6/1985 | Samuels et al. |
| 4,526,661 A | 7/1985 | Steckhan et al. |
| 4,527,240 A | 7/1985 | Kvitash |
| 4,534,356 A | 8/1985 | Papadakis |
| 4,538,616 A | 9/1985 | Rogoff |
| 4,543,955 A | 10/1985 | Schroeppel |
| 4,545,382 A | 10/1985 | Higgins et al. |
| 4,552,840 A | 11/1985 | Riffer |
| 4,560,534 A | 12/1985 | Kung et al. |
| 4,569,589 A | 2/1986 | Neufeld |
| 4,571,292 A | 2/1986 | Liu et al. |
| 4,573,994 A | 3/1986 | Fischell et al. |
| 4,581,336 A | 4/1986 | Malloy et al. |
| 4,595,011 A | 6/1986 | Phillips |
| 4,595,479 A | 6/1986 | Kimura et al. |
| 4,601,707 A | 7/1986 | Albisser et al. |
| 4,619,754 A | 10/1986 | Niki et al. |
| 4,619,793 A | 10/1986 | Lee |
| 4,627,445 A | 12/1986 | Garcia et al. |
| 4,627,908 A | 12/1986 | Miller |
| 4,633,878 A | 1/1987 | Bombardien |
| 4,633,881 A | 1/1987 | Moore et al. |
| 4,637,403 A | 1/1987 | Garcia et al. |
| 4,648,408 A | 3/1987 | Hutcheson et al. |
| 4,650,547 A | 3/1987 | Gough |
| 4,653,513 A | 3/1987 | Dombrowski |
| 4,654,197 A | 3/1987 | Lilja et al. |
| 4,655,880 A | 4/1987 | Liu |
| 4,655,885 A | 4/1987 | Hill et al. |
| 4,658,463 A | 4/1987 | Sugita et al. |
| 4,671,288 A | 6/1987 | Gough |
| 4,674,652 A | 6/1987 | Aten et al. |
| 4,679,562 A | 7/1987 | Luksha |
| 4,680,268 A | 7/1987 | Clark, Jr. |
| 4,682,602 A | 7/1987 | Prohaska |
| 4,684,537 A | 8/1987 | Graetzel et al. |
| 4,685,463 A | 8/1987 | Williams |
| 4,685,903 A | 8/1987 | Cable et al. |
| 4,686,624 A | 8/1987 | Blum et al. |
| 4,703,756 A | 11/1987 | Gough et al. |
| 4,711,245 A | 12/1987 | Higgins et al. |
| 4,717,673 A | 1/1988 | Wrighton et al. |
| 4,721,601 A | 1/1988 | Wrighton et al. |
| 4,721,677 A | 1/1988 | Clark, Jr. |
| 4,726,378 A | 2/1988 | Kaplan |
| 4,726,716 A | 2/1988 | McGuire |
| 4,731,726 A | 3/1988 | Allen, III |
| 4,749,985 A | 6/1988 | Corsberg |
| 4,750,496 A | 6/1988 | Reinhart |
| 4,757,022 A | 7/1988 | Shults et al. |
| 4,758,323 A | 7/1988 | Davis et al. |
| 4,759,371 A | 7/1988 | Franetzki |
| 4,759,828 A | 7/1988 | Young et al. |
| 4,764,416 A | 8/1988 | Ueyama et al. |
| 4,776,944 A | 10/1988 | Janata et al. |
| 4,777,953 A | 10/1988 | Ash et al. |
| 4,779,618 A | 10/1988 | Mund et al. |
| 4,781,798 A | 11/1988 | Gough |
| 4,784,736 A | 11/1988 | Lonsdale et al. |
| 4,795,707 A | 1/1989 | Niiyama et al. |
| 4,796,634 A | 1/1989 | Huntsman et al. |
| 4,803,625 A | 2/1989 | Fu et al. |
| 4,805,624 A | 2/1989 | Yao et al. |
| 4,813,424 A | 3/1989 | Wilkins |
| 4,815,469 A | 3/1989 | Cohen et al. |
| 4,820,399 A | 4/1989 | Senda et al. |
| 4,822,337 A | 4/1989 | Newhouse et al. |
| 4,830,959 A | 5/1989 | McNeil et al. |
| 4,832,797 A | 5/1989 | Vadgama et al. |
| 4,835,372 A | 5/1989 | Gombrich et al. |
| RE32,947 E | 6/1989 | Dormer et al. |
| 4,837,049 A | 6/1989 | Byers et al. |
| 4,840,893 A | 6/1989 | Hill et al. |
| RE32,974 E | 7/1989 | Porat et al. |
| 4,844,076 A | 7/1989 | Lesho et al. |
| 4,845,035 A | 7/1989 | Fanta et al. |
| 4,848,351 A | 7/1989 | Finch |
| 4,854,322 A | 8/1989 | Ash et al. |
| 4,856,340 A | 8/1989 | Garrison |
| 4,857,713 A | 8/1989 | Brown |
| 4,858,617 A | 8/1989 | Sanders |
| 4,870,561 A | 9/1989 | Love et al. |
| 4,871,351 A | 10/1989 | Feingold |
| 4,871,440 A | 10/1989 | Nagata et al. |
| 4,874,499 A | 10/1989 | Smith et al. |
| 4,874,500 A | 10/1989 | Madou et al. |
| 4,890,620 A | 1/1990 | Gough |
| 4,890,621 A | 1/1990 | Hakky |
| 4,894,137 A | 1/1990 | Takizawa et al. |
| 4,897,162 A | 1/1990 | Lewandowski et al. |
| 4,897,173 A | 1/1990 | Nankai et al. |
| 4,899,839 A | 2/1990 | Dessertine et al. |
| 4,909,908 A | 3/1990 | Ross et al. |
| 4,911,794 A | 3/1990 | Parce et al. |
| 4,917,800 A | 4/1990 | Lonsdale et al. |

| | | |
|---|---|---|
| 4,919,141 A | 4/1990 | Zier et al. |
| 4,919,767 A | 4/1990 | Vadgama et al. |
| 4,920,969 A | 5/1990 | Suzuki |
| 4,920,977 A | 5/1990 | Haynes |
| 4,923,586 A | 5/1990 | Katayama et al. |
| 4,925,268 A | 5/1990 | Iyer et al. |
| 4,927,516 A | 5/1990 | Yamaguchi et al. |
| 4,931,795 A | 6/1990 | Gord |
| 4,934,369 A | 6/1990 | Maxwell |
| 4,935,105 A | 6/1990 | Churchouse |
| 4,935,345 A | 6/1990 | Guilbeau et al. |
| 4,936,956 A | 6/1990 | Wrighton |
| 4,938,860 A | 7/1990 | Wogoman |
| 4,942,127 A | 7/1990 | Wada et al. |
| 4,944,299 A | 7/1990 | Silvian |
| 4,945,045 A | 7/1990 | Forrest et al. |
| 4,950,378 A | 8/1990 | Nagara |
| 4,953,552 A | 9/1990 | DeMarzo |
| 4,954,129 A | 9/1990 | Giuliani et al. |
| 4,957,115 A | 9/1990 | Selker |
| 4,958,632 A | 9/1990 | Duggan |
| 4,968,400 A | 11/1990 | Shimomura et al. |
| 4,969,468 A | 11/1990 | Byers et al. |
| 4,970,145 A | 11/1990 | Bennetto et al. |
| 4,974,929 A | 12/1990 | Curry |
| 4,979,509 A | 12/1990 | Hakky |
| 4,986,271 A | 1/1991 | Wilkins |
| 4,990,845 A | 2/1991 | Gord |
| 4,991,582 A | 2/1991 | Byers et al. |
| 4,994,068 A | 2/1991 | Hufnagie |
| 4,994,167 A | 2/1991 | Shults et al. |
| 4,995,402 A | 2/1991 | Smith et al. |
| 5,000,180 A | 3/1991 | Kuypers et al. |
| 5,001,054 A | 3/1991 | Wagner |
| 5,002,054 A | 3/1991 | Ash et al. |
| 5,007,427 A | 4/1991 | Suzuki et al. |
| 5,016,172 A | 5/1991 | Dessertine |
| 5,016,201 A | 5/1991 | Bryan et al. |
| 5,019,974 A | 5/1991 | Beckers |
| 5,034,192 A | 7/1991 | Wrighton et al. |
| 5,035,860 A | 7/1991 | Kleingeld et al. |
| 5,036,860 A | 8/1991 | Leigh et al. |
| 5,036,861 A | 8/1991 | Sembrowich et al. |
| 5,037,527 A | 8/1991 | Hayashi et al. |
| 5,049,487 A | 9/1991 | Phillips et al. |
| 5,050,612 A | 9/1991 | Matsumura |
| 5,055,171 A | 10/1991 | Peck |
| 5,058,592 A | 10/1991 | Whisler |
| 5,063,081 A | 11/1991 | Cozzette et al. |
| 5,068,536 A | 11/1991 | Rosenthal |
| 5,070,535 A | 12/1991 | Hochmair et al. |
| 5,073,500 A | 12/1991 | Saito et al. |
| 5,077,476 A | 12/1991 | Rosenthal |
| 5,078,854 A | 1/1992 | Burgess et al. |
| 5,082,550 A | 1/1992 | Rishpon et al. |
| 5,082,786 A | 1/1992 | Nakamoto |
| 5,084,828 A | 1/1992 | Kaufman et al. |
| 5,089,112 A | 2/1992 | Skotheim et al. |
| 5,094,951 A | 3/1992 | Rosenberg |
| 5,095,904 A | 3/1992 | Seligman et al. |
| 5,096,560 A | 3/1992 | Takai et al. |
| 5,096,836 A | 3/1992 | Macho et al. |
| 5,097,834 A | 3/1992 | Skrabal |
| 5,101,814 A | 4/1992 | Palti |
| 5,106,365 A | 4/1992 | Hernandez |
| 5,108,564 A | 4/1992 | Szuminsky et al. |
| 5,109,850 A | 5/1992 | Blanco et al. |
| 5,111,539 A | 5/1992 | Hiruta et al. |
| 5,111,818 A | 5/1992 | Suzuji et al. |
| 5,114,678 A | 5/1992 | Crawford et al. |
| 5,120,420 A | 6/1992 | Nankai et al. |
| 5,120,421 A | 6/1992 | Glass et al. |
| 5,122,925 A | 6/1992 | Inpyn |
| 5,124,661 A | 6/1992 | Zelin et al. |
| 5,126,034 A | 6/1992 | Carter et al. |
| 5,126,247 A | 6/1992 | Palmer et al. |
| 5,130,009 A | 7/1992 | Marsoner et al. |
| 5,133,856 A | 7/1992 | Yamaguchi et al. |
| 5,134,391 A | 7/1992 | Okada |
| 5,135,003 A | 8/1992 | Souma |
| 5,139,023 A | 8/1992 | Stanley et al. |
| 5,140,393 A | 8/1992 | Hijikihigawa et al. |
| 5,141,868 A | 8/1992 | Shanks et al. |
| 5,161,532 A | 11/1992 | Joseph |
| 5,165,407 A | 11/1992 | Wilson et al. |
| 5,168,046 A | 12/1992 | Hamamoto et al. |
| 5,174,291 A | 12/1992 | Schoonen et al. |
| 5,176,644 A | 1/1993 | Srisathapat et al. |
| 5,176,662 A | 1/1993 | Bartholomew et al. |
| 5,182,707 A | 1/1993 | Cooper et al. |
| 5,184,359 A | 2/1993 | Tsukamura et al. |
| 5,185,256 A | 2/1993 | Nankai et al. |
| 5,190,041 A | 3/1993 | Palti |
| 5,192,415 A | 3/1993 | Yoshioka et al. |
| 5,192,416 A | 3/1993 | Wang et al. |
| 5,193,539 A | 3/1993 | Schulman et al. |
| 5,193,540 A | 3/1993 | Schulman et al. |
| 5,197,322 A | 3/1993 | Indravudh |
| 5,198,367 A | 3/1993 | Aizawa et al. |
| 5,200,051 A | 4/1993 | Cozzette et al. |
| 5,202,261 A | 4/1993 | Musho et al. |
| 5,205,920 A | 4/1993 | Oyama et al. |
| 5,206,145 A | 4/1993 | Cattell |
| 5,208,154 A | 5/1993 | Weaver et al. |
| 5,209,229 A | 5/1993 | Gilli |
| 5,215,887 A | 6/1993 | Saito |
| 5,216,597 A | 6/1993 | Beckers |
| 5,217,442 A | 6/1993 | Davis |
| 5,217,595 A | 6/1993 | Smith et al. |
| 5,227,042 A | 7/1993 | Zawodzinski et al. |
| 5,229,282 A | 7/1993 | Yoshioka et al. |
| 5,236,143 A | 8/1993 | Dragon |
| 5,237,993 A | 8/1993 | Skrabal |
| 5,246,867 A | 9/1993 | Lakowicz et al. |
| 5,250,439 A | 10/1993 | Musho et al. |
| 5,251,126 A | 10/1993 | Kahn et al. |
| 5,257,971 A | 11/1993 | Lord et al. |
| 5,257,980 A | 11/1993 | Van Antwerp et al. |
| 5,261,401 A | 11/1993 | Baker et al. |
| 5,262,035 A | 11/1993 | Gregg et al. |
| 5,262,305 A | 11/1993 | Heller et al. |
| 5,264,103 A | 11/1993 | Yoshioka et al. |
| 5,264,104 A | 11/1993 | Gregg et al. |
| 5,264,105 A | 11/1993 | Gregg et al. |
| 5,264,106 A | 11/1993 | McAleer et al. |
| 5,265,888 A | 11/1993 | Yamamoto et al. |
| 5,266,179 A | 11/1993 | Nankai et al. |
| 5,269,212 A | 12/1993 | Peters et al. |
| 5,271,815 A | 12/1993 | Wong |
| 5,272,060 A | 12/1993 | Hamamoto et al. |
| 5,275,159 A | 1/1994 | Griebel |
| 5,278,079 A | 1/1994 | Gubinski et al. |
| 5,279,294 A | 1/1994 | Anderson |
| 5,282,950 A | 2/1994 | Dietze et al. |
| 5,284,156 A | 2/1994 | Schramm et al. |
| 5,285,792 A | 2/1994 | Sjoquist et al. |
| 5,286,362 A | 2/1994 | Hoenes et al. |
| 5,286,364 A | 2/1994 | Yacynych et al. |
| 5,288,636 A | 2/1994 | Pollmann et al. |
| 5,291,887 A | 3/1994 | Stanley et al. |
| 5,293,546 A | 3/1994 | Tadros et al. |
| 5,293,877 A | 3/1994 | O'Hara et al. |
| 5,299,571 A | 4/1994 | Mastrototaro |
| 5,304,468 A | 4/1994 | Phillips et al. |
| 5,307,263 A | 4/1994 | Brown |
| 5,309,919 A | 5/1994 | Snell et al. |
| 5,310,885 A | 5/1994 | Maier et al. |
| 5,320,098 A | 6/1994 | Davidson |
| 5,320,725 A | 6/1994 | Gregg et al. |
| 5,322,063 A | 6/1994 | Allen et al. |
| 5,324,303 A | 6/1994 | Strong et al. |
| 5,324,316 A | 6/1994 | Schulman et al. |
| 5,326,449 A | 7/1994 | Cunningham |
| 5,333,615 A | 8/1994 | Craelius et al. |
| 5,337,258 A | 8/1994 | Dennis |
| 5,337,747 A | 8/1994 | Neftel |
| 5,340,722 A | 8/1994 | Wolfbeis et al. |
| 5,342,408 A | 8/1994 | deCoriolis et al. |

| | | | | | |
|---|---|---|---|---|---|
| 5,342,789 A | 8/1994 | Chick et al. | 5,529,676 A | 6/1996 | Maley et al. |
| 5,352,348 A | 10/1994 | Young et al. | 5,531,878 A | 7/1996 | Vadgama et al. |
| 5,356,348 A | 10/1994 | Bellio et al. | 5,532,686 A | 7/1996 | Urbas et al. |
| 5,356,786 A | 10/1994 | Heller et al. | 5,538,511 A | 7/1996 | Van Antwerp et al. |
| 5,358,135 A | 10/1994 | Robbins et al. | 5,545,152 A | 8/1996 | Funderburk et al. |
| 5,358,514 A | 10/1994 | Schulman et al. | 5,545,191 A | 8/1996 | Mann et al. |
| 5,360,404 A | 11/1994 | Novacek et al. | 5,549,113 A | 8/1996 | Halleck et al. |
| 5,364,797 A | 11/1994 | Olson et al. | 5,549,115 A | 8/1996 | Morgan et al. |
| 5,366,609 A | 11/1994 | White et al. | 5,552,027 A | 9/1996 | Birkle et al. |
| 5,368,028 A | 11/1994 | Palti | 5,554,166 A | 9/1996 | Lange et al. |
| 5,370,622 A | 12/1994 | Livingston et al. | 5,556,524 A | 9/1996 | Albers |
| 5,371,687 A | 12/1994 | Holmes, II et al. | 5,560,357 A | 10/1996 | Faupei et al. |
| 5,371,734 A | 12/1994 | Fischer | 5,562,713 A | 10/1996 | Silvian |
| 5,372,133 A | 12/1994 | Hogen Esch | 5,565,085 A | 10/1996 | Ikeda et al. |
| 5,372,427 A | 12/1994 | Padovani et al. | 5,567,302 A | 10/1996 | Song et al. |
| 5,376,070 A | 12/1994 | Purvis et al. | 5,568,806 A | 10/1996 | Cheney, II et al. |
| 5,376,251 A | 12/1994 | Kaneko et al. | 5,569,186 A | 10/1996 | Lord et al. |
| 5,377,258 A | 12/1994 | Bro | 5,569,212 A | 10/1996 | Brown |
| 5,378,628 A | 1/1995 | Gratzel et al. | 5,573,647 A | 11/1996 | Maley et al. |
| 5,379,238 A | 1/1995 | Stark | 5,575,895 A | 11/1996 | Ikeda et al. |
| 5,379,764 A | 1/1995 | Barnes et al. | 5,580,527 A | 12/1996 | Bell et al. |
| 5,380,422 A | 1/1995 | Negishis et al. | 5,580,794 A | 12/1996 | Allen |
| 5,382,346 A | 1/1995 | Uenoyama et al. | 5,582,184 A | 12/1996 | Erickson et al. |
| 5,387,327 A | 2/1995 | Khan | 5,582,697 A | 12/1996 | Ikeda et al. |
| 5,390,671 A | 2/1995 | Lord et al. | 5,582,698 A | 12/1996 | Flaherty et al. |
| 5,391,250 A | 2/1995 | Cheney, II et al. | 5,584,813 A | 12/1996 | Livingston et al. |
| 5,393,903 A | 2/1995 | Gratzel et al. | 5,586,553 A | 12/1996 | Halli et al. |
| 5,395,504 A | 3/1995 | Saurer et al. | 5,589,326 A | 12/1996 | Deng et al. |
| 5,399,823 A | 3/1995 | McCusker | 5,593,852 A | 1/1997 | Heller et al. |
| 5,400,782 A | 3/1995 | Beaubiah | 5,594,906 A | 1/1997 | Holmes, II et al. |
| 5,408,999 A | 4/1995 | Singh et al. | 5,596,150 A | 1/1997 | Arndy et al. |
| 5,410,326 A | 4/1995 | Goldstein | 5,596,994 A | 1/1997 | Bro |
| 5,410,471 A | 4/1995 | Alyfuku et al. | 5,601,435 A | 2/1997 | Quy |
| 5,410,474 A | 4/1995 | Fox | 5,601,694 A | 2/1997 | Maley et al. |
| 5,411,647 A | 5/1995 | Johnson et al. | 5,605,152 A | 2/1997 | Slate et al. |
| 5,413,690 A | 5/1995 | Kost et al. | 5,609,575 A | 3/1997 | Larson et al. |
| 5,422,246 A | 6/1995 | Koopal et al. | 5,611,900 A | 3/1997 | Worden et al. |
| 5,431,160 A | 7/1995 | Wilkins | 5,615,135 A | 3/1997 | Waclawsky et al. |
| 5,431,691 A | 7/1995 | Snell et al. | 5,615,671 A | 4/1997 | Schoonen et al. |
| 5,431,921 A | 7/1995 | Thombre | 5,616,222 A | 4/1997 | Maley et al. |
| 5,433,710 A | 7/1995 | Van Antwerp et al. | 5,617,851 A | 4/1997 | Lipkovker |
| 5,437,973 A | 8/1995 | Vadgama et al. | 5,623,925 A | 4/1997 | Swenson et al. |
| 5,437,999 A | 8/1995 | Diebold et al. | 5,623,933 A | 4/1997 | Amano et al. |
| 5,445,611 A | 8/1995 | Eppstein et al. | 5,628,309 A | 5/1997 | Brown |
| 5,445,920 A | 8/1995 | Saito | 5,628,310 A | 5/1997 | Rao et al. |
| 5,456,692 A | 10/1995 | Smith, Jr. et al. | 5,628,890 A | 5/1997 | Carter et al. |
| 5,456,940 A | 10/1995 | Funderburk | 5,629,981 A | 5/1997 | Nerlikar |
| 5,458,140 A | 10/1995 | Eppstein et al. | 5,634,468 A | 6/1997 | Platt et al. |
| 5,460,618 A | 10/1995 | Harreld | 5,637,095 A | 6/1997 | Nason et al. |
| 5,462,525 A | 10/1995 | Srisathapat et al. | 5,640,764 A | 6/1997 | Strojnik |
| 5,462,645 A | 10/1995 | Albery et al. | 5,640,954 A | 6/1997 | Pfeiffer et al. |
| 5,466,218 A | 11/1995 | Srisathapat et al. | 5,643,212 A | 7/1997 | Coutre et al. |
| 5,467,778 A | 11/1995 | Catt et al. | 5,647,853 A | 7/1997 | Feldmann et al. |
| 5,469,846 A | 11/1995 | Khan | 5,650,062 A | 7/1997 | Ikeda et al. |
| 5,472,317 A | 12/1995 | Field et al. | 5,651,767 A | 7/1997 | Schulman et al. |
| 5,476,460 A | 12/1995 | Montalvo | 5,651,869 A | 7/1997 | Yoshioka et al. |
| 5,477,855 A | 12/1995 | Schindler et al. | 5,653,239 A | 8/1997 | Pompei et al. |
| 5,482,473 A | 1/1996 | Lord et al. | 5,660,163 A | 8/1997 | Schulman et al. |
| 5,484,404 A | 1/1996 | Schulman et al. | 5,665,065 A | 9/1997 | Colman et al. |
| 5,487,751 A | 1/1996 | Radons et al. | 5,665,222 A | 9/1997 | Heller et al. |
| 5,491,474 A | 2/1996 | Suni et al. | 5,667,983 A | 9/1997 | Abel et al. |
| 5,494,562 A | 2/1996 | Maley et al. | 5,670,031 A | 9/1997 | Hintsche et al. |
| 5,496,453 A | 3/1996 | Uenoyama et al. | 5,678,571 A | 10/1997 | Brown |
| 5,497,772 A | 3/1996 | Schulman et al. | 5,679,690 A | 10/1997 | Andre et al. |
| 5,501,956 A | 3/1996 | Wada et al. | 5,680,858 A | 10/1997 | Hansen et al. |
| 5,505,709 A | 4/1996 | Funderburk | 5,682,233 A | 10/1997 | Brinda |
| 5,505,713 A | 4/1996 | Van Antwerp et al. | 5,686,717 A | 11/1997 | Knowles et al. |
| 5,507,288 A | 4/1996 | Bocker et al. | 5,695,623 A | 12/1997 | Michel et al. |
| 5,508,171 A | 4/1996 | Walling et al. | 5,695,949 A | 12/1997 | Galen et al. |
| 5,509,410 A | 4/1996 | Hill et al. | 5,701,894 A | 12/1997 | Cherry et al. |
| 5,514,103 A | 5/1996 | Srisathapat et al. | 5,704,922 A | 1/1998 | Brown |
| 5,514,253 A | 5/1996 | Davis et al. | 5,707,502 A | 1/1998 | McCaffrey et al. |
| 5,514,718 A | 5/1996 | Lewis et al. | 5,708,247 A | 1/1998 | McAleer et al. |
| 5,518,006 A | 5/1996 | Mawhirt et al. | 5,710,630 A | 1/1998 | Essenpreis et al. |
| 5,520,787 A | 5/1996 | Hanagan et al. | 5,711,001 A | 1/1998 | Bussan et al. |
| 5,522,865 A | 6/1996 | Schulman et al. | 5,711,297 A | 1/1998 | Iliff et al. |
| 5,525,511 A | 6/1996 | D'Costa | 5,711,861 A | 1/1998 | Ward et al. |
| 5,526,120 A | 6/1996 | Jina et al. | 5,711,862 A | 1/1998 | Sakoda et al. |
| 5,527,307 A | 6/1996 | Srisathapat et al. | 5,711,868 A | 1/1998 | Maley et al. |

| | | | | | | |
|---|---|---|---|---|---|---|
| 5,718,234 A | 2/1998 | Warden et al. | | 5,925,021 A | 7/1999 | Castellano et al. |
| 5,720,733 A | 2/1998 | Brown | | 5,931,791 A | 8/1999 | Saltzstein et al. |
| 5,720,862 A | 2/1998 | Hamamoto et al. | | 5,933,136 A | 8/1999 | Brown |
| 5,721,783 A | 2/1998 | Anderson | | 5,939,609 A | 8/1999 | Knapp et al. |
| 5,722,397 A | 3/1998 | Eppstein | | 5,940,801 A | 8/1999 | Brown |
| 5,724,030 A | 3/1998 | Urbas et al. | | 5,942,979 A | 8/1999 | Luppino |
| 5,727,548 A | 3/1998 | Hill et al. | | 5,945,345 A | 8/1999 | Blatt et al. |
| 5,730,124 A | 3/1998 | Yamauchi | | 5,947,921 A | 9/1999 | Johnson et al. |
| 5,730,654 A | 3/1998 | Brown | | 5,948,512 A | 9/1999 | Kubota et al. |
| 5,735,273 A | 4/1998 | Kurnik et al. | | 5,950,632 A | 9/1999 | Reber et al. |
| 5,735,285 A | 4/1998 | Albert et al. | | 5,951,300 A | 9/1999 | Brown |
| 5,741,211 A | 4/1998 | Renirie et al. | | 5,951,485 A | 9/1999 | Cyrus et al. |
| 5,741,688 A | 4/1998 | Oxenboll et al. | | 5,951,492 A | 9/1999 | Douglas et al. |
| 5,746,217 A | 5/1998 | Erickson et al. | | 5,951,521 A | 9/1999 | Mastrototaro et al. |
| 5,749,907 A | 5/1998 | Mann | | 5,951,836 A | 9/1999 | McAleer et al. |
| 5,750,926 A | 5/1998 | Schulman et al. | | 5,954,643 A | 9/1999 | Van Antwerp |
| 5,770,028 A | 6/1998 | Maley et al. | | 5,954,685 A | 9/1999 | Tierney |
| 5,771,001 A | 6/1998 | Cobb | | 5,954,700 A | 9/1999 | Kovelman |
| 5,771,890 A | 6/1998 | Tamada | | 5,956,501 A | 9/1999 | Brown |
| 5,772,586 A | 6/1998 | Heinonen et al. | | 5,957,854 A | 9/1999 | Besson et al. |
| 5,777,060 A | 7/1998 | Van Antwerp | | 5,957,890 A | 9/1999 | Mann et al. |
| 5,779,665 A | 7/1998 | Mastrototaro et al. | | 5,957,958 A | 9/1999 | Schulman et al. |
| 5,781,024 A | 7/1998 | Blomberg et al. | | 5,960,403 A | 9/1999 | Brown |
| 5,782,814 A | 7/1998 | Brown et al. | | 5,961,451 A | 10/1999 | Reber et al. |
| 5,785,681 A | 7/1998 | Indravudh | | 5,964,993 A | 10/1999 | Blubaugh, Jr. et al. |
| 5,786,439 A | 7/1998 | Van Antwerp et al. | | 5,965,380 A | 10/1999 | Heller et al. |
| 5,786,584 A | 7/1998 | Button et al. | | 5,968,839 A | 10/1999 | Blatt et al. |
| 5,788,678 A | 8/1998 | Van Antwerp | | 5,971,922 A | 10/1999 | Arita et al. |
| 5,791,344 A | 8/1998 | Schulman et al. | | 5,971,941 A | 10/1999 | Simons et al. |
| 5,792,117 A | 8/1998 | Brown | | 5,974,124 A | 10/1999 | Schlueter, Jr. et al. |
| 5,793,292 A | 8/1998 | Ivey | | 5,977,476 A | 11/1999 | Guha et al. |
| 5,800,420 A | 9/1998 | Gross et al. | | 5,981,294 A | 11/1999 | Blatt et al. |
| 5,804,047 A | 9/1998 | Karube et al. | | 5,989,409 A | 11/1999 | Kurnik et al. |
| 5,804,048 A | 9/1998 | Wong et al. | | 5,994,476 A | 11/1999 | Shin et al. |
| 5,807,315 A | 9/1998 | Van Antwerp et al. | | 5,995,860 A | 11/1999 | Sun et al. |
| 5,807,375 A | 9/1998 | Gross et al. | | 5,997,476 A * | 12/1999 | Brown ........................ 600/300 |
| 5,814,599 A | 9/1998 | Mitragotri et al. | | 5,999,848 A | 12/1999 | Gord et al. |
| 5,820,551 A | 10/1998 | Hill et al. | | 5,999,849 A | 12/1999 | Gord et al. |
| 5,820,570 A | 10/1998 | Erickson et al. | | 6,001,067 A | 12/1999 | Shults et al. |
| 5,820,622 A | 10/1998 | Gross et al. | | 6,002,954 A | 12/1999 | Van Antwerp et al. |
| 5,822,715 A | 10/1998 | Worthington et al. | | 6,002,961 A | 12/1999 | Mitragotri et al. |
| 5,825,488 A | 10/1998 | Kohl et al. | | 6,004,441 A | 12/1999 | Fujiwara et al. |
| 5,827,179 A | 10/1998 | Lichter et al. | | 6,011,984 A | 1/2000 | Van Antwerp et al. |
| 5,827,183 A | 10/1998 | Kurnik et al. | | 6,014,577 A | 1/2000 | Henning et al. |
| 5,827,184 A | 10/1998 | Netherly et al. | | 6,018,678 A | 1/2000 | Mitragotri et al. |
| 5,828,943 A | 10/1998 | Brown | | 6,023,629 A | 2/2000 | Tamada |
| 5,830,064 A | 11/1998 | Bradish et al. | | 6,024,699 A | 2/2000 | Surwit et al. |
| 5,830,341 A | 11/1998 | Gilmartin | | 6,026,320 A | 2/2000 | Carlson et al. |
| 5,832,448 A | 11/1998 | Brown | | 6,027,459 A | 2/2000 | Shain et al. |
| 5,833,603 A | 11/1998 | Kovacs et al. | | 6,027,692 A | 2/2000 | Galen et al. |
| 5,834,224 A | 11/1998 | Ruger et al. | | 6,032,059 A | 2/2000 | Henning et al. |
| 5,837,454 A | 11/1998 | Cozzette et al. | | 6,032,119 A * | 2/2000 | Brown et al. ..................... 705/2 |
| 5,837,546 A | 11/1998 | Allen et al. | | 6,032,199 A | 2/2000 | Lim et al. |
| 5,840,020 A | 11/1998 | Heinonen et al. | | 6,033,866 A | 3/2000 | Guo et al. |
| 5,842,983 A | 12/1998 | Abel et al. | | 6,035,237 A | 3/2000 | Schulman et al. |
| 5,843,140 A | 12/1998 | Strojnik | | 6,040,194 A | 3/2000 | Chick et al. |
| 5,846,702 A | 12/1998 | Deng et al. | | 6,041,253 A | 3/2000 | Kost et al. |
| 5,846,744 A | 12/1998 | Athey et al. | | 6,043,437 A | 3/2000 | Schulman et al. |
| 5,851,197 A | 12/1998 | Marano et al. | | 6,049,727 A | 4/2000 | Crothall |
| 5,854,078 A | 12/1998 | Asher et al. | | 6,052,565 A | 4/2000 | Ishikura et al. |
| 5,854,189 A | 12/1998 | Kruse et al. | | 6,056,718 A | 5/2000 | Funderburk et al. |
| 5,857,967 A | 1/1999 | Frid et al. | | 6,063,459 A | 5/2000 | Velte |
| 5,857,983 A | 1/1999 | Douglas et al. | | 6,066,243 A | 5/2000 | Anderson et al. |
| 5,860,917 A | 1/1999 | Comanor et al. | | 6,067,474 A | 5/2000 | Schulman et al. |
| 5,872,713 A | 2/1999 | Douglas et al. | | 6,068,615 A | 5/2000 | Brown et al. |
| 5,876,484 A | 3/1999 | Raskin et al. | | 6,071,249 A | 6/2000 | Cunningham et al. |
| 5,879,163 A | 3/1999 | Brown et al. | | 6,071,251 A | 6/2000 | Cunningham et al. |
| 5,879,311 A | 3/1999 | Duchon et al. | | 6,071,294 A | 6/2000 | Simons et al. |
| 5,880,829 A | 3/1999 | Kauhaniemi et al. | | 6,071,391 A | 6/2000 | Gotoh et al. |
| 5,882,494 A | 3/1999 | Van Antwerp | | 6,073,031 A | 6/2000 | Helstab et al. |
| 5,885,211 A | 3/1999 | Eppstein et al. | | 6,081,736 A | 6/2000 | Colvin et al. |
| 5,887,133 A | 3/1999 | Brown et al. | | 6,083,710 A | 7/2000 | Heller et al. |
| 5,891,049 A | 4/1999 | Cyrus et al. | | 6,088,608 A | 7/2000 | Schulman et al. |
| 5,897,493 A | 4/1999 | Brown | | 6,091,975 A | 7/2000 | Daddona et al. |
| 5,898,025 A | 4/1999 | Burg et al. | | 6,091,976 A | 7/2000 | Pfeiffer et al. |
| 5,899,855 A | 5/1999 | Brown | | 6,091,987 A | 7/2000 | Thompson |
| 5,913,310 A | 6/1999 | Brown | | 6,093,156 A | 7/2000 | Cunningham et al. |
| 5,917,346 A | 6/1999 | Gord | | 6,093,167 A | 7/2000 | Houben et al. |
| 5,918,603 A | 7/1999 | Brown | | 6,093,172 A | 7/2000 | Funderburk et al. |

| | | |
|---|---|---|
| 6,097,480 A | 8/2000 | Kaplan |
| 6,097,831 A | 8/2000 | Wieck et al. |
| 6,099,484 A | 8/2000 | Douglas et al. |
| 6,101,478 A | 8/2000 | Brown |
| 6,103,033 A | 8/2000 | Say et al. |
| 6,106,780 A | 8/2000 | Douglas et al. |
| 6,110,148 A | 8/2000 | Brown et al. |
| 6,110,152 A | 8/2000 | Kovelman |
| 6,113,578 A | 9/2000 | Brown |
| 6,117,290 A | 9/2000 | Say et al. |
| 6,119,028 A | 9/2000 | Schulman et al. |
| 6,120,676 A | 9/2000 | Heller et al. |
| 6,121,009 A | 9/2000 | Heller et al. |
| 6,121,611 A | 9/2000 | Lindsay et al. |
| 6,122,351 A | 9/2000 | Schlueter, Jr. et al. |
| 6,125,978 A | 10/2000 | Ando et al. |
| 6,130,623 A | 10/2000 | MacLellan et al. |
| 6,134,461 A | 10/2000 | Say et al. |
| 6,134,504 A | 10/2000 | Douglas et al. |
| 6,139,718 A | 10/2000 | Kurnik et al. |
| 6,141,573 A | 10/2000 | Kurnik et al. |
| 6,142,939 A | 11/2000 | Eppstein et al. |
| 6,143,164 A | 11/2000 | Heller et al. |
| 6,144,837 A | 11/2000 | Quy |
| 6,144,869 A | 11/2000 | Berner et al. |
| 6,144,871 A | 11/2000 | Saito et al. |
| 6,144,922 A | 11/2000 | Douglas et al. |
| 6,148,094 A | 11/2000 | Kinsella |
| 6,150,128 A | 11/2000 | Uretsky |
| 6,151,586 A | 11/2000 | Brown |
| 6,153,062 A | 11/2000 | Saito et al. |
| 6,153,069 A | 11/2000 | Pottgen et al. |
| 6,159,147 A | 12/2000 | Lichter et al. |
| 6,161,095 A | 12/2000 | Brown |
| 6,162,611 A | 12/2000 | Heller et al. |
| 6,162,639 A | 12/2000 | Douglas |
| 6,164,284 A * | 12/2000 | Schulman et al. ............ 128/899 |
| 6,167,362 A | 12/2000 | Brown et al. |
| 6,168,563 B1 | 1/2001 | Brown |
| 6,170,318 B1 | 1/2001 | Lewis |
| 6,175,752 B1 | 1/2001 | Say et al. |
| 6,180,416 B1 | 1/2001 | Kurnik et al. |
| 6,186,145 B1 | 2/2001 | Brown |
| 6,192,891 B1 | 2/2001 | Gravel et al. |
| 6,193,873 B1 | 2/2001 | Ohara et al. |
| 6,196,970 B1 | 3/2001 | Brown |
| 6,198,957 B1 | 3/2001 | Green |
| 6,200,265 B1 | 3/2001 | Walsh et al. |
| 6,201,979 B1 | 3/2001 | Kurnik et al. |
| 6,201,980 B1 | 3/2001 | Darrow et al. |
| 6,203,495 B1 | 3/2001 | Bardy et al. |
| 6,206,841 B1 | 3/2001 | Cunningham et al. |
| 6,207,400 B1 | 3/2001 | Kwon |
| 6,208,894 B1 * | 3/2001 | Schulman et al. ................ 607/2 |
| 6,210,272 B1 | 4/2001 | Brown |
| 6,210,976 B1 | 4/2001 | Sabbadini |
| 6,212,416 B1 | 4/2001 | Ward et al. |
| 6,219,565 B1 | 4/2001 | Cupp et al. |
| 6,219,574 B1 | 4/2001 | Cormier et al. |
| 6,224,745 B1 | 5/2001 | Baltruschat |
| 6,232,130 B1 | 5/2001 | Wolf |
| 6,232,370 B1 | 5/2001 | Kubota et al. |
| 6,233,471 B1 | 5/2001 | Berner et al. |
| 6,233,539 B1 | 5/2001 | Brown |
| 6,239,925 B1 | 5/2001 | Ardrey et al. |
| 6,241,862 B1 | 6/2001 | McAleer et al. |
| 6,246,330 B1 | 6/2001 | Nielsen |
| 6,246,992 B1 | 6/2001 | Brown |
| 6,248,065 B1 | 6/2001 | Brown |
| 6,248,067 B1 | 6/2001 | Causey, III et al. |
| 6,248,093 B1 | 6/2001 | Moberg |
| 6,251,260 B1 | 6/2001 | Heller et al. |
| 6,252,032 B1 | 6/2001 | Van Antwerp et al. |
| 6,253,804 B1 | 7/2001 | Safabash |
| 6,254,586 B1 | 7/2001 | Mann et al. |
| 6,256,643 B1 | 7/2001 | Cork et al. |
| 6,259,587 B1 | 7/2001 | Sheldon et al. |
| 6,259,937 B1 | 7/2001 | Schulman et al. |
| 6,260,022 B1 | 7/2001 | Brown |
| 6,266,645 B1 | 7/2001 | Simpson |
| 6,267,724 B1 | 7/2001 | Taylor |
| 6,268,161 B1 | 7/2001 | Han et al. |
| 6,270,445 B1 | 8/2001 | Dean, Jr. et al. |
| 6,272,364 B1 | 8/2001 | Kurnik |
| 6,275,717 B1 | 8/2001 | Gross et al. |
| 6,280,416 B1 | 8/2001 | Van Antwerp et al. |
| 6,280,587 B1 | 8/2001 | Matsumoto |
| 6,281,006 B1 | 8/2001 | Heller et al. |
| 6,283,943 B1 | 9/2001 | Dy et al. |
| 6,284,126 B1 | 9/2001 | Kurnik et al. |
| 6,284,478 B1 | 9/2001 | Heller et al. |
| 6,291,200 B1 | 9/2001 | LeJeune et al. |
| 6,293,925 B1 | 9/2001 | Safabash et al. |
| 6,294,281 B1 | 9/2001 | Heller |
| 6,294,997 B1 | 9/2001 | Paratore et al. |
| 6,295,463 B1 | 9/2001 | Stenzler |
| 6,295,506 B1 | 9/2001 | Heinonen et al. |
| 6,298,254 B2 | 10/2001 | Tamada |
| 6,299,578 B1 | 10/2001 | Kurnik et al. |
| 6,299,757 B1 | 10/2001 | Feldman et al. |
| 6,301,499 B1 | 10/2001 | Carlson et al. |
| 6,304,766 B1 | 10/2001 | Colvin, Jr. et al. |
| 6,306,104 B1 | 10/2001 | Cunningham et al. |
| 6,307,867 B1 | 10/2001 | Roobol et al. |
| 6,309,351 B1 | 10/2001 | Kurnik et al. |
| 6,309,884 B1 | 10/2001 | Cooper et al. |
| 6,313,749 B1 | 11/2001 | Horne et al. |
| 6,315,721 B2 * | 11/2001 | Schulman et al. ............. 600/301 |
| 6,319,540 B1 | 11/2001 | Van Antwerp et al. |
| 6,326,160 B1 | 12/2001 | Dunn et al. |
| 6,329,161 B1 | 12/2001 | Heller et al. |
| 6,329,929 B1 | 12/2001 | Weijand et al. |
| 6,330,426 B2 | 12/2001 | Brown et al. |
| 6,330,464 B1 | 12/2001 | Colvin, Jr. et al. |
| 6,331,518 B2 | 12/2001 | Hemm et al. |
| 6,334,778 B1 * | 1/2002 | Brown .......................... 434/258 |
| 6,336,900 B1 | 1/2002 | Alleckson et al. |
| 6,338,790 B1 | 1/2002 | Feldman et al. |
| 6,340,421 B1 | 1/2002 | Vachon et al. |
| 6,341,232 B1 | 1/2002 | Conn et al. |
| 6,356,776 B1 | 3/2002 | Berner et al. |
| 6,360,888 B1 | 3/2002 | McIvor et al. |
| 6,366,793 B1 | 4/2002 | Bell et al. |
| 6,366,794 B1 | 4/2002 | Moussy et al. |
| 6,368,141 B1 | 4/2002 | Van Antwerp et al. |
| 6,368,274 B1 | 4/2002 | Van Antwerp et al. |
| 6,370,410 B2 | 4/2002 | Kurnik et al. |
| 6,377,828 B1 | 4/2002 | Chaiken et al. |
| 6,379,301 B1 | 4/2002 | Worthington et al. |
| 6,381,577 B1 * | 4/2002 | Brown .............................. 705/2 |
| 6,383,767 B1 | 5/2002 | Polak |
| 6,387,048 B1 | 5/2002 | Schulman et al. |
| 6,391,643 B1 | 5/2002 | Chen et al. |
| 6,393,318 B1 | 5/2002 | Conn et al. |
| 6,398,562 B1 | 6/2002 | Butler et al. |
| 6,400,974 B1 | 6/2002 | Lesho |
| 6,405,066 B1 | 6/2002 | Essenpreis et al. |
| 6,413,393 B1 | 7/2002 | Van Antwerp et al. |
| 6,416,471 B1 | 7/2002 | Kumar et al. |
| 6,418,332 B1 | 7/2002 | Mastrototaro et al. |
| 6,418,346 B1 | 7/2002 | Nelson et al. |
| 6,424,847 B1 | 7/2002 | Mastrototaro et al. |
| 6,427,088 B1 | 7/2002 | Bowman, IV et al. |
| 6,434,409 B1 | 8/2002 | Pfeiffer et al. |
| 6,438,414 B1 | 8/2002 | Conn et al. |
| 6,440,068 B1 | 8/2002 | Brown et al. |
| 6,442,637 B1 | 8/2002 | Hawkins et al. |
| 6,443,942 B2 | 9/2002 | Van Antwerp et al. |
| 6,449,255 B1 | 9/2002 | Waclawsky et al. |
| 6,454,710 B1 | 9/2002 | Ballerstadt et al. |
| 6,462,162 B1 | 10/2002 | Van Antwerp et al. |
| 6,464,848 B1 | 10/2002 | Matsumoto |
| 6,466,810 B1 | 10/2002 | Ward et al. |
| 6,468,222 B1 | 10/2002 | Mault et al. |
| 6,472,122 B1 | 10/2002 | Schulman et al. |
| 6,475,750 B1 | 11/2002 | Han et al. |
| 6,477,395 B2 | 11/2002 | Schulman et al. |
| 6,478,736 B1 | 11/2002 | Mault |

| | | |
|---|---|---|
| 6,480,730 B2 | 11/2002 | Darrow et al. |
| 6,482,156 B2 | 11/2002 | Iliff |
| 6,482,158 B2 | 11/2002 | Mault |
| 6,482,604 B2 | 11/2002 | Kwon |
| 6,484,045 B1 | 11/2002 | Holker et al. |
| 6,484,046 B1 | 11/2002 | Say et al. |
| 6,485,138 B1 | 11/2002 | Kubota et al. |
| 6,494,830 B1 | 12/2002 | Wessel |
| 6,496,728 B2 | 12/2002 | Li et al. |
| 6,496,729 B2 | 12/2002 | Thompson |
| 6,497,655 B1 | 12/2002 | Linberg et al. |
| 6,505,059 B1 | 1/2003 | Kollias et al. |
| 6,505,121 B1 | 1/2003 | Russel |
| 6,512,939 B1 | 1/2003 | Colvin et al. |
| 6,513,532 B2 | 2/2003 | Mault et al. |
| 6,514,718 B2 | 2/2003 | Heller et al. |
| 6,515,593 B1 | 2/2003 | Stark et al. |
| 6,520,326 B2 | 2/2003 | McIvor et al. |
| 6,529,755 B2 | 3/2003 | Kurnik et al. |
| 6,529,772 B2 | 3/2003 | Carlson et al. |
| 6,530,915 B1 | 3/2003 | Eppstein et al. |
| 6,534,322 B1 | 3/2003 | Sabbadini |
| 6,534,323 B1 | 3/2003 | Sabbadini |
| 6,535,753 B1 | 3/2003 | Raskas |
| 6,537,243 B1 | 3/2003 | Henning et al. |
| 6,540,675 B2 | 4/2003 | Aceti et al. |
| 6,541,266 B2 | 4/2003 | Modzelewski et al. |
| 6,544,212 B2 | 4/2003 | Galley et al. |
| 6,546,269 B1 | 4/2003 | Kurnik |
| 6,549,796 B2 | 4/2003 | Sohrab |
| 6,551,276 B1 | 4/2003 | Mann et al. |
| 6,551,494 B1 | 4/2003 | Heller et al. |
| 6,553,244 B2 | 4/2003 | Lesho et al. |
| 6,554,798 B1 | 4/2003 | Mann et al. |
| 6,558,320 B1 | 5/2003 | Causey, III et al. |
| 6,558,321 B1 | 5/2003 | Burd et al. |
| 6,558,351 B1 | 5/2003 | Steil et al. |
| 6,560,471 B1 | 5/2003 | Heller et al. |
| 6,561,975 B1 | 5/2003 | Pool et al. |
| 6,561,978 B1 | 5/2003 | Conn et al. |
| 6,562,001 B2 * | 5/2003 | Lebel et al. ............ 604/65 |
| 6,564,105 B2 | 5/2003 | Starkweather et al. |
| 6,564,807 B1 * | 5/2003 | Schulman et al. ............ 128/899 |
| 6,565,509 B1 | 5/2003 | Say et al. |
| 6,571,128 B2 * | 5/2003 | Lebel et al. ............ 607/60 |
| 6,571,200 B1 | 5/2003 | Mault |
| 6,574,510 B2 | 6/2003 | Von Arx et al. |
| 6,576,101 B1 | 6/2003 | Heller et al. |
| 6,576,117 B1 | 6/2003 | Iketaki et al. |
| 6,577,899 B2 * | 6/2003 | Lebel et al. ............ 607/60 |
| 6,579,231 B1 | 6/2003 | Phipps |
| 6,579,498 B1 | 6/2003 | Eglise |
| 6,579,690 B1 | 6/2003 | Bonnecaze et al. |
| 6,584,335 B1 | 6/2003 | Haar et al. |
| 6,585,644 B2 | 7/2003 | Lebel et al. |
| 6,587,705 B1 | 7/2003 | Kim et al. |
| 6,591,125 B1 | 7/2003 | Buse et al. |
| 6,591,126 B2 | 7/2003 | Roeper et al. |
| 6,594,514 B2 | 7/2003 | Berner et al. |
| 6,595,919 B2 | 7/2003 | Berner et al. |
| 6,595,929 B2 | 7/2003 | Stivoric et al. |
| 6,602,678 B2 | 8/2003 | Kwon et al. |
| 6,602,909 B1 | 8/2003 | Jarowski |
| 6,605,200 B1 | 8/2003 | Mao et al. |
| 6,605,201 B1 | 8/2003 | Mao et al. |
| 6,607,509 B2 | 8/2003 | Bobroff et al. |
| 6,608,562 B1 | 8/2003 | Kimura et al. |
| 6,610,012 B2 | 8/2003 | Mault |
| 6,612,306 B1 | 9/2003 | Mault |
| 6,615,078 B1 | 9/2003 | Burson et al. |
| 6,616,613 B1 * | 9/2003 | Goodman ............ 600/504 |
| 6,618,603 B2 | 9/2003 | Varalli et al. |
| 6,620,106 B2 | 9/2003 | Mault |
| 6,627,058 B1 | 9/2003 | Chan |
| 6,629,934 B2 | 10/2003 | Mault et al. |
| 6,633,772 B2 | 10/2003 | Ford et al. |
| 6,635,014 B2 | 10/2003 | Starkweather et al. |
| 6,635,167 B1 | 10/2003 | Batman et al. |
| 6,641,533 B2 | 11/2003 | Causey, III et al. |
| 6,642,015 B2 | 11/2003 | Vachon et al. |
| 6,645,142 B2 | 11/2003 | Braig et al. |
| 6,645,368 B1 | 11/2003 | Beaty et al. |
| 6,648,821 B2 * | 11/2003 | Lebel et al. ............ 600/300 |
| 6,653,091 B1 | 11/2003 | Dunn et al. |
| 6,654,625 B1 | 11/2003 | Say et al. |
| 6,659,948 B2 | 12/2003 | Lebel et al. |
| 6,668,196 B1 | 12/2003 | Villegas et al. |
| 6,671,554 B2 | 12/2003 | Gibson et al. |
| 6,673,625 B2 | 1/2004 | Satcher, Jr. et al. |
| 6,682,938 B1 | 1/2004 | Satcher, Jr. et al. |
| 6,683,040 B2 | 1/2004 | Bragulla et al. |
| 6,687,522 B2 | 2/2004 | Tamada |
| 6,687,546 B2 | 2/2004 | Lebel et al. |
| 6,689,056 B1 | 2/2004 | Kilcoyne et al. |
| 6,690,276 B1 | 2/2004 | Marino |
| 6,693,069 B2 | 2/2004 | Korber et al. |
| 6,694,158 B2 | 2/2004 | Polak |
| 6,694,191 B2 | 2/2004 | Starkweather et al. |
| 6,695,860 B1 | 2/2004 | Ward et al. |
| 6,701,270 B1 | 3/2004 | Miller et al. |
| 6,702,857 B2 | 3/2004 | Brauker et al. |
| 6,704,587 B1 | 3/2004 | Kumar et al. |
| 6,708,057 B2 | 3/2004 | Marganroth |
| 6,711,423 B2 | 3/2004 | Colvin, Jr. |
| 6,723,046 B2 | 4/2004 | Lichtenstein et al. |
| 6,728,560 B2 | 4/2004 | Kollias et al. |
| 6,731,976 B2 | 5/2004 | Penn et al. |
| 6,733,446 B2 | 5/2004 | Lebel et al. |
| 6,734,162 B2 | 5/2004 | Van Antwerp et al. |
| 6,735,183 B2 | 5/2004 | O'Toole et al. |
| 6,736,777 B2 | 5/2004 | Kim et al. |
| 6,736,797 B1 | 5/2004 | Larsen et al. |
| 6,737,401 B2 | 5/2004 | Kim et al. |
| 6,738,654 B2 | 5/2004 | Sohrab |
| 6,740,075 B2 | 5/2004 | Lebel et al. |
| 6,741,163 B1 | 5/2004 | Roberts |
| 6,741,876 B1 | 5/2004 | Scecina et al. |
| 6,741,877 B1 | 5/2004 | Shults et al. |
| 6,746,582 B2 | 6/2004 | Heller et al. |
| 6,748,445 B1 | 6/2004 | Darcy et al. |
| 6,749,587 B2 | 6/2004 | Flaherty |
| 6,750,311 B1 | 6/2004 | Van Antwerp et al. |
| 6,758,810 B2 * | 7/2004 | Lebel et al. ............ 600/300 |
| 6,766,183 B2 | 7/2004 | Walsh et al. |
| 6,766,201 B2 | 7/2004 | Von Arx et al. |
| 6,768,425 B2 | 7/2004 | Flaherty et al. |
| 6,770,030 B1 | 8/2004 | Schaupp et al. |
| 6,770,729 B2 | 8/2004 | Van Antwerp et al. |
| 6,771,995 B2 | 8/2004 | Kurnik et al. |
| 6,773,563 B2 | 8/2004 | Matsumoto |
| 6,780,156 B2 | 8/2004 | Haueter et al. |
| 6,780,297 B2 | 8/2004 | Matsumoto et al. |
| 6,780,871 B2 | 8/2004 | Glick et al. |
| 6,784,274 B2 | 8/2004 | Van Antwerp et al. |
| 6,790,178 B1 | 9/2004 | Mault et al. |
| 6,794,195 B2 | 9/2004 | Colvin, Jr. |
| 6,800,451 B2 | 10/2004 | Nikolaitchik et al. |
| 6,804,544 B2 | 10/2004 | Van Antwerp et al. |
| 6,804,558 B2 | 10/2004 | Haller et al. |
| 6,809,507 B2 | 10/2004 | Morgan et al. |
| 6,809,653 B1 | 10/2004 | Mann et al. |
| 6,810,290 B2 | 10/2004 | Lebel et al. |
| 6,810,309 B2 | 10/2004 | Sadler et al. |
| 6,811,533 B2 | 11/2004 | Lebel et al. |
| 6,811,534 B2 | 11/2004 | Bowman, IV et al. |
| 6,811,659 B2 | 11/2004 | Vachon |
| 6,812,031 B1 | 11/2004 | Carlsson |
| 6,813,519 B2 | 11/2004 | Lebel et al. |
| 6,816,742 B2 | 11/2004 | Kim et al. |
| 6,835,553 B2 | 12/2004 | Han et al. |
| RE38,681 E | 1/2005 | Kurnik et al. |
| 6,840,912 B2 | 1/2005 | Kloepfer et al. |
| 6,844,023 B2 | 1/2005 | Schulman et al. |
| 6,849,237 B2 | 2/2005 | Housefield et al. |
| 6,850,790 B2 | 2/2005 | Berner et al. |
| 6,852,104 B2 | 2/2005 | Blomquist |
| 6,852,500 B1 | 2/2005 | Hoss et al. |
| 6,852,694 B2 | 2/2005 | Van Antwerp et al. |

| | | | |
|---|---|---|---|
| 6,853,854 B1 | 2/2005 | Proniewicz et al. | |
| 6,856,928 B2 | 2/2005 | Harmon | |
| 6,858,403 B2 | 2/2005 | Han et al. | |
| 6,862,465 B2 | 3/2005 | Shults et al. | |
| 6,862,466 B2 | 3/2005 | Ackerman | |
| 6,872,200 B2 | 3/2005 | Mann et al. | |
| 6,873,268 B2 * | 3/2005 | Lebel et al. ............... 340/870.16 | |
| 6,878,112 B2 | 4/2005 | Linberg et al. | |
| 6,881,551 B2 | 4/2005 | Heller et al. | |
| 6,882,940 B2 | 4/2005 | Potts et al. | |
| 6,885,883 B2 | 4/2005 | Parris et al. | |
| 6,892,085 B2 | 5/2005 | McIvor et al. | |
| 6,895,263 B2 | 5/2005 | Shin et al. | |
| 6,895,265 B2 | 5/2005 | Silver et al. | |
| 6,899,683 B2 | 5/2005 | Mault et al. | |
| 6,899,684 B2 | 5/2005 | Mault et al. | |
| 6,902,207 B2 | 6/2005 | Lickliter | |
| 6,902,905 B2 | 6/2005 | Burson et al. | |
| 6,904,301 B2 | 6/2005 | Raskas | |
| 6,907,127 B1 | 6/2005 | Kravitz et al. | |
| 6,915,147 B2 | 7/2005 | Lebel et al. | |
| 6,918,874 B1 | 7/2005 | Hatch et al. | |
| 6,922,578 B2 | 7/2005 | Eppstein et al. | |
| RE38,775 E | 8/2005 | Kurnik et al. | |
| 6,923,764 B2 | 8/2005 | Aceti et al. | |
| 6,923,936 B2 | 8/2005 | Swanson et al. | |
| 6,927,246 B2 | 8/2005 | Noronha et al. | |
| 6,931,327 B2 | 8/2005 | Goode, Jr. et al. | |
| 6,936,006 B2 | 8/2005 | Sabra | |
| 6,936,029 B2 | 8/2005 | Mann et al. | |
| 6,940,403 B2 | 9/2005 | Kail, IV | |
| 6,940,590 B2 | 9/2005 | Colvin, Jr. et al. | |
| 6,941,163 B2 | 9/2005 | Ford et al. | |
| 6,950,708 B2 | 9/2005 | Bowman, IV et al. | |
| 6,952,603 B2 | 10/2005 | Gerber et al. | |
| 6,954,673 B2 | 10/2005 | Von Arx et al. | |
| 6,955,650 B2 | 10/2005 | Mault et al. | |
| 6,957,102 B2 | 10/2005 | Silver et al. | |
| 6,957,107 B2 | 10/2005 | Rogers et al. | |
| 6,958,705 B2 * | 10/2005 | Lebel et al. ............... 340/870.07 | |
| 6,968,294 B2 | 11/2005 | Gutta et al. | |
| 6,968,375 B1 | 11/2005 | Brown | |
| 6,971,274 B2 | 12/2005 | Olin | |
| 6,974,437 B2 * | 12/2005 | Lebel et al. ..................... 604/65 | |
| 6,978,182 B2 | 12/2005 | Mazar et al. | |
| 6,979,326 B2 | 12/2005 | Mann et al. | |
| 6,985,870 B2 | 1/2006 | Martucci et al. | |
| 6,990,366 B2 | 1/2006 | Say et al. | |
| 6,991,096 B2 | 1/2006 | Gottlieb et al. | |
| 6,997,907 B2 | 2/2006 | Safabash et al. | |
| 6,997,920 B2 | 2/2006 | Mann et al. | |
| 6,998,247 B2 | 2/2006 | Monfre et al. | |
| 6,999,810 B2 | 2/2006 | Berner et al. | |
| 7,003,336 B2 | 2/2006 | Holker et al. | |
| 7,003,340 B2 | 2/2006 | Say et al. | |
| 7,003,341 B2 | 2/2006 | Say et al. | |
| 7,004,901 B2 | 2/2006 | Fish | |
| 7,005,857 B2 | 2/2006 | Stiene et al. | |
| 7,009,511 B2 | 3/2006 | Mazar et al. | |
| 7,011,630 B2 | 3/2006 | Desai et al. | |
| 7,018,366 B2 | 3/2006 | Easter | |
| 7,018,568 B2 | 3/2006 | Tierney | |
| 7,020,508 B2 | 3/2006 | Stivoric et al. | |
| 7,022,072 B2 | 4/2006 | Fox et al. | |
| 7,024,236 B2 | 4/2006 | Ford et al. | |
| 7,024,245 B2 | 4/2006 | Lebel et al. | |
| 7,025,743 B2 | 4/2006 | Mann et al. | |
| 7,029,444 B2 | 4/2006 | Shin et al. | |
| 7,039,810 B1 | 5/2006 | Nichols | |
| 7,041,068 B2 | 5/2006 | Freeman et al. | |
| 7,041,468 B2 | 5/2006 | Drucker et al. | |
| 7,043,305 B2 | 5/2006 | KenKnight et al. | |
| 7,049,277 B2 | 5/2006 | Bagulla et al. | |
| 7,052,251 B2 | 5/2006 | Nason et al. | |
| 7,052,472 B1 | 5/2006 | Miller et al. | |
| 7,052,483 B2 | 5/2006 | Wojcik | |
| 7,056,302 B2 | 6/2006 | Douglas | |
| 7,058,453 B2 | 6/2006 | Nelson et al. | |
| 7,060,030 B2 | 6/2006 | Von Arx et al. | |
| 7,060,031 B2 | 6/2006 | Webb et al. | |
| 7,074,307 B2 | 7/2006 | Simpson et al. | |
| 7,081,195 B2 | 7/2006 | Simpson et al. | |
| 7,082,334 B2 | 7/2006 | Boute et al. | |
| 7,089,780 B2 | 8/2006 | Sunshine et al. | |
| 7,098,803 B2 | 8/2006 | Mann et al. | |
| 7,108,778 B2 | 9/2006 | Simpson et al. | |
| 7,110,803 B2 | 9/2006 | Shults et al. | |
| 7,113,821 B1 | 9/2006 | Sun et al. | |
| 7,114,502 B2 * | 10/2006 | Schulman et al. ............ 128/899 | |
| 7,125,382 B2 * | 10/2006 | Zhou et al. ..................... 600/365 | |
| 7,133,710 B2 | 11/2006 | Acosta et al. | |
| 7,134,999 B2 | 11/2006 | Brauker et al. | |
| 7,136,689 B2 | 11/2006 | Shults et al. | |
| 7,150,975 B2 | 12/2006 | Tamada et al. | |
| 7,155,112 B2 | 12/2006 | Uno et al. | |
| 7,155,290 B2 | 12/2006 | Von Arx et al. | |
| 7,163,511 B2 | 1/2007 | Conn et al. | |
| 7,171,274 B2 | 1/2007 | Starkweather et al. | |
| 7,183,068 B2 | 2/2007 | Burson et al. | |
| 7,183,102 B2 | 2/2007 | Monfre et al. | |
| 7,185,282 B1 * | 2/2007 | Naidoo et al. ................. 715/718 | |
| 7,189,341 B2 | 3/2007 | Li et al. | |
| 7,190,988 B2 | 3/2007 | Say et al. | |
| 7,192,450 B2 | 3/2007 | Brauker et al. | |
| 7,198,606 B2 | 4/2007 | Boecker et al. | |
| 7,203,549 B2 | 4/2007 | Schommer et al. | |
| 7,207,974 B2 | 4/2007 | Safabash et al. | |
| 7,221,977 B1 * | 5/2007 | Weaver et al. ................... 607/29 | |
| 7,226,442 B2 | 6/2007 | Sheppard et al. | |
| 7,226,978 B2 | 6/2007 | Tapsak et al. | |
| 7,228,163 B2 | 6/2007 | Ackerman | |
| 7,228,182 B2 | 6/2007 | Healy et al. | |
| 7,233,817 B2 | 6/2007 | Yen | |
| 7,237,712 B2 | 7/2007 | DeRocco et al. | |
| 7,241,266 B2 * | 7/2007 | Zhou et al. ..................... 600/365 | |
| 7,261,691 B1 | 8/2007 | Asomani | |
| 7,267,665 B2 | 9/2007 | Steil et al. | |
| 7,276,029 B2 | 10/2007 | Goode, Jr. et al. | |
| 7,278,983 B2 | 10/2007 | Ireland et al. | |
| 7,291,107 B2 | 11/2007 | Hellwig et al. | |
| 7,295,867 B2 | 11/2007 | Berner et al. | |
| 7,297,112 B2 * | 11/2007 | Zhou et al. ..................... 600/300 | |
| 7,299,082 B2 | 11/2007 | Feldman et al. | |
| 7,310,544 B2 | 12/2007 | Brister et al. | |
| 7,318,816 B2 | 1/2008 | Bobroff et al. | |
| 7,324,012 B2 | 1/2008 | Mann et al. | |
| 7,324,850 B2 | 1/2008 | Persen et al. | |
| 7,335,294 B2 | 2/2008 | Heller et al. | |
| 7,347,819 B2 | 3/2008 | Lebel et al. | |
| 7,354,420 B2 | 4/2008 | Steil et al. | |
| 7,364,592 B2 | 4/2008 | Carr-Brendel et al. | |
| 7,366,556 B2 | 4/2008 | Brister et al. | |
| 7,379,765 B2 | 5/2008 | Petisce et al. | |
| 7,384,397 B2 | 6/2008 | Zhang et al. | |
| 7,387,010 B2 | 6/2008 | Sunshine et al. | |
| 7,398,183 B2 | 7/2008 | Holland et al. | |
| 7,399,277 B2 | 7/2008 | Saidara et al. | |
| 7,402,153 B2 | 7/2008 | Steil et al. | |
| 7,419,573 B2 | 9/2008 | Gundel | |
| 7,424,318 B2 | 9/2008 | Brister et al. | |
| 7,460,898 B2 | 12/2008 | Brister et al. | |
| 7,467,003 B2 | 12/2008 | Brister et al. | |
| 7,471,972 B2 | 12/2008 | Rhodes et al. | |
| 7,494,465 B2 | 2/2009 | Brister et al. | |
| 7,497,827 B2 | 3/2009 | Brister et al. | |
| 7,506,046 B2 * | 3/2009 | Rhodes ........................... 709/224 | |
| 7,519,408 B2 | 4/2009 | Rasdal et al. | |
| 7,547,281 B2 | 6/2009 | Hayes et al. | |
| 7,565,197 B2 | 7/2009 | Haubrich et al. | |
| 7,569,030 B2 | 8/2009 | Lebel et al. | |
| 7,574,266 B2 | 8/2009 | Dudding et al. | |
| 7,583,990 B2 | 9/2009 | Goode, Jr. et al. | |
| 7,591,801 B2 | 9/2009 | Brauker et al. | |
| 7,599,726 B2 | 10/2009 | Goode, Jr. et al. | |
| 7,602,310 B2 | 10/2009 | Mann et al. | |
| 7,604,178 B2 | 10/2009 | Stewart | |
| 7,613,491 B2 | 11/2009 | Boock et al. | |
| 7,615,007 B2 | 11/2009 | Shults et al. | |

| | | |
|---|---|---|
| 7,618,369 B2 | 11/2009 | Hayter et al. |
| 7,632,228 B2 | 12/2009 | Brauker et al. |
| 7,637,868 B2 | 12/2009 | Saint et al. |
| 7,640,048 B2 | 12/2009 | Dobbles et al. |
| 7,651,596 B2 | 1/2010 | Petisce et al. |
| 7,654,956 B2 | 2/2010 | Brister et al. |
| 7,657,297 B2 | 2/2010 | Simpson et al. |
| 7,668,596 B2 | 2/2010 | Von Arx et al. |
| 7,711,402 B2 | 5/2010 | Shults et al. |
| 7,713,574 B2 | 5/2010 | Brister et al. |
| 7,715,893 B2 | 5/2010 | Kamath et al. |
| 7,771,352 B2 | 8/2010 | Shults et al. |
| 7,774,145 B2 | 8/2010 | Brauker et al. |
| 7,778,680 B2 | 8/2010 | Goode, Jr. et al. |
| 7,782,192 B2 | 8/2010 | Jeckelmann et al. |
| 7,783,333 B2 | 8/2010 | Brister et al. |
| 7,791,467 B2 | 9/2010 | Mazar et al. |
| 7,792,562 B2 | 9/2010 | Shults et al. |
| 7,813,809 B2 | 10/2010 | Strother et al. |
| 7,826,981 B2 | 11/2010 | Goode, Jr. et al. |
| 7,831,310 B2 | 11/2010 | Lebel et al. |
| 7,860,574 B2 | 12/2010 | Von Arx et al. |
| 7,882,611 B2 | 2/2011 | Shah et al. |
| 7,899,511 B2 | 3/2011 | Shults et al. |
| 7,905,833 B2 | 3/2011 | Brister et al. |
| 7,912,674 B2 | 3/2011 | Killoren Clark et al. |
| 7,914,450 B2 | 3/2011 | Goode, Jr. et al. |
| 7,916,013 B2 | 3/2011 | Stevenson |
| 7,955,258 B2 | 6/2011 | Goscha et al. |
| 7,970,448 B2 | 6/2011 | Shults et al. |
| 7,974,672 B2 | 7/2011 | Shults et al. |
| 7,999,674 B2 | 8/2011 | Kamen |
| 2001/0011224 A1 | 8/2001 | Brown |
| 2001/0016310 A1 | 8/2001 | Brown et al. |
| 2001/0016682 A1 | 8/2001 | Berner et al. |
| 2001/0016683 A1 | 8/2001 | Darrow et al. |
| 2001/0020124 A1 | 9/2001 | Tamada |
| 2001/0029340 A1 | 10/2001 | Mault et al. |
| 2001/0032278 A1 | 10/2001 | Brown et al. |
| 2001/0037060 A1 | 11/2001 | Thompson et al. |
| 2001/0037069 A1 | 11/2001 | Carlson et al. |
| 2001/0039504 A1 | 11/2001 | Linberg et al. |
| 2001/0041830 A1 | 11/2001 | Varalli et al. |
| 2001/0041831 A1* | 11/2001 | Starkweather et al. ....... 600/365 |
| 2001/0044581 A1 | 11/2001 | Mault |
| 2001/0044588 A1 | 11/2001 | Mault |
| 2001/0047125 A1 | 11/2001 | Quy |
| 2001/0049096 A1 | 12/2001 | Brown |
| 2001/0049470 A1 | 12/2001 | Mault et al. |
| 2002/0002326 A1 | 1/2002 | Causey, III et al. |
| 2002/0002328 A1 | 1/2002 | Tamada |
| 2002/0004640 A1 | 1/2002 | Conn et al. |
| 2002/0010414 A1 | 1/2002 | Coston et al. |
| 2002/0016530 A1 | 2/2002 | Brown |
| 2002/0016719 A1 | 2/2002 | Nemeth et al. |
| 2002/0019022 A1 | 2/2002 | Dunn et al. |
| 2002/0019586 A1 | 2/2002 | Teller et al. |
| 2002/0019748 A1 | 2/2002 | Brown |
| 2002/0026937 A1 | 3/2002 | Mault |
| 2002/0027164 A1 | 3/2002 | Mault et al. |
| 2002/0028995 A1 | 3/2002 | Mault |
| 2002/0040208 A1 | 4/2002 | Flaherty et al. |
| 2002/0042090 A1 | 4/2002 | Heller et al. |
| 2002/0047867 A1 | 4/2002 | Mault et al. |
| 2002/0053637 A1 | 5/2002 | Conn et al. |
| 2002/0062069 A1 | 5/2002 | Mault |
| 2002/0063060 A1 | 5/2002 | Gascoyne et al. |
| 2002/0068858 A1 | 6/2002 | Braig et al. |
| 2002/0072784 A1 | 6/2002 | Sheppard et al. |
| 2002/0072858 A1 | 6/2002 | Cheng |
| 2002/0077765 A1 | 6/2002 | Mault |
| 2002/0077766 A1 | 6/2002 | Mault |
| 2002/0081559 A1 | 6/2002 | Brown et al. |
| 2002/0083461 A1 | 6/2002 | Hutcheson et al. |
| 2002/0087056 A1 | 7/2002 | Aceti et al. |
| 2002/0091312 A1 | 7/2002 | Berner et al. |
| 2002/0103425 A1 | 8/2002 | Mault |
| 2002/0103499 A1 | 8/2002 | Perez et al. |
| 2002/0106709 A1 | 8/2002 | Potts et al. |
| 2002/0107433 A1 | 8/2002 | Mault |
| 2002/0107476 A1 | 8/2002 | Mann et al. |
| 2002/0109600 A1 | 8/2002 | Mault et al. |
| 2002/0119711 A1 | 8/2002 | Van Antwerp et al. |
| 2002/0124017 A1 | 9/2002 | Mault |
| 2002/0126036 A1 | 9/2002 | Flaherty et al. |
| 2002/0128594 A1 | 9/2002 | Das et al. |
| 2002/0130042 A1 | 9/2002 | Moerman et al. |
| 2002/0133378 A1 | 9/2002 | Mault et al. |
| 2002/0147135 A1 | 10/2002 | Schnell |
| 2002/0161286 A1 | 10/2002 | Gerber et al. |
| 2002/0161288 A1 | 10/2002 | Shin et al. |
| 2002/0169394 A1 | 11/2002 | Eppstein et al. |
| 2002/0169635 A1 | 11/2002 | Shillingburg |
| 2002/0177764 A1 | 11/2002 | Sohrab |
| 2002/0193679 A1 | 12/2002 | Malave et al. |
| 2003/0004403 A1 | 1/2003 | Drinan et al. |
| 2003/0023182 A1 | 1/2003 | Mault et al. |
| 2003/0023317 A1 | 1/2003 | Brauker et al. |
| 2003/0028089 A1 | 2/2003 | Galley et al. |
| 2003/0028120 A1 | 2/2003 | Mault et al. |
| 2003/0032077 A1 | 2/2003 | Itoh et al. |
| 2003/0032867 A1 | 2/2003 | Crothall et al. |
| 2003/0032868 A1 | 2/2003 | Graskov et al. |
| 2003/0032874 A1 | 2/2003 | Rhodes et al. |
| 2003/0040683 A1 | 2/2003 | Rule et al. |
| 2003/0042137 A1 | 3/2003 | Mao et al. |
| 2003/0050537 A1 | 3/2003 | Wessel |
| 2003/0050546 A1 | 3/2003 | Desai et al. |
| 2003/0065257 A1 | 4/2003 | Mault et al. |
| 2003/0065273 A1 | 4/2003 | Mault et al. |
| 2003/0065274 A1 | 4/2003 | Mault et al. |
| 2003/0065275 A1 | 4/2003 | Mault et al. |
| 2003/0065308 A1 | 4/2003 | Lebel et al. |
| 2003/0081370 A1 | 5/2003 | Haskell et al. |
| 2003/0100040 A1 | 5/2003 | Bonnecaze et al. |
| 2003/0100821 A1 | 5/2003 | Heller et al. |
| 2003/0105407 A1 | 6/2003 | Pearce et al. |
| 2003/0108976 A1 | 6/2003 | Braig et al. |
| 2003/0114897 A1 | 6/2003 | Von Arx et al. |
| 2003/0122021 A1 | 7/2003 | McConnell et al. |
| 2003/0125612 A1 | 7/2003 | Fox et al. |
| 2003/0130616 A1 | 7/2003 | Steil et al. |
| 2003/0134347 A1 | 7/2003 | Heller et al. |
| 2003/0135100 A1 | 7/2003 | Kim et al. |
| 2003/0135333 A1 | 7/2003 | Aceti et al. |
| 2003/0146841 A1 | 8/2003 | Koenig |
| 2003/0153820 A1 | 8/2003 | Berner et al. |
| 2003/0153821 A1 | 8/2003 | Berner et al. |
| 2003/0158472 A1 | 8/2003 | Sohrab |
| 2003/0158707 A1 | 8/2003 | Doi |
| 2003/0168338 A1 | 9/2003 | Gao et al. |
| 2003/0175806 A1 | 9/2003 | Rule et al. |
| 2003/0176183 A1 | 9/2003 | Drucker et al. |
| 2003/0176933 A1 | 9/2003 | Lebel et al. |
| 2003/0181851 A1 | 9/2003 | Mann et al. |
| 2003/0181852 A1 | 9/2003 | Mann et al. |
| 2003/0187338 A1 | 10/2003 | Say et al. |
| 2003/0187525 A1 | 10/2003 | Mann et al. |
| 2003/0191376 A1 | 10/2003 | Samuels et al. |
| 2003/0191431 A1 | 10/2003 | Mann et al. |
| 2003/0195403 A1 | 10/2003 | Berner et al. |
| 2003/0195462 A1 | 10/2003 | Mann et al. |
| 2003/0199790 A1 | 10/2003 | Boecker et al. |
| 2003/0199791 A1 | 10/2003 | Boecker et al. |
| 2003/0199903 A1 | 10/2003 | Boecker et al. |
| 2003/0203498 A1 | 10/2003 | Neel et al. |
| 2003/0208110 A1 | 11/2003 | Mault et al. |
| 2003/0208113 A1 | 11/2003 | Mault et al. |
| 2003/0208133 A1 | 11/2003 | Mault |
| 2003/0208409 A1 | 11/2003 | Mault |
| 2003/0212317 A1 | 11/2003 | Kovatchev et al. |
| 2003/0212364 A1 | 11/2003 | Mann et al. |
| 2003/0212379 A1 | 11/2003 | Bylund et al. |
| 2003/0217966 A1 | 11/2003 | Tapsak et al. |
| 2003/0226695 A1 | 12/2003 | Mault |
| 2003/0229514 A2 | 12/2003 | Brown |
| 2003/0232370 A1 | 12/2003 | Trifiro |
| 2003/0235817 A1 | 12/2003 | Bartkowiak et al. |

| | | |
|---|---|---|
| 2004/0010207 A1 | 1/2004 | Flaherty et al. |
| 2004/0011671 A1 | 1/2004 | Shults et al. |
| 2004/0018486 A1 | 1/2004 | Dunn et al. |
| 2004/0030226 A1 | 2/2004 | Quy |
| 2004/0039256 A1 | 2/2004 | Kawatahara et al. |
| 2004/0039298 A1 | 2/2004 | Abreu |
| 2004/0040840 A1 | 3/2004 | Mao et al. |
| 2004/0045879 A1 | 3/2004 | Shults et al. |
| 2004/0054263 A1 | 3/2004 | Moerman et al. |
| 2004/0059201 A1 | 3/2004 | Ginsberg |
| 2004/0064068 A1 | 4/2004 | DeNuzzio et al. |
| 2004/0069164 A1 | 4/2004 | Nakamura et al. |
| 2004/0072357 A1 | 4/2004 | Stiene et al. |
| 2004/0073095 A1 | 4/2004 | Causey, III et al. |
| 2004/0096959 A1 | 5/2004 | Stiene et al. |
| 2004/0106858 A1 | 6/2004 | Say et al. |
| 2004/0108226 A1 | 6/2004 | Polychronakos et al. |
| 2004/0122353 A1 | 6/2004 | Shahmirian et al. |
| 2004/0122489 A1 | 6/2004 | Mazar et al. |
| 2004/0122530 A1 | 6/2004 | Hansen et al. |
| 2004/0133164 A1 | 7/2004 | Funderburk et al. |
| 2004/0138588 A1 | 7/2004 | Saikley et al. |
| 2004/0146909 A1 | 7/2004 | Duong et al. |
| 2004/0152622 A1 | 8/2004 | Keith et al. |
| 2004/0152961 A1 | 8/2004 | Carlson et al. |
| 2004/0153585 A1 | 8/2004 | Kawatahara et al. |
| 2004/0162473 A1 | 8/2004 | Sohrab |
| 2004/0164961 A1 | 8/2004 | Bal et al. |
| 2004/0167383 A1 | 8/2004 | Kim et al. |
| 2004/0167464 A1 | 8/2004 | Ireland et al. |
| 2004/0167801 A1 | 8/2004 | Say et al. |
| 2004/0171921 A1* | 9/2004 | Say et al. ................ 600/347 |
| 2004/0172284 A1 | 9/2004 | Sullivan et al. |
| 2004/0176672 A1 | 9/2004 | Silver et al. |
| 2004/0176913 A1 | 9/2004 | Kawatahara et al. |
| 2004/0186362 A1 | 9/2004 | Brauker et al. |
| 2004/0186365 A1* | 9/2004 | Jin et al. .................. 600/365 |
| 2004/0193025 A1 | 9/2004 | Steil et al. |
| 2004/0193090 A1 | 9/2004 | Lebel et al. |
| 2004/0197846 A1 | 10/2004 | Hockersmith et al. |
| 2004/0199059 A1 | 10/2004 | Brauker et al. |
| 2004/0202576 A1 | 10/2004 | Aceti et al. |
| 2004/0204687 A1 | 10/2004 | Mogensen et al. |
| 2004/0208780 A1 | 10/2004 | Faries, Jr. et al. |
| 2004/0221057 A1 | 11/2004 | Darcey et al. |
| 2004/0225338 A1 | 11/2004 | Lebel et al. |
| 2004/0235446 A1 | 11/2004 | Flaherty et al. |
| 2004/0236200 A1 | 11/2004 | Say et al. |
| 2004/0248204 A1 | 12/2004 | Moerman |
| 2004/0249250 A1 | 12/2004 | McGee et al. |
| 2004/0249253 A1 | 12/2004 | Racchini et al. |
| 2004/0249254 A1 | 12/2004 | Racchini et al. |
| 2004/0249999 A1 | 12/2004 | Connolly et al. |
| 2004/0253736 A1 | 12/2004 | Stout et al. |
| 2004/0254429 A1 | 12/2004 | Yang |
| 2004/0254433 A1 | 12/2004 | Bandis et al. |
| 2004/0254434 A1 | 12/2004 | Goodnow et al. |
| 2004/0260363 A1 | 12/2004 | Von Arx et al. |
| 2004/0263354 A1 | 12/2004 | Mann et al. |
| 2004/0267300 A1 | 12/2004 | Mace |
| 2005/0003470 A1* | 1/2005 | Nelson et al. ................ 435/14 |
| 2005/0004439 A1 | 1/2005 | Shin et al. |
| 2005/0004494 A1 | 1/2005 | Perez et al. |
| 2005/0010087 A1* | 1/2005 | Banet et al. ................ 600/300 |
| 2005/0010269 A1 | 1/2005 | Lebel et al. |
| 2005/0016276 A1 | 1/2005 | Guan et al. |
| 2005/0027177 A1 | 2/2005 | Shin et al. |
| 2005/0027179 A1 | 2/2005 | Berner et al. |
| 2005/0027180 A1 | 2/2005 | Goode, Jr. et al. |
| 2005/0027181 A1 | 2/2005 | Goode, Jr. et al. |
| 2005/0027462 A1 | 2/2005 | Goode, Jr. et al. |
| 2005/0027463 A1 | 2/2005 | Goode, Jr. et al. |
| 2005/0031689 A1 | 2/2005 | Shults et al. |
| 2005/0033132 A1 | 2/2005 | Shults et al. |
| 2005/0038332 A1 | 2/2005 | Saidara et al. |
| 2005/0038680 A1 | 2/2005 | McMahon |
| 2005/0043598 A1 | 2/2005 | Goode, Jr. et al. |
| 2005/0043894 A1 | 2/2005 | Fernandez |
| 2005/0049473 A1 | 3/2005 | Desai et al. |
| 2005/0054909 A1 | 3/2005 | Petisce et al. |
| 2005/0065464 A1 | 3/2005 | Talbot et al. |
| 2005/0090607 A1 | 4/2005 | Tapsak et al. |
| 2005/0096511 A1 | 5/2005 | Fox et al. |
| 2005/0096512 A1 | 5/2005 | Fox et al. |
| 2005/0112169 A1 | 5/2005 | Brauker et al. |
| 2005/0112544 A1 | 5/2005 | Xe et al. |
| 2005/0113653 A1 | 5/2005 | Fox et al. |
| 2005/0113657 A1 | 5/2005 | Alarcon et al. |
| 2005/0113658 A1 | 5/2005 | Jacobson et al. |
| 2005/0113886 A1 | 5/2005 | Fischell et al. |
| 2005/0114068 A1 | 5/2005 | Chey et al. |
| 2005/0118726 A1 | 6/2005 | Schultz et al. |
| 2005/0121322 A1 | 6/2005 | Say et al. |
| 2005/0124873 A1 | 6/2005 | Shults et al. |
| 2005/0131346 A1 | 6/2005 | Douglas |
| 2005/0137471 A1 | 6/2005 | Haar et al. |
| 2005/0143635 A1 | 6/2005 | Kamath et al. |
| 2005/0143636 A1 | 6/2005 | Zhang et al. |
| 2005/0148003 A1 | 7/2005 | Keith et al. |
| 2005/0154271 A1 | 7/2005 | Rasdal et al. |
| 2005/0161346 A1 | 7/2005 | Simpson et al. |
| 2005/0171503 A1 | 8/2005 | Van Den Berghe et al. |
| 2005/0171513 A1 | 8/2005 | Mann et al. |
| 2005/0173245 A1 | 8/2005 | Feldman et al. |
| 2005/0176136 A1 | 8/2005 | Burd et al. |
| 2005/0177036 A1 | 8/2005 | Shults et al. |
| 2005/0177398 A1 | 8/2005 | Watanabe et al. |
| 2005/0181012 A1 | 8/2005 | Saint et al. |
| 2005/0182306 A1* | 8/2005 | Sloan .......................... 600/300 |
| 2005/0182451 A1 | 8/2005 | Griffin et al. |
| 2005/0187720 A1 | 8/2005 | Goode, Jr. et al. |
| 2005/0192494 A1 | 9/2005 | Ginsberg |
| 2005/0192557 A1 | 9/2005 | Brauker et al. |
| 2005/0195930 A1 | 9/2005 | Spital et al. |
| 2005/0199494 A1 | 9/2005 | Say et al. |
| 2005/0203360 A1 | 9/2005 | Brauker et al. |
| 2005/0203707 A1 | 9/2005 | Tsutsui et al. |
| 2005/0204134 A1 | 9/2005 | Von Arx et al. |
| 2005/0214892 A1 | 9/2005 | Kovatchev et al. |
| 2005/0215871 A1 | 9/2005 | Feldman et al. |
| 2005/0215872 A1 | 9/2005 | Berner et al. |
| 2005/0239154 A1 | 10/2005 | Feldman et al. |
| 2005/0239156 A1 | 10/2005 | Drucker et al. |
| 2005/0241957 A1 | 11/2005 | Mao et al. |
| 2005/0245795 A1 | 11/2005 | Goode, Jr. et al. |
| 2005/0245799 A1 | 11/2005 | Brauker et al. |
| 2005/0245839 A1 | 11/2005 | Stivoric et al. |
| 2005/0245904 A1 | 11/2005 | Estes et al. |
| 2005/0251033 A1 | 11/2005 | Scarantino et al. |
| 2005/0251083 A1 | 11/2005 | Carr-Brendel et al. |
| 2005/0261660 A1 | 11/2005 | Choi |
| 2005/0267780 A1 | 12/2005 | Ray et al. |
| 2005/0271546 A1 | 12/2005 | Gerber et al. |
| 2005/0271547 A1 | 12/2005 | Gerber et al. |
| 2005/0272640 A1 | 12/2005 | Doyle, III et al. |
| 2005/0272985 A1 | 12/2005 | Kotulla et al. |
| 2005/0277164 A1 | 12/2005 | Drucker et al. |
| 2005/0287620 A1 | 12/2005 | Heller et al. |
| 2006/0001538 A1 | 1/2006 | Kraft et al. |
| 2006/0001550 A1 | 1/2006 | Mann et al. |
| 2006/0001551 A1 | 1/2006 | Kraft et al. |
| 2006/0003398 A1 | 1/2006 | Heller et al. |
| 2006/0004270 A1 | 1/2006 | Bedard et al. |
| 2006/0004271 A1 | 1/2006 | Peyser et al. |
| 2006/0007017 A1 | 1/2006 | Mann et al. |
| 2006/0015020 A1 | 1/2006 | Neale et al. |
| 2006/0015024 A1 | 1/2006 | Brister et al. |
| 2006/0016700 A1 | 1/2006 | Brister et al. |
| 2006/0019327 A1 | 1/2006 | Brister et al. |
| 2006/0020186 A1 | 1/2006 | Brister et al. |
| 2006/0020187 A1 | 1/2006 | Brister et al. |
| 2006/0020188 A1 | 1/2006 | Kamath et al. |
| 2006/0020189 A1 | 1/2006 | Brister et al. |
| 2006/0020190 A1 | 1/2006 | Kamath et al. |
| 2006/0020191 A1 | 1/2006 | Brister et al. |
| 2006/0020192 A1 | 1/2006 | Brister et al. |
| 2006/0025663 A1 | 2/2006 | Talbot et al. |
| 2006/0029177 A1 | 2/2006 | Cranford, Jr. et al. |

| | | |
|---|---|---|
| 2006/0031094 A1 | 2/2006 | Cohen et al. |
| 2006/0036139 A1 | 2/2006 | Brister et al. |
| 2006/0036140 A1 | 2/2006 | Brister et al. |
| 2006/0036141 A1 | 2/2006 | Kamath et al. |
| 2006/0036142 A1 | 2/2006 | Brister et al. |
| 2006/0036143 A1 | 2/2006 | Brister et al. |
| 2006/0036144 A1 | 2/2006 | Brister et al. |
| 2006/0036145 A1 | 2/2006 | Brister et al. |
| 2006/0036187 A1 | 2/2006 | Vos et al. |
| 2006/0040402 A1 | 2/2006 | Brauker et al. |
| 2006/0052679 A1 | 3/2006 | Kotulla et al. |
| 2006/0058602 A1 | 3/2006 | Kwiatkowski et al. |
| 2006/0063218 A1 | 3/2006 | Bartkowiak et al. |
| 2006/0074564 A1 | 4/2006 | Bartkowiak et al. |
| 2006/0142651 A1 | 6/2006 | Brister et al. |
| 2006/0155180 A1 | 7/2006 | Brister et al. |
| 2006/0166629 A1 | 7/2006 | Reggiardo |
| 2006/0173260 A1 | 8/2006 | Gaoni et al. |
| 2006/0173406 A1 | 8/2006 | Hayes et al. |
| 2006/0173444 A1 | 8/2006 | Choy et al. |
| 2006/0183985 A1 | 8/2006 | Brister et al. |
| 2006/0189863 A1 | 8/2006 | Peyser et al. |
| 2006/0195029 A1 | 8/2006 | Shults et al. |
| 2006/0200112 A1 | 9/2006 | Paul |
| 2006/0202805 A1 | 9/2006 | Schulman et al. |
| 2006/0222566 A1 | 10/2006 | Brauker et al. |
| 2006/0224109 A1 | 10/2006 | Steil et al. |
| 2006/0224141 A1 | 10/2006 | Rush et al. |
| 2006/0226985 A1* | 10/2006 | Goodnow et al. .......... 340/572.1 |
| 2006/0229512 A1 | 10/2006 | Petisce et al. |
| 2006/0247508 A1 | 11/2006 | Fennell |
| 2006/0247710 A1 | 11/2006 | Goetz et al. |
| 2006/0247985 A1 | 11/2006 | Liamos et al. |
| 2006/0258918 A1 | 11/2006 | Burd et al. |
| 2006/0258929 A1 | 11/2006 | Goode, Jr. et al. |
| 2006/0263763 A1 | 11/2006 | Simpson et al. |
| 2006/0272652 A1 | 12/2006 | Stocker et al. |
| 2006/0287691 A1 | 12/2006 | Drew |
| 2006/0290496 A1 | 12/2006 | Peeters et al. |
| 2007/0016381 A1 | 1/2007 | Kamath et al. |
| 2007/0027381 A1 | 2/2007 | Stafford |
| 2007/0033074 A1 | 2/2007 | Nitzan et al. |
| 2007/0055799 A1 | 3/2007 | Koehler et al. |
| 2007/0060814 A1 | 3/2007 | Stafford |
| 2007/0066873 A1 | 3/2007 | Kamath et al. |
| 2007/0071681 A1 | 3/2007 | Gadkar et al. |
| 2007/0073129 A1 | 3/2007 | Shah et al. |
| 2007/0078320 A1 | 4/2007 | Stafford |
| 2007/0078321 A1 | 4/2007 | Mazza et al. |
| 2007/0078322 A1 | 4/2007 | Stafford |
| 2007/0078323 A1 | 4/2007 | Reggiardo et al. |
| 2007/0106135 A1 | 5/2007 | Sloan et al. |
| 2007/0124002 A1 | 5/2007 | Estes et al. |
| 2007/0149873 A1 | 6/2007 | Say et al. |
| 2007/0149874 A1 | 6/2007 | Say et al. |
| 2007/0149875 A1 | 6/2007 | Ouyang et al. |
| 2007/0151869 A1 | 7/2007 | Heller et al. |
| 2007/0156033 A1 | 7/2007 | Causey, III et al. |
| 2007/0161879 A1 | 7/2007 | Say et al. |
| 2007/0161880 A1 | 7/2007 | Say et al. |
| 2007/0163880 A1 | 7/2007 | Woo et al. |
| 2007/0168224 A1 | 7/2007 | Letzt et al. |
| 2007/0173706 A1 | 7/2007 | Neinast et al. |
| 2007/0173761 A1 | 7/2007 | Kanderian et al. |
| 2007/0179349 A1 | 8/2007 | Hoyme et al. |
| 2007/0179352 A1 | 8/2007 | Randlov et al. |
| 2007/0179370 A1 | 8/2007 | Say et al. |
| 2007/0179372 A1 | 8/2007 | Say et al. |
| 2007/0191699 A1 | 8/2007 | Say et al. |
| 2007/0191700 A1 | 8/2007 | Say et al. |
| 2007/0191701 A1 | 8/2007 | Feldman et al. |
| 2007/0203407 A1 | 8/2007 | Hoss et al. |
| 2007/0203408 A1 | 8/2007 | Say et al. |
| 2007/0203410 A1 | 8/2007 | Say et al. |
| 2007/0203411 A1 | 8/2007 | Say et al. |
| 2007/0203966 A1 | 8/2007 | Brauker et al. |
| 2007/0208247 A1 | 9/2007 | Say et al. |
| 2007/0213610 A1 | 9/2007 | Say et al. |
| 2007/0213657 A1 | 9/2007 | Jennewine et al. |
| 2007/0215491 A1 | 9/2007 | Heller et al. |
| 2007/0218097 A1 | 9/2007 | Heller et al. |
| 2007/0232877 A1 | 10/2007 | He |
| 2007/0232880 A1 | 10/2007 | Siddiqui et al. |
| 2007/0235331 A1 | 10/2007 | Simpson et al. |
| 2007/0244380 A1 | 10/2007 | Say et al. |
| 2007/0244383 A1 | 10/2007 | Talbot et al. |
| 2007/0249919 A1 | 10/2007 | Say et al. |
| 2007/0249920 A1 | 10/2007 | Say et al. |
| 2007/0249922 A1 | 10/2007 | Peyser et al. |
| 2007/0253021 A1 | 11/2007 | Mehta et al. |
| 2007/0255531 A1 | 11/2007 | Drew |
| 2007/0258395 A1 | 11/2007 | Jollota et al. |
| 2007/0270672 A1 | 11/2007 | Hayter |
| 2007/0285238 A1 | 12/2007 | Batra |
| 2007/0299617 A1 | 12/2007 | Willis |
| 2008/0004515 A1 | 1/2008 | Jennewine et al. |
| 2008/0004601 A1 | 1/2008 | Jennewine et al. |
| 2008/0009692 A1 | 1/2008 | Stafford |
| 2008/0017522 A1 | 1/2008 | Heller et al. |
| 2008/0018433 A1 | 1/2008 | Pitt-Pladdy |
| 2008/0021666 A1 | 1/2008 | Goode, Jr. et al. |
| 2008/0029391 A1 | 2/2008 | Mao et al. |
| 2008/0030369 A1 | 2/2008 | Mann et al. |
| 2008/0033254 A1 | 2/2008 | Kamath et al. |
| 2008/0039702 A1 | 2/2008 | Hayter et al. |
| 2008/0045824 A1 | 2/2008 | Tapsak et al. |
| 2008/0064943 A1 | 3/2008 | Talbot et al. |
| 2008/0071156 A1 | 3/2008 | Brister et al. |
| 2008/0071157 A1 | 3/2008 | McGarraugh et al. |
| 2008/0071158 A1 | 3/2008 | McGarraugh et al. |
| 2008/0071328 A1 | 3/2008 | Haubrich et al. |
| 2008/0081977 A1 | 4/2008 | Hayter et al. |
| 2008/0083617 A1 | 4/2008 | Simpson et al. |
| 2008/0086042 A1 | 4/2008 | Brister et al. |
| 2008/0086044 A1 | 4/2008 | Brister et al. |
| 2008/0086273 A1 | 4/2008 | Shults et al. |
| 2008/0097289 A1 | 4/2008 | Steil et al. |
| 2008/0108942 A1 | 5/2008 | Brister et al. |
| 2008/0119705 A1 | 5/2008 | Patel et al. |
| 2008/0139910 A1 | 6/2008 | Mastrototaro et al. |
| 2008/0154513 A1 | 6/2008 | Kovatchev et al. |
| 2008/0167543 A1 | 7/2008 | Say et al. |
| 2008/0167572 A1 | 7/2008 | Stivoric et al. |
| 2008/0172205 A1 | 7/2008 | Breton et al. |
| 2008/0183060 A1 | 7/2008 | Steil et al. |
| 2008/0183061 A1 | 7/2008 | Goode et al. |
| 2008/0183399 A1 | 7/2008 | Goode et al. |
| 2008/0188731 A1 | 8/2008 | Brister et al. |
| 2008/0188796 A1 | 8/2008 | Steil et al. |
| 2008/0189051 A1 | 8/2008 | Goode et al. |
| 2008/0194935 A1 | 8/2008 | Brister et al. |
| 2008/0194936 A1 | 8/2008 | Goode et al. |
| 2008/0194937 A1 | 8/2008 | Goode et al. |
| 2008/0194938 A1 | 8/2008 | Brister et al. |
| 2008/0195232 A1 | 8/2008 | Carr-Brendel et al. |
| 2008/0195967 A1 | 8/2008 | Goode et al. |
| 2008/0197024 A1 | 8/2008 | Simpson et al. |
| 2008/0200788 A1 | 8/2008 | Brister et al. |
| 2008/0200789 A1 | 8/2008 | Brister et al. |
| 2008/0200791 A1 | 8/2008 | Simpson et al. |
| 2008/0208025 A1 | 8/2008 | Shults et al. |
| 2008/0208113 A1 | 8/2008 | Damiano et al. |
| 2008/0214915 A1 | 9/2008 | Brister et al. |
| 2008/0214918 A1 | 9/2008 | Brister et al. |
| 2008/0228051 A1 | 9/2008 | Shults et al. |
| 2008/0228054 A1 | 9/2008 | Shults et al. |
| 2008/0235469 A1 | 9/2008 | Drew |
| 2008/0242961 A1 | 10/2008 | Brister et al. |
| 2008/0255434 A1 | 10/2008 | Hayter et al. |
| 2008/0255437 A1 | 10/2008 | Hayter |
| 2008/0255438 A1 | 10/2008 | Saidara et al. |
| 2008/0255808 A1 | 10/2008 | Hayter |
| 2008/0256048 A1 | 10/2008 | Hayter |
| 2008/0262469 A1 | 10/2008 | Brister et al. |
| 2008/0275313 A1 | 11/2008 | Brister et al. |
| 2008/0287761 A1 | 11/2008 | Hayter |
| 2008/0287762 A1 | 11/2008 | Hayter |
| 2008/0287763 A1 | 11/2008 | Hayter |

| | | | |
|---|---|---|---|
| 2008/0287764 A1 | 11/2008 | Rasdal et al. |
| 2008/0287765 A1 | 11/2008 | Rasdal et al. |
| 2008/0287766 A1 | 11/2008 | Rasdal et al. |
| 2008/0288180 A1 | 11/2008 | Hayter |
| 2008/0288204 A1 | 11/2008 | Hayter et al. |
| 2008/0296155 A1 | 12/2008 | Shults et al. |
| 2008/0300919 A1 | 12/2008 | Charlton et al. |
| 2008/0300920 A1 | 12/2008 | Brown et al. |
| 2008/0301158 A1 | 12/2008 | Brown et al. |
| 2008/0301665 A1 | 12/2008 | Charlton et al. |
| 2008/0306368 A1 | 12/2008 | Goode et al. |
| 2008/0306434 A1 | 12/2008 | Dobbles et al. |
| 2008/0306435 A1 | 12/2008 | Kamath et al. |
| 2008/0306444 A1 | 12/2008 | Brister et al. |
| 2008/0312518 A1 | 12/2008 | Jina et al. |
| 2008/0312841 A1 | 12/2008 | Hayter |
| 2008/0312842 A1 | 12/2008 | Hayter |
| 2008/0312844 A1 | 12/2008 | Hayter et al. |
| 2008/0312845 A1 | 12/2008 | Hayter et al. |
| 2009/0005665 A1 | 1/2009 | Hayter et al. |
| 2009/0005666 A1 | 1/2009 | Shin et al. |
| 2009/0006034 A1 | 1/2009 | Hayter et al. |
| 2009/0012379 A1 | 1/2009 | Goode et al. |
| 2009/0018424 A1 | 1/2009 | Kamath et al. |
| 2009/0030294 A1 | 1/2009 | Petisce et al. |
| 2009/0033482 A1 | 2/2009 | Hayter et al. |
| 2009/0036747 A1 | 2/2009 | Hayter et al. |
| 2009/0036758 A1 | 2/2009 | Brauker et al. |
| 2009/0036760 A1 | 2/2009 | Hayter |
| 2009/0036763 A1 | 2/2009 | Brauker et al. |
| 2009/0043181 A1 | 2/2009 | Brauker et al. |
| 2009/0043182 A1 | 2/2009 | Brauker et al. |
| 2009/0043525 A1 | 2/2009 | Brauker et al. |
| 2009/0043541 A1 | 2/2009 | Brauker et al. |
| 2009/0043542 A1 | 2/2009 | Brauker et al. |
| 2009/0045055 A1 | 2/2009 | Rhodes et al. |
| 2009/0055149 A1 | 2/2009 | Hayter et al. |
| 2009/0062633 A1 | 3/2009 | Brauker et al. |
| 2009/0062635 A1 | 3/2009 | Brauker et al. |
| 2009/0062767 A1 | 3/2009 | VanAntwerp et al. |
| 2009/0063402 A1 | 3/2009 | Hayter |
| 2009/0076356 A1 | 3/2009 | Simpson et al. |
| 2009/0076360 A1 | 3/2009 | Brister et al. |
| 2009/0076361 A1 | 3/2009 | Kamath et al. |
| 2009/0085768 A1 | 4/2009 | Patel et al. |
| 2009/0099436 A1 | 4/2009 | Brister et al. |
| 2009/0105554 A1 | 4/2009 | Stahmann et al. |
| 2009/0105636 A1 | 4/2009 | Hayter et al. |
| 2009/0112478 A1 | 4/2009 | Mueller, Jr. et al. |
| 2009/0124877 A1 | 5/2009 | Goode et al. |
| 2009/0124878 A1 | 5/2009 | Goode et al. |
| 2009/0124879 A1 | 5/2009 | Brister et al. |
| 2009/0124964 A1 | 5/2009 | Leach et al. |
| 2009/0131768 A1 | 5/2009 | Simpson et al. |
| 2009/0131769 A1 | 5/2009 | Leach et al. |
| 2009/0131776 A1 | 5/2009 | Simpson et al. |
| 2009/0131777 A1 | 5/2009 | Simpson et al. |
| 2009/0137886 A1 | 5/2009 | Shariati et al. |
| 2009/0137887 A1 | 5/2009 | Shariati et al. |
| 2009/0143659 A1 | 6/2009 | Li et al. |
| 2009/0143660 A1 | 6/2009 | Brister et al. |
| 2009/0149717 A1 | 6/2009 | Brauer et al. |
| 2009/0150186 A1 | 6/2009 | Cohen et al. |
| 2009/0156919 A1 | 6/2009 | Brister et al. |
| 2009/0156924 A1 | 6/2009 | Shariati et al. |
| 2009/0163790 A1 | 6/2009 | Brister et al. |
| 2009/0163791 A1 | 6/2009 | Brister et al. |
| 2009/0164190 A1 | 6/2009 | Hayter |
| 2009/0164239 A1 | 6/2009 | Hayter et al. |
| 2009/0164251 A1 | 6/2009 | Hayter |
| 2009/0178459 A1 | 7/2009 | Li et al. |
| 2009/0182217 A1 | 7/2009 | Li et al. |
| 2009/0189738 A1 | 7/2009 | Hermle |
| 2009/0192366 A1 | 7/2009 | Mensinger et al. |
| 2009/0192380 A1 | 7/2009 | Shariati et al. |
| 2009/0192722 A1 | 7/2009 | Shariati et al. |
| 2009/0192724 A1 | 7/2009 | Brauker et al. |
| 2009/0192745 A1 | 7/2009 | Kamath et al. |
| 2009/0192751 A1 | 7/2009 | Kamath et al. |
| 2009/0198118 A1 | 8/2009 | Hayter et al. |
| 2009/0203981 A1 | 8/2009 | Brauker et al. |
| 2009/0204341 A1 | 8/2009 | Brauker et al. |
| 2009/0216103 A1 | 8/2009 | Brister et al. |
| 2009/0234200 A1 | 9/2009 | Husheer |
| 2009/0240120 A1 | 9/2009 | Mensinger et al. |
| 2009/0240128 A1 | 9/2009 | Mensinger et al. |
| 2009/0240193 A1 | 9/2009 | Mensinger et al. |
| 2009/0242399 A1 | 10/2009 | Kamath et al. |
| 2009/0242425 A1 | 10/2009 | Kamath et al. |
| 2009/0247855 A1 | 10/2009 | Boock et al. |
| 2009/0247856 A1 | 10/2009 | Boock et al. |
| 2009/0247931 A1 | 10/2009 | Damgaard-Sorensen |
| 2009/0267765 A1 | 10/2009 | Greene et al. |
| 2009/0287073 A1 | 11/2009 | Boock et al. |
| 2009/0287074 A1 | 11/2009 | Shults et al. |
| 2009/0289796 A1 | 11/2009 | Blumberg |
| 2009/0299155 A1 | 12/2009 | Yang et al. |
| 2009/0299156 A1 | 12/2009 | Simpson et al. |
| 2009/0299162 A1 | 12/2009 | Brauker et al. |
| 2009/0299276 A1 | 12/2009 | Brauker et al. |
| 2010/0010324 A1 | 1/2010 | Brauker et al. |
| 2010/0010331 A1 | 1/2010 | Brauker et al. |
| 2010/0010332 A1 | 1/2010 | Brauker et al. |
| 2010/0016687 A1 | 1/2010 | Brauker et al. |
| 2010/0016698 A1 | 1/2010 | Rasdal et al. |
| 2010/0022855 A1 | 1/2010 | Brauker et al. |
| 2010/0030038 A1 | 2/2010 | Brauker et al. |
| 2010/0030053 A1 | 2/2010 | Goode, Jr. et al. |
| 2010/0030484 A1 | 2/2010 | Brauker et al. |
| 2010/0030485 A1 | 2/2010 | Brauker et al. |
| 2010/0036215 A1 | 2/2010 | Goode, Jr. et al. |
| 2010/0036216 A1 | 2/2010 | Goode, Jr. et al. |
| 2010/0036222 A1 | 2/2010 | Goode, Jr. et al. |
| 2010/0036223 A1 | 2/2010 | Goode, Jr. et al. |
| 2010/0036225 A1 | 2/2010 | Goode, Jr. et al. |
| 2010/0041971 A1 | 2/2010 | Goode, Jr. et al. |
| 2010/0045465 A1 | 2/2010 | Brauker et al. |
| 2010/0049024 A1 | 2/2010 | Saint et al. |
| 2010/0057040 A1 | 3/2010 | Hayter |
| 2010/0057041 A1 | 3/2010 | Hayter |
| 2010/0057042 A1 | 3/2010 | Hayter |
| 2010/0057044 A1 | 3/2010 | Hayter |
| 2010/0057057 A1 | 3/2010 | Hayter et al. |
| 2010/0063373 A1 | 3/2010 | Kamath et al. |
| 2010/0076283 A1 | 3/2010 | Simpson et al. |
| 2010/0081908 A1 | 4/2010 | Dobbles et al. |
| 2010/0081910 A1 | 4/2010 | Brister et al. |
| 2010/0087724 A1 | 4/2010 | Brauker et al. |
| 2010/0096259 A1 | 4/2010 | Zhang et al. |
| 2010/0099970 A1 | 4/2010 | Shults et al. |
| 2010/0099971 A1 | 4/2010 | Shults et al. |
| 2010/0119693 A1 | 5/2010 | Tapsak et al. |
| 2010/0121169 A1 | 5/2010 | Petisce et al. |
| 2010/0190435 A1 | 7/2010 | Cook et al. |
| 2011/0004276 A1 | 1/2011 | Blair et al. |
| 2011/0152637 A1 | 6/2011 | Kateraas et al. |

FOREIGN PATENT DOCUMENTS

| | | |
|---|---|---|
| CA | 2396613 | 3/2008 |
| CA | 2413148 | 8/2010 |
| DE | 2903216 | 8/1979 |
| DE | 227029 | 9/1985 |
| DE | 3934299 | 10/1990 |
| DE | 4234553 | 1/1995 |
| DE | 4401400 | 7/1995 |
| EP | 0010375 | 4/1980 |
| EP | 1579690 | 11/1980 |
| EP | 0026995 | 4/1981 |
| EP | 0048090 | 3/1982 |
| EP | 0078636 | 5/1983 |
| EP | 0080304 | 6/1983 |
| EP | 0096228 | 12/1983 |
| EP | 0096288 | 12/1983 |
| EP | 0098592 | 1/1984 |
| EP | 0125139 | 11/1984 |
| EP | 0127958 | 12/1984 |
| EP | 0136362 | 4/1985 |
| EP | 0170375 | 2/1986 |

| | | | | | |
|---|---|---|---|---|---|
| EP | 0177743 | 4/1986 | JP | 2-310457 | 12/1990 |
| EP | 0184909 | 6/1986 | JP | 3-026956 | 2/1991 |
| EP | 0206218 | 12/1986 | JP | 3-028752 | 2/1991 |
| EP | 0230472 | 8/1987 | JP | 3-202764 | 9/1991 |
| EP | 0241309 | 10/1987 | JP | 5-072171 | 3/1993 |
| EP | 0245073 | 11/1987 | JP | 5-196595 | 8/1993 |
| EP | 0255291 | 2/1988 | JP | 6-190050 | 7/1994 |
| EP | 0278647 | 8/1988 | JP | 7-055757 | 3/1995 |
| EP | 0320109 | 6/1989 | JP | 7-072585 | 3/1995 |
| EP | 0353328 | 2/1990 | JP | 8-154903 | 6/1996 |
| EP | 0359831 | 3/1990 | JP | 8-285814 | 11/1996 |
| EP | 0368209 | 5/1990 | JP | 8-285815 | 11/1996 |
| EP | 0368290 | 5/1990 | JP | 9-021778 | 1/1997 |
| EP | 0390390 | 10/1990 | JP | 9-101280 | 4/1997 |
| EP | 0396788 | 11/1990 | JP | 9-285459 | 11/1997 |
| EP | 0400918 | 12/1990 | JP | 10-170471 | 6/1998 |
| EP | 0453283 | 10/1991 | JP | 2000-000231 | 1/2000 |
| EP | 0470290 | 2/1992 | JP | 2000-116628 | 4/2000 |
| EP | 0504835 | 9/1992 | SU | 1281988 | 1/1987 |
| EP | 0286118 | 1/1995 | WO | WO-85/05119 | 11/1985 |
| EP | 0653718 | 5/1995 | WO | WO-86/00513 | 1/1986 |
| EP | 0724859 | 8/1996 | WO | WO-87/00513 | 1/1987 |
| EP | 0800082 | 10/1997 | WO | WO-87/06040 | 10/1987 |
| EP | 0880936 | 12/1998 | WO | WO-89/02246 | 3/1989 |
| EP | 0970655 | 1/2000 | WO | WO-89/05119 | 6/1989 |
| EP | 0678308 | 5/2000 | WO | WO-89/08713 | 9/1989 |
| EP | 1034734 | 9/2000 | WO | WO-90/00367 | 1/1990 |
| EP | 1048264 | 11/2000 | WO | WO-90/05300 | 5/1990 |
| EP | 1292218 | 3/2003 | WO | WO-90/05910 | 5/1990 |
| EP | 1077634 | 7/2003 | WO | WO-91/01680 | 2/1991 |
| EP | 1445746 | 8/2004 | WO | WO-91/04704 | 4/1991 |
| EP | 1666091 | 6/2006 | WO | WO-91/15993 | 10/1991 |
| EP | 1703697 | 9/2006 | WO | WO-92/01947 | 2/1992 |
| EP | 1704893 | 9/2006 | WO | WO-92/13271 | 8/1992 |
| EP | 1897487 | 11/2009 | WO | WO-94/20602 | 9/1994 |
| EP | 1897492 | 11/2009 | WO | WO-94/27140 | 11/1994 |
| EP | 2113864 | 11/2009 | WO | WO-95/06240 | 3/1995 |
| EP | 1897488 | 12/2009 | WO | WO-96/07908 | 3/1996 |
| EP | 1681992 | 4/2010 | WO | WO-96/25089 | 8/1996 |
| EP | 1448489 | 8/2010 | WO | WO-96/30431 | 10/1996 |
| EP | 1971396 | 8/2010 | WO | WO-96/35370 | 11/1996 |
| EP | 2201969 | 3/2011 | WO | WO-97/02847 | 1/1997 |
| GB | 1394171 | 5/1975 | WO | WO-97/19344 | 5/1997 |
| GB | 1579690 | 11/1980 | WO | WO-97/20207 | 6/1997 |
| GB | 1599241 | 9/1981 | WO | WO-97/33513 | 9/1997 |
| GB | 2073891 | 10/1981 | WO | WO-97/41421 | 11/1997 |
| GB | 2154003 | 8/1985 | WO | WO-97/42882 | 11/1997 |
| GB | 2194892 | 3/1988 | WO | WO-97/42883 | 11/1997 |
| GB | 2204408 | 11/1988 | WO | WO-97/42886 | 11/1997 |
| GB | 2225637 | 6/1990 | WO | WO-97/42888 | 11/1997 |
| GB | 2254436 | 10/1992 | WO | WO-97/43962 | 11/1997 |
| JP | 54-041191 | 4/1979 | WO | WO-97/46868 | 12/1997 |
| JP | 55-010581 | 1/1980 | WO | WO-98/09167 | 3/1998 |
| JP | 55-010583 | 1/1980 | WO | WO-98/24366 | 6/1998 |
| JP | 55-010584 | 1/1980 | WO | WO-98/35053 | 8/1998 |
| JP | 55-012406 | 1/1980 | WO | WO-98/52045 | 11/1998 |
| JP | 56-163447 | 12/1981 | WO | WO-98/52293 | 11/1998 |
| JP | 57-070448 | 4/1982 | WO | WO-99/05966 | 2/1999 |
| JP | 60-173457 | 9/1985 | WO | WO-99/32883 | 7/1999 |
| JP | 60-173458 | 9/1985 | WO | WO-99/56613 | 11/1999 |
| JP | 60-173459 | 9/1985 | WO | WO-00/13580 | 3/2000 |
| JP | 60-210243 | 10/1985 | WO | WO-00/18294 | 4/2000 |
| JP | 61-090050 | 5/1986 | WO | WO-00/19887 | 4/2000 |
| JP | 62-085855 | 4/1987 | WO | WO-00/20626 | 4/2000 |
| JP | 62-114747 | 5/1987 | WO | WO-00/33065 | 6/2000 |
| JP | 63-058149 | 3/1988 | WO | WO-00/49940 | 8/2000 |
| JP | 63-128252 | 5/1988 | WO | WO-00/59370 | 10/2000 |
| JP | 63-139246 | 6/1988 | WO | WO-00/62664 | 10/2000 |
| JP | 63-294799 | 12/1988 | WO | WO-00/62665 | 10/2000 |
| JP | 63-317757 | 12/1988 | WO | WO-00/78210 | 12/2000 |
| JP | 63-317758 | 12/1988 | WO | WO-00/78992 | 12/2000 |
| JP | 1-114746 | 5/1989 | WO | WO-01/24038 | 4/2001 |
| JP | 1-114747 | 5/1989 | WO | WO-01/33216 | 5/2001 |
| JP | 1-124060 | 5/1989 | WO | WO-01/52727 | 7/2001 |
| JP | 1-134244 | 5/1989 | WO | WO-01/52935 | 7/2001 |
| JP | 1-156658 | 6/1989 | WO | WO-01/54753 | 8/2001 |
| JP | 2-062958 | 3/1990 | WO | WO-01/57238 | 8/2001 |
| JP | 2-120655 | 5/1990 | WO | WO-01/57239 | 8/2001 |
| JP | 2-287145 | 11/1990 | WO | WO-01/67009 | 9/2001 |

| | | |
|---|---|---|
| WO | WO-02/13686 | 2/2002 |
| WO | WO-02/16905 | 2/2002 |
| WO | WO-02/17210 | 2/2002 |
| WO | WO-02/058537 | 8/2002 |
| WO | WO-02/078512 | 10/2002 |
| WO | WO-03/036583 | 5/2003 |
| WO | WO-03/076893 | 9/2003 |
| WO | WO-03/082091 | 10/2003 |
| WO | WO-03/085372 | 10/2003 |
| WO | WO-2004/061420 | 7/2004 |
| WO | WO-2005/041766 | 5/2005 |
| WO | WO-2005/045744 | 5/2005 |
| WO | WO-2005/089103 | 9/2005 |
| WO | WO-2006/024671 | 3/2006 |
| WO | WO-2006/032653 | 3/2006 |
| WO | WO-2006/037109 | 4/2006 |
| WO | WO-2006/079114 | 7/2006 |
| WO | WO-2006/118947 | 11/2006 |
| WO | WO-2006/119084 | 11/2006 |
| WO | WO-2006/124099 | 11/2006 |
| WO | WO-2007/002189 | 1/2007 |
| WO | WO-2007/016399 | 2/2007 |
| WO | WO-2007/027381 | 3/2007 |
| WO | WO-2007/027788 | 3/2007 |
| WO | WO-2007/041069 | 4/2007 |
| WO | WO-2007/041070 | 4/2007 |
| WO | WO-2007/041072 | 4/2007 |
| WO | WO-2007/041248 | 4/2007 |
| WO | WO-2007/053832 | 5/2007 |
| WO | WO-2007/056638 | 5/2007 |
| WO | WO-2007/101223 | 9/2007 |
| WO | WO-2007/101260 | 9/2007 |
| WO | WO-2007/120363 | 10/2007 |
| WO | WO-2007/126444 | 11/2007 |
| WO | WO-2007/143225 | 12/2007 |
| WO | WO-2008/003003 | 1/2008 |
| WO | WO-2008/005780 | 1/2008 |
| WO | WO-2008/021913 | 2/2008 |
| WO | WO-2008/042760 | 4/2008 |
| WO | WO-2008/128210 | 10/2008 |
| WO | WO-2008/130896 | 10/2008 |
| WO | WO-2008/130897 | 10/2008 |
| WO | WO-2008/130898 | 10/2008 |
| WO | WO-2008/143943 | 11/2008 |
| WO | WO-2008/150428 | 12/2008 |
| WO | WO-2008/153825 | 12/2008 |
| WO | WO-2009/018058 | 2/2009 |
| WO | WO-2009/075697 | 6/2009 |
| WO | WO-2009/086216 | 7/2009 |
| WO | WO-2009/096992 | 8/2009 |
| WO | WO-2009/097594 | 8/2009 |
| WO | WO-2011/022418 | 2/2011 |

OTHER PUBLICATIONS

Albery, W. J., et al., "Amperometric Enzyme Electrodes Part II: Conducting Salts as Electrode Materials for the Oxidation of Glucose Oxidase", *Journal of ElectroAnalytical Chemistry*, vol. 194, 1985, pp. 223-235.
Albery, W. J., et al., "Amperometric Enzyme Electrodes", *Philosophical Transactions of The Royal Society of London*, vol. 316, 1987, pp. 107-119.
Alcock, S. J., et al., "Continuous Analyte Monitoring to Aid Clinical Practice", *IEEE Engineering in Medicine and Biology Magazine*, 1994, pp. 319-325.
Anderson, L. B., et al., "Thin-Layer Electrochemistry: Steady-State Methods of Studying Rate Processes", *Journal of ElectroAnalytical Chemistry*, vol. 10, 1965, pp. 295-305.
Armour, J. C., et al., "Application of Chronic Intravascular Blood Glucose Sensor in Dogs", *Diabetes*, vol. 39, 1990, pp. 1519-1526.
Bartlett, P. N., et al., "Covalent Binding of Electron Relays to Glucose Oxidase", *Journal of the Chemical Society, Chemical Communications*, 1987, pp. 1603-1604.
Bartlett, P. N., et al., "Modification of Glucose Oxidase by Tetrathiafulvalene", *Journal of the Chemical Society, Chemical Communications*, 1990, pp. 1135-1136.
Bartlett, P. N., et al., "Strategies for the Development of Amperometric Enzyme Electrodes", *Biosensors*, vol. 3, 1987/88, pp. 359-379.

Bennion, N., et al., "Alternate Site Glucose Testing: A Crossover Design", *Diabetes Technology & Therapeutics*, vol. 4, No. 1, 2002, pp. 25-33.
Bindra, D. S., et al., "Design and in Vitro Studies of a Needle-Type Glucose Sensor for Subcutaneous Monitoring", *Analytical Chemistry*, vol. 63, No. 17, 1991, pp. 1692-1696.
Blank, T. B., et al., "Clinical Results From a Non-Invasive Blood Glucose Monitor", *Optical Diagnostics and Sensing of Biological Fluids and Glucose and Cholesterol Monitoring II, Proceedings of SPIE*, vol. 4624, 2002, pp. 1-10.
Bobbioni-Harsch, E., et al., "Lifespan of Subcutaneous Glucose Sensors and Their Performances During Dynamic Glycaemia Changes in Rats", *Journal of Biomedical Engineering*, vol. 15, 1993, pp. 457-463.
Boedeker Plastics, Inc., "Polyethylene Specifications", Web Page of Boedeker.com, 2007, pp. 1-3.
Brandt, J., et al., "Covalent Attachment of Proteins to Polysaccharide Carriers by Means of Benzoquinone", *Biochimica et Biophysica Acta*, vol. 386, 1975, pp. 196-202.
Brooks, S. L., et al., "Development of an On-Line Glucose Sensor for Fermentation Monitoring", *Biosensors*, vol. 3, 1987/88, pp. 45-56.
Brownlee, M., et al., "A Glucose-Controlled Insulin-Delivery System: Semisynthetic Insulin Bound to Lectin", *Science*, vol. 206, 1979, 1190-1191.
Cass, A. E., et al., "Ferricinum Ion As An Electron Acceptor for Oxido-Reductases", *Journal of ElectroAnalytical Chemistry*, vol. 190, 1985, pp. 117-127.
Cass, A. E., et al., "Ferrocene-Medicated Enzyme Electrode for Amperometric Determination of Glucose", *Analytical Chemistry*, vol. 56, No. 4, 1984, 667-671.
Castner, J. F., et al., "Mass Transport and Reaction Kinetic Parameters Determined Electrochemically for Immobilized Glucose Oxidase", *Biochemistry*, vol. 23, No. 10, 1984, 2203-2210.
Claremont, D. J., et al., "Biosensors for Continuous In Vivo Glucose Monitoring", *Proceedings of the Annual International Conference of the IEEE Engineering in Medicine and Biology Society*, vol. 10, 1988.
Clark Jr., L. C., et al., "Differential Anodic Enzyme Polarography for the Measurement of Glucose", *Oxygen Transport to Tissue: Instrumentation, Methods, and Physiology*, 1973, pp. 127-133.
Clark Jr., L. C., et al., "Electrode Systems for Continuous Monitoring in Cardiovascular Surgery", *Annals New York Academy of Sciences*, 1962, pp. 29-45.
Clark Jr., L. C., et al., "Long-term Stability of Electroenzymatic Glucose Sensors Implanted in Mice", *American Society of Artificial Internal Organs Transactions*, vol. XXXIV, 1988, pp. 259-265.
Clarke, W. L., et al., "Evaluating Clinical Accuracy of Systems for Self-Monitoring of Blood Glucose", *Diabetes Care*, vol. 10, No. 5, 1987, pp. 622-628.
Complaint, "*Abbott Diabetes Care, Inc. v. Dexcom, Inc.*", filed Aug. 11, 2005.
Complaint, Amended, "*Abbott Diabetes Care, Inc. v. Dexcom, Inc.*", filed Jun. 27, 2006.
Csoregi, E., et al., "Design and Optimization of a Selective Subcutaneously Implantable Glucose Electrode Based on 'Wired' Glucose Oxidase", *Analytical Chemistry*, vol. 67, No. 7, 1995, pp. 1240-1244.
Csoregi, E., et al., "Design, Characterization, and One-Point in Vivo Calibration of a Subcutaneously Implanted Glucose Electrode", *Analytical Chemistry*, vol. 66 No. 19, 1994, pp. 3131-3138.
Csoregi, E., et al., "On-Line Glucose Monitoring by Using Microdialysis Sampling and Amperometric Detection Based on 'Wired' Glucose Oxidase in Carbon Paste", *Mikrochimica Acta*, vol. 121, 1995, pp. 31-40.
Dai, W. S., et al., "Hydrogel Membranes with Mesh Size Asymmetry Based on the Gradient Crosslinking of Poly(vinyl alcohol)," *Journal of Membrane Science*, vol. 156, 1999, pp. 67-79.
Davis, G., "Electrochemical Techniques for the Development of Amperometric Biosensors", *Biosensors*, vol. 1, 1985, pp. 161-178.
Degani, Y., et al., "Direct Electrical Communication Between Chemically Modified Enzymes and Metal Electrodes. 1. Electron Transfer from Glucose Oxidase to Metal Electrodes via Electron Relays, Bound Covalently to the Enzyme", *The Journal of Physical Chemistry*, vol. 91, No. 6, 1987, pp. 1285-1289.

Degani, Y., et al., "Direct Electrical Communication Between Chemically Modified Enzymes and Metal Electrodes. 2. Methods for Bonding Electron-Transfer Relays to Glucose Oxidase and D-Amino-Acid Oxidase", *Journal of the American Chemical Society*, vol. 110, No. 8, 1988, pp. 2615-2620.

Degani, Y., et al., "Electrical Communication Between Redox Centers of Glucose Oxidase and Electrodes via Electrostatically and Covalently Bound Redox Polymers", *Journal of the American Chemical Society*, vol. 111, 1989, pp. 2357-2358.

Denisevich, P., et al., "Unidirectional Current Flow and Charge State Trapping at Redox Polymer Interfaces on Bilayer Electrodes: Principles, Experimental Demonstration, and Theory", *Journal of the American Chemical Society*, vol. 103, 1981, pp. 4727-4737.

Dicks, J. M., et al., "Ferrocene Modified Polypyrrole with Immobilised Glucose Oxidase and its Application in Amperometric Glucose Microbiosensors", *Annales de Biologie Clinique*, vol. 47, 1989, pp. 607-619.

Ellis, C. D., et al., "Selectivity and Directed Charge Transfer through an Electroactive Metallopolymer Film", *Journal of the American Chemical Society*, vol. 103, No. 25, 1981, pp. 7480-7483.

Engstrom, R. C., "Electrochemical Pretreatment of Glassy Carbon Electrodes", *Analytical Chemistry*, vol. 54, No. 13, 1982, pp. 2310-2314.

Engstrom, R. C., et al., "Characterization of Electrochemically Pretreated Glassy Carbon Electrodes", *Analytical Chemistry*, vol. 56, No. 2, 1984, pp. 136-141.

Feldman, B., et al., "A Continuous Glucose Sensor Based on Wired Enzyme™ Technology—Results from a 3-Day Trial in Patients with Type 1 Diabetes", *Diabetes Technology & Therapeutics*, vol. 5, No. 5, 2003, pp. 769-779.

Feldman, B., et al., "Correlation of Glucose Concentrations in Interstitial Fluid and Venous Blood During Periods of Rapid Glucose Change", *Abbott Diabetes Care, Inc. Freestyle Navigator Continuous Glucose Monitor Pamphlet*.

Feldman, B., et al., "Electron Transfer Kinetics at Redox Polymer/Solution Interfaces Using Microelectrodes and Thin Layer Cells", *Journal of ElectroAnalytical Chemistry*, vol. 194, 1985, pp. 63-81.

Fischer, H., et al., "Intramolecular Electron Transfer Medicated by 4,4'-Bypyridine and Related Bridging Groups", *Journal of the American Chemical Society*, vol. 98, No. 18, 1976, pp. 5512-5517.

Flentge, F., et al., "An Enzyme-Reactor for Electrochemical Monitoring of Choline and Acetylcholine: Applications in High-Performance Liquid Chromatography, Bran Tissue, Microdialysis and Cerebrospinal Fluid," *Analytical Biochemistry*, vol. 204, 1992, pp. 305-310.

Foulds, N. C., et al., "Enzyme Entrapment in Electrically Conducting Polymers: Immobilisation of Glucose Oxidase in Polypyrrole and its Application in Amperometric Glucose Sensors", *Journal of the Chemical Society, Faraday Transactions 1*, vol. 82, 1986, pp. 1259-1264.

Foulds, N. C., et al , "Immobilization of Glucose Oxidase in Ferrocene-Modified Pyrrole Polymers", *Analytical Chemistry*, vol. 60, No. 22, 1988, pp. 2473-2478.

Frew, J. E., et al., "Electron-Transfer Biosensors", *Philosophical Transactions of The Royal Society of London*, vol. 316, 1987, pp. 95-106.

Godsland, I. F., et al., "Maximizing the Success Rate of Minimal Model Insulin Sensitivity Measurement in Humans: The Importance of Basal Glucose Levels," *Clinical Science*, vol. 101, 2001, pp. 1-9.

Gorton, L., et al., "Selective Detection in Flow Analysis Based on the Combination of Immobilized Enzymes and Chemically Modified Electrodes", *Analytica Chimica Acta*, vol. 250, 1991, pp. 203-248.

Graham, N. B., "Poly(ethylene oxide) and Related Hydrogels," *Hydrogels in Medicine and Pharmacy*, vol. II: Polymers, Chapter 4, 1987, pp. 95-113.

Gregg, B. A., et al., "Cross-Linked Redox Gels Containing Glucose Oxidase for Amperometric Bionsensor Applications", *Analytical Chemistry*, vol. 62, No. 3, 1990, pp. 258-263.

Gregg, B. A., et al., "Redox Polymer Films Containing Enzymes. 1. A Redox-Conducting Epoxy Cement: Synthesis, Characterization, and Electrocatalytic Oxidation of Hydroquinone", *Journal of Physical Chemistry*, vol. 95, No. 15, 1991, 5970-5975.

Hale, P. D., et al., "A New Class of Amperometric Biosensor Incorporating a Polymeric Electron-Transfer Mediator", *Journal of the American Chemical Society*, vol. 111, No. 9, 1989, pp. 3482-3484.

Hamilton, "Hamilton Needle Gauge Index", www.hamiltoncompany.com.

Harrison, D. J., et al., "Characterization of Perfluorosulfonic Acid Polymer Coated Enzyme Electrodes and a Miniatureized Integrated Potentiostat for Glucose Analysis in Whole Blood", *Analytical Chemistry*, vol. 60, No. 19, 1988, pp. 2002-2007.

Hawkridge, F. M., et al., "Indirect Coulometric Titration of Biological Electron Transport Components", *Analytical Chemistry*, vol. 45, No. 7, 1973, pp. 1021-1027.

Heller, A., "Electrical Connection Enzyme Redox Centers to Electrodes", *Journal of Physical Chemistry*, vol. 96, No. 9, 1990, pp. 3579-3587.

Heller, A., "Electrical Wiring of Redox Enzymes", *Accounts of Chemical Research* vol. 23, No. 5, 1990, 128-134.

Heller, A., et al., "Amperometric Biosensors Based on Three-Dimensional Hydrogel-Forming Epoxy Networks", *Sensors and Actuators B*, vol. 13-14, 1993, pp. 180-183.

Ianniello, R. M., et al., "Differential Pulse Voltammetric Study of Direct Electron Transfer in Glucose Oxidase Chemically Modified Graphite Electrodes", *Analytical Chemistry*, vol. 54, No. 7, 1982, pp. 1098-1101.

Ianniello, R. M., et al., "Immobilized Enzyme Chemically Modified Electrode as an Amperometric Sensor", *Analytical Chemistry*, vol. 53, No. 13, 1981, pp. 2090-2095.

Ikeda, T., et al., "Glucose Oxidase-Immobilized Benzoquinone-Carbon Paste Electrode as a Glucose Sensor", *Agricultural and Biological Chemistry*, vol. 49, No. 2, 1985, pp. 541-543.

Ikeda, T., et al., "Kinetics of Outer-Sphere Electron Transfers Between Metal Complexes in Solutions and Polymeric Films on Modified Electrodes", *Journal of the American Chemical Society*, vol. 103, No. 25, 1981, pp. 7422-7425.

Isermann, R., "Supervision, Fault-Detection and Fault-Diagnosis Methods—An Introduction", *Control Engineering Practice*, vol. 5, No. 5, 1997, pp. 639-652.

Isermann, R., et al., "Trends in the Application of Model-Based Fault Detection and Diagnosis of Technical Processes", *Control Engineering Practice*, vol. 5, No. 5, 1997, pp. 709-719.

Johnson, J. M., et al., "Potential-Dependent Enzymatic Activity in an Enzyme Thin-Layer Cell", *Analytical Chemistry*, vol. 54, No. 8, 1982, pp. 1377-1383.

Johnson, K. W., "Reproducible Electrodeposition of Biomolecules for the Fabrication of Miniature Electroenzymatic Biosensors", *Sensors and Actuators B*, vol. 5, 1991, pp. 85-89.

Johnson, K. W., et al., "In vivo Evaluation of an Electroenzymatic Glucose Sensor Implanted in Subcutaneous Tissue", *Biosensors & Bioelectronics*, vol. 7, 1992, pp. 709-714.

Johnson, P. C., "Peripheral Circulation", *John Wiley & Sons*, 1978, pp. 198.

Jonsson, G., et al., "An Amperometric Glucose Sensor Made by Modification of a Graphite Electrode Surface With Immobilized Glucose Oxidase and Adsorbed Mediator", *Biosensors*, vol. 1, 1985, pp. 355-368.

Josowicz, M., et al., "Electrochemical Pretreatment of Thin Film Platinum Electrodes", *Journal of the Electrochemical Society*, vol. 135 No. 1, 1988, pp. 112-115.

Jungheim, K., et al., "How Rapid Does Glucose Concentration Change in Daily Life of Patients with Type 1 Diabetes?", pp. 250.

Jungheim, K., et al., "Risky Delay of Hypoglycemia Detection by Glucose Monitoring at the Arm", *Diabetes Care*, vol. 24, No. 7, 2001, pp. 1303-1304.

Kaplan, S. M., "Wiley Electrical and Electronics Engineering Dictionary", *IEEE Press*, 2004, pp. 141, 142, 548, 549.

Katakis, I., et al., "Electrostatic Control of the Electron Transfer Enabling Binding of Recombinant Glucose Oxidase and Redox Polyelectrolytes", *Journal of the American Chemical Society*, vol. 116, No. 8, 1994, pp. 3617-3618.

Katakis, I., et al., "L-α-Glycerophosphate and L-Lactate Electrodes Based on the Electrochemical 'Wiring' of Oxidases", *Analytical Chemistry*, vol. 64, No. 9, 1992, pp. 1008-1013.

Kemp, G. J., "Theoretical Aspects of One-Point Calibration: Causes and Effects of Some Potential Errors, and Their Dependence on Concentration," *Clinical Chemistry*, vol. 30, No. 7, 1984, pp. 1163-1167.

Kenausis, G., et al., "'Wiring' of Glucose Oxidase and Lactate Oxidase Within a Hydrogel Made with Poly(vinyl pyridine) complexed with $[Os(4,4'\text{-dimethoxy-}2,2'\text{-bipyridine})_2 \ Cl]^{+/2+}$", *Journal of the Chemical Society, Faraday Transactions*, vol. 92, No. 20, 1996, pp. 4131-4136.

Kerner, W., et al., "The Function of a Hydrogen Peroxide-Detecting Electroenzymatic Glucose Electrode is Markedly Impaired in Human Subcutaneous Tissue and Plasma," *Biosensors & Bioelectronics*, vol. 8, 1993, pp. 473-482.

Korf, J., et al., "Monitoring of Glucose and Lactate Using Microdialysis: Applications in Neonates and Rat Brain," *Developmental Neuroscience*, vol. 15, 1993, pp. 240-246.

Koudelka, M., et al., "In-Vivo Behaviour of Hypodermically Implanted Microfabricated Glucose Sensors", *Biosensors & Bioelectronics*, vol. 6, 1991, pp. 31-36.

Kulys, J., et al., "Mediatorless Peroxidase Electrode and Preparation of Bienzyme Sensors", *Bioelectrochemistry and Bioenergetics*, vol. 24, 1990, pp. 305-311.

Lager, W., et al., "Implantable Electrocatalytic Glucose Sensor", *Hormone Metabolic Research*, vol. 26, 1994, pp. 526-530.

Laurell, T., "A Continuous Glucose Monitoring System Based on Microdialysis", *Journal of Medical Engineering & Technology*, vol. 16, No. 5, 1992, pp. 187-193.

Lindner, E., et al., "Flexible (Kapton-Based) Microsensor Arrays of High Stability for Cardiovascular Applications", *Journal of the Chemical Society, Faraday Transactions*, vol. 89, No. 2, 1993, pp. 361-367.

Lortz, J., et al., "What is Bluetooth? We Explain the Newest Short-Range Connectivity Technology", *Smart Computing Learning Series, Wireless Computing*, vol. 8, Issue 5, 2002, pp. 72-74.

Maidan, R., et al., "Elimination of Electrooxidizable Interferant-Produced Currents in Amperometric Biosensors", *Analytical Chemistry*, vol. 64, No. 23, 1992, pp. 2889-2896.

Malin, S. F., et al., "Noninvasive Prediction of Glucose by Near-Infrared Diffuse Reflectance Spectoscopy", *Clinical Chemistry*, vol. 45, No. 9, 1999, pp. 1651-1658.

Marko-Varga, G., et al., "Enzyme-Based Biosensor as a Selective Detection Unit in Column Liquid Chromatography", *Journal of Chromatography A*, vol. 660, 1994, pp. 153-167.

Mastrototaro, J. J., et al., "An Electroenzymatic Glucose Sensor Fabricated on a Flexible Substrate", *Sensors and Actuators B*, vol. 5, 1991, pp. 139-144.

Mauras, N., et al., "Lack of Accuracy of Continuous Glucose Sensors in Healthy, Nondiabetic Children: Results of the Diabetes Research in Children Network (DirecNet) Accuracy Study," *Journal of Pediatrics*, 2004, pp. 770-775.

McGarraugh, G., et al., "Glucose Measurements Using Blood Extracted from the Forearm and the Finger", *TheraSense, Inc.*, 16 Pages.

McGarraugh, G., et al., "Physiological Influences on Off-Finger Glucose Testing", *Diabetes Technology & Therapeutics*, vol. 3, No. 3, 2001, pp. 367-376.

McKean, B. D., et al., "A Telemetry-Instrumentation System for Chronically Implanted Glucose and Oxygen Sensors", *IEEE Transactions on Biomedical Engineering*, vol. 35, No. 7, 1988, pp. 526-532.

McNeil, C. J., et al., "Thermostable Reduced Nicotinamide Adenine Dinucleotide Oxidase: Application to Amperometric Enzyme Assay", *Analytical Chemistry*, vol. 61, No. 1, 1989, pp. 25-29.

Miyawaki, O., et al., "Electrochemical and Glucose Oxidase Coenzyme Activity of Flavin Adenine Dinucleotide Covalently Attached to Glassy Carbon at the Adenine Amino Group", *Biochimica et Biophysica Acta*, vol. 838, 1985, pp. 60-68.

Moatti-Sirat, D., et al., "Evaluating In Vitro and In Vivo the Interference of Ascorbate and Acetaminophen on Glucose Detection by a Needle-Type Glucose Sensor", *Biosensors & Bioelectronics*, vol. 7, 1992, pp. 345-352.

Moatti-Sirat, D., et al., "Reduction of Acetaminophen Interference in Glucose Sensors by a Composite Nafion Membrane: Demonstration in Rats and Man", *Diabetologia*, vol. 37, 1994, pp. 610-616.

Moatti-Sirat, D., et al., "Towards Continuous Glucose Monitoring: In Vivo Evaluation of a Miniaturized Glucose Sensor Implanted for Several Days in Rat Subcutaneous Tissue", *Diabetologia*, vol. 35, 1992, pp. 224-330.

Nagy, G., et al., "A New Type of Enzyme Electrode: The Ascorbic Acid Eliminator Electrode", *Life Sciences*, vol. 31, No. 23, 1982, pp. 2611-2616.

Nakamura, S., et al., "Effect of Periodate Oxidation on the Structure and Properties of Glucose Oxidase", *Biochimica et Biophysica Acta*, vol. 445, 1976, pp. 294-308.

Narasimham, K., et al., "p-Benzoquinone Activation of Metal Oxide Electrodes for Attachment of Enzymes", *Enzyme and Microbial Technology*, vol. 7, 1985, pp. 283-286.

Ohara, T. J., "Osmium Bipyridyl Redox Polymers Used in Enzyme Electrodes", *Platinum Metals Review*, vol. 39, No. 2, 1995, pp. 54-62.

Ohara, T. J., et al., "'Wired' Enzyme Electrodes for Amperometric Determination of Glucose or Lactate in the Presence of Interfering Substances", *Analytical Chemistry*, vol. 66, No. 15, 1994, pp. 2451-2457.

Ohara, T. J., et al., "Glucose Electrodes Based on Cross-Linked $[Os(bpy)_2 Cl]^{+/2 \ +}$ Complexed Poly(1-Vinylimidazole) Films", *Analytical Chemistry*, vol. 65, No. 23, 1993, pp. 3512-3517.

Olievier, C. N., et al., "In Vivo Measurement of Carbon Dioxide Tension with a Miniature Electrodes", *Pflugers Archiv: European Journal of Physiology*, vol. 373, 1978, pp. 269-272.

Paddock, R. M., et al., "Electrocatalytic Reduction of Hydrogen Peroxide via Direct Electron Transfer From Pyrolytic Graphite Electrodes to Irreversibly Adsorbed Cyctochrome C Peroxidase", *Journal of ElectroAnalytical Chemistry*, vol. 260, 1989, pp. 487-494.

Palleschi, G., et al., "A Study of Interferences in Glucose Measurements in Blood by Hydrogen Peroxide Based Glucose Probes", *Analytical Biochemistry*, vol. 159, 1986, pp. 114-121.

Pankratov, I., et al., "Sol-Gel Derived Renewable-Surface Biosensors", *Journal of ElectroAnalytical Chemistry*, vol. 393, 1995, pp. 35-41.

Pathak, C., et al., "Rapid Photopolymerization of Immunoprotective Gels in Contact with Cells and Tissue", *Journal of the American Chemical Society*, vol. 114, No. 21, 1992, pp. 8311-8312.

Pickup, J., "Developing Glucose Sensors for In Vivo Use", *Tibtech*, vol. 11, 1993, pp. 285-291.

Pickup, J., et al., "Implantable Glucose Sensors: Choosing the Appropriate Sensing Strategy", *Biosensors*, vol. 3, 1987/88, pp. 335-346.

Pickup, J., et al., "In Vivo Molecular Sensing in Diabetes Mellitus: An Implantable Glucose Sensor with Direct Electron Transfer", *Diabetologia*, vol. 32, 1989, pp. 213-217.

Pickup, J., et al., "Potentially-Implantable, Amperometric Glucose Sensors with Mediated Electron Transfer: Improving the Operating Stability", *Biosensors*, vol. 4, 1989, pp. 109-119.

Pishko, M. V., et al., "Amperometric Glucose Microelectrodes Prepared Through Immobilization of Glucose Oxidase in Redox Hydrogels", *Analytical Chemistry*, vol. 63, No. 20, 1991, pp. 2268-2272.

Poitout, V., et al., "A Glucose Monitoring System for On Line Estimation in Man of Blood Glucose Concentration Using a Miniaturized Glucose Sensor Implanted in the Subcutaneous Tissue and a Wearable Control Unit", *Diabetolgia*, vol. 36, 1993, pp. 658-663.

Poitout, V., et al., "Calibration in Dogs of a Subcutaneous Miniaturized Glucose Sensor Using Glucose Meter for Blood Glucose Determination", *Biosensors & Bioelectronics*, vol. 7, 1992, pp. 587-592.

Poitout, V., et al., "In Vitro and In Vivo Evaluation in Dogs of a Miniaturized Glucose Sensor", *ASAIO Transactions*, vol. 37, No. 3, 1991, pp. M298-M300.

Pollak, A., et al., "Enzyme Immobilization by Condensation Copolymerization into Cross-Linked Polyacrylamide Gels", *Journal of the American Chemical Society*, vol. 102, No. 20, 1980, pp. 6324-6336.

Quinn, C. P., et al., "Kinetics with Glucose Delivery to Subcutaneous Tissue in Rats Measured with 0.3-mm Amperometric Microsensors", *The American Physiological Society*, 1995, E155-E161.

Reach, G., et al., "Can Continuous Glucose Monitoring Be Used for the Treatment of Diabetes?", *Analytical Chemistry*, vol. 64, No. 6, 1992, pp. 381-386.

Rebrin, K., et al., "Automated Feedback Control of Subcutaneous Glucose Concentration in Diabetic Dogs", *Diabetologia*, vol. 32, 1989, pp. 573-576.

Reusch, W., "Other Topics: Organometallic Chemistry: Organometallic Compounds: Main Group Organometallic Compounds," *Virtual Textbook of Organic Chemistry*, 1999, Rev. 2007, 25 pages.

Roe, J. N., et al., "Bloodless Glucose Measurements", *Critical Review in Therapeutic Drug Carrier Systems*, vol. 15, Issue 3, 1998, pp. 199-241.

Sacks (Ed), "Guidelines and Recommendations for Laboratory Analysis in the Diagnosis and Management of Diabetes Mellitus," *The National Academy of Clinical Biochemistry Presents Laboratory Medicine Practice Guidelines*, vol. 13, 2002, pp. 8-11, 21-23, 52-56, 63.

Sakakida, M., et al., "Development of Ferrocene-Mediated Needle-Type Glucose Sensor as a Measure of True Subcutaneous Tissue Glucose Concentrations", *Artificial Organs Today*, vol. 2, No. 2, 1992, pp. 145-158.

Sakakida, M., et al., "Ferrocene-Mediated Needle-Type Glucose Sensor Covered with Newly Designed Biocompatible Membrane", *Sensors and Actuators B*, vol. 13-14, 1993, pp. 319-322.

Salehi, C., et al., "A Telemetry-Instrumentation System for Long-Term Implantable Glucose and Oxygen Sensors", *Analytical Letters*, vol. 29, No. 13, 1996, pp. 2289-2308.

Samuels, G. J., et al., "An Electrode-Supported Oxidation Catalyst Based on Ruthenium (IV). pH 'Encapsulation' in a Polymer Film", *Journal of the American Chemical Society*, vol. 103, No. 2, 1981, pp. 307-312.

Sasso, S. V., et al., "Electropolymerized 1,2-Diaminobenzene as a Means to Prevent Interferences and Fouling and to Stabilize Immobilized Enzyme in Electrochemical Biosensors", *Analytical Chemistry*, vol. 62, No. 11, 1990, pp. 1111-1117.

Scheller, F. W., et al., "Second Generation Biosensors," *Biosensors & Bioelectronics*, vol. 6, 1991, pp. 245-253.

Scheller, F., et al., "Enzyme Electrodes and Their Application", *Philosophical Transactions of The Royal Society of London B*, vol. 316, 1987, pp. 85-94.

Schmehl, R. H., et al., "The Effect of Redox Site Concentration on the Rate of Mediated Oxidation of Solution Substrates by a Redox Copolymer Film", *Journal of ElectroAnalytical Chemistry*, vol. 152, 1983, pp. 97-109.

Schmidt, F. J., et al., "Calibration of a Wearable Glucose Sensor", *The International Journal of Artificial Organs*, vol. 15, No. 1, 1992, pp. 55-61.

Schmidtke, D. W., et al., "Measurement and Modeling of the Transient Difference Between Blood and Subcutaneous Glucose Concentrations in the Rat After Injection of Insulin", *Proceedings of the National Academy of Sciences*, vol. 95, 1998, pp. 294-299.

Shaw, G. W., et al., "In Vitro Testing of a Simply Constructed, Highly Stable Glucose Sensor for Implantation in Diabetic Patients", *Biosensors & Bioelectronics*, vol. 6, 1991, pp. 401-406.

Shichiri, M., et al., "Glycaemic Control in Pancreatectomized Dogs with a Wearable Artificial Endocrine Pancreas", *Diabetologia*, vol. 24, 1983, pp. 179-184.

Shichiri, M., et al., "In Vivo Characteristics of Needle-Type Glucose Sensor—Measurements of Subcutaneous Glucose Concentrations in Human Volunteers", *Hormone and Metabolic Research Supplement Series*, vol. 20, 1988, pp. 17-20.

Shichiri, M., et al., "Membrane Design for Extending the Long-Life of an Implantable Glucose Sensor", *Diabetes Nutrition and Metabolism*, vol. 2, 1989, pp. 309-313.

Shichiri, M., et al., "Needle-type Glucose Sensor for Wearable Artificial Endocrine Pancreas", *Implantable Sensors for Closed-Loop Prosthetic Systems*, Chapter 15, 1985, pp. 197-210.

Shichiri, M., et al., "Telemetry Glucose Monitoring Device With Needle-Type Glucose Sensor: A Useful Tool for Blood Glucose Monitoring in Diabetic Individuals", *Diabetes Care*, vol. 9, No. 3, 1986, pp. 298-301.

Shichiri, M., et al., "Wearable Artificial Endocrine Pancreas With Needle-Type Glucose Sensor", *The Lancet*, 1982, pp. 1129-1131.

Shults, M. C., et al., "A Telemetry-Instrumentation System for Monitoring Multiple Subcutaneously Implanted Glucose Sensors", *IEEE Transaction on Biomedical Engineering*, Vol. 41, No. 10, 1994, pp. 937-942.

Sittampalam, G., et al., "Surface-Modified Electrochemical Detector for Liquid Chromatography", *Analytical Chemistry*, vol. 55, No. 9, 1983, pp. 1608-1610.

Skoog, D. A., et al., "Evaluation of Analytical Data," *Fundamentals of Analytical Chemistry*, 1966, pp. 55.

Soegijoko, S., et al., "External Artificial Pancreas: A New Control Unit Using Microprocessor", *Hormone and Metabolic Research Supplement Series*, vol. 12, 1982, pp. 165-169.

Sprules, S. D., et al., "Evaluation of a New Disposable Screen-Printed Sensor Strip for the Measurement of NADH and Its Modification to Produce a Lactate Biosensor Employing Microliter Volumes", *Electroanalysis*, vol. 8, No. 6, 1996, pp. 539-543.

Sternberg, F., et al., "Calibration Problems of Subcutaneous Glucosensors when Applied 'In-Situ' in Man", *Hormone and Metabolic Research*, vol. 26, 1994, pp. 523-526.

Sternberg, R., et al., "Covalent Enzyme Coupling on Cellulose Acetate Membranes for Glucose Sensor Development", *Analytical Chemistry*, vol. 60, No. 24, 1988, pp. 2781-2786.

Sternberg, R., et al., "Study and Development of Multilayer Needle-Type Enzyme-Based Glucose Microsensors", *Biosensors*, vol. 4, 1988, pp. 27-40.

Suekane, M., "Immobilization of Glucose Isomerase", *Zettschrift fur Allgemeine Mikrobiologie*, vol. 22, No. 8, 1982, pp. 565-576.

Tajima, S., et al., "Simultaneous Determination of Glucose and 1,5-Anydroglucitol", *Chemical Abstracts*, vol. 111, No. 25, 1989, pp. 394.

Takamura, A., et al., Drug release from Poly(vinyl alcohol) Gel Prepared by Freeze-Thaw Procedure, *Journal of Controlled Release*, vol. 20, 1992, pp. 21-27.

Tarasevich, M. R., "Bioelectrocatalysis", *Comprehensive Treatise of Electrochemistry*, vol, 10, 1985, pp. 231-295.

Tatsuma, T., et al., "Enzyme Monolayer—and Bilayer-Modified Tin Oxide Electrodes for the Determination of Hydrogen Peroxide and Glucose", *Analytical Chemistry*, vol. 61, No. 21, 1989, pp. 2352-2355.

Taylor, C., et al., "'Wiring' of Glucose Oxidase Within a Hydrogel Made with Polyvinyl Imidazole Complexed with [(Os-4,4'-dimethoxy-2,2'-bipyridine)C1]$^{+2+}$", *Journal of ElectroAnalytical Chemistry*, vol. 396, 1995, pp. 511-515.

Thompson, M., et al., "In Vivo Probes: Problems and Perspectives", *Clinical Biochemistry*, vol. 19, 1986, pp. 255-261.

Trojanowicz, M., et al., "Enzyme Entrapped Polypyrrole Modified Electrode for Flow-Injection Determination of Glucose", *Biosensors & Bioelectronics*, vol. 5, 1990, pp. 149-156.

Tsalikian, E., et al., "Accuracy of the GlucoWatch G2® Biographer and the Continuous Glucose Monitoring System During Hypoglycemia: Experience of the Diabetes Research in Children Network", *Diabetes Care*, vol. 27, No. 3, 2004, pp. 722-726.

Turner, A., et al., "Diabetes Mellitus: Biosensors for Research and Management", *Biosensors*, vol. 1, 1985, pp. 85-115.

Turner, R. F., et al., "A Biocompatible Enzyme Electrode for Continuous in vivo Glucose Monitoring in Whole Blood", *Sensors and Actuators B*, vol. 1, 1990, pp. 561-564.

Tuzhi, P., et al., "Constant Potential Pretreatment of Carbon Fiber Electrodes for In Vivo Electrochemistry", *Analytical Letters*, vol. 24, No. 6, 1991, pp. 935-945.

U.S. Patent Reexamination U.S. Appl. No. 90/007,903, Request for Reexamination of U.S. Patent No. 6,565,509, filed Jan. 25, 2006.

U.S. Patent Reexamination U.S. Appl. No. 90/007,910, Request for Reexamination of U.S. Patent No. 6,175,752, filed Feb. 1, 2006.

U.S. Patent Reexamination U.S. Appl. No. 90/007,913, Request for Reexamination of U.S. Patent No. 6,284,478, filed Feb. 1, 2006.

U.S. Patent Reexamination U.S. Appl. No. 90/007,914, Request for Reexamination of U.S. Patent No. 6,329,161, filed Feb. 1, 2006.

U.S. Patent Reexamination U.S. Appl. No. 90/008,172, Request for Reexamination of U.S. Patent No. 6,990,366, filed Aug. 16, 2006.

U.S. Patent Reexamination U.S. Appl. No. 90/008,173, Request for Reexamination of U.S. Patent No. 6,134,461, filed Aug. 16, 2006.

U.S. Patent Reexamination U.S. Appl. No. 90/008,457, Request for Reexamination of U.S. Patent No. 6,990,366, filed Jan. 23, 2007.

U.S. Patent Reexamination U.S. Appl. No. 90/008,665, Request for Reexamination of U.S. Patent No. 6,284,478, filed May 25, 2007.

U.S. Patent Reexamination U.S. Appl. No. 90/008,713, Request for Reexamination of U.S. Patent No. 6,329,161, filed Jul. 25, 2007.

Umana, M., "Protein-Modified Electrochemically Active Biomaterial Surface", *U.S. Army Research Office, Analytical and Chemical Sciences Research Triangle Institute*, 1988, pp. 1-9.

Updike, S. J., et al., "Principles of Long-Term Fully Implanted Sensors with Emphasis on Radiotelemetric Monitoring of Blood Glucose from Inside a Subcutaneous Foreign Body Capsule (FBC)", *Biosensors in the Body: Continuous in vivo Monitoring, Chapter 4*, 1997, pp. 117-137.

Urban, G., et al., "Miniaturized Thin-Film Biosensors Using Covalently Immobilized Glucose Oxidase", *Biosensors & Bioelectronics*, vol. 6, 1991, pp. 555-562.

Velho, G., et al., "In Vitro and In Vivo Stability of Electrode Potentials in Needle-Type Glucose Sensors", *Diabetes*, vol. 38, No. 2, 1989, pp. 164-171.

Velho, G., et al., "Strategies for Calibrating a Subcutaneous Glucose Sensor", *Biomedica Biochimica Acta*, vol. 48, 1989, pp. 957-964.

Von Woedtke, T., et al., "In Situ Calibration of Implanted Electrochemical Glucose Sensors", *Biomedica Biochimica Acta*, vol. 48, 1989, pp. 943-952.

Vreeke, M. S., et al., "Hydrogen Peroxide Electrodes Based on Electrical Connection of Redox Centers of Various Peroxidases to Electrodes through a Three-Dimensional Electron-Relaying Polymer Network", *Diagnostic Biosensors Polymers*, Chapter 15, 1993, pp. 180-193.

Vreeke, M., et al., "Hydrogen Peroxide and β-Nicotinamide Adenine Dinucleotide Sensing Amperometric Electrodes Based on Electrical Connection of Horseradish Peroxidase Redox Centers to Electrodes through a Three-Dimensional Electron Relaying Polymer Network", *Analytical Chemistry*, vol. 64, No. 24, 1992, pp. 3084-3090.

Wang, D. L., et al., "Miniaturized Flexible Amperometric Lactate Probe", *Analytical Chemistry*, vol. 65, No. 8, 1993, pp. 1069-1073.

Wang, J., et al., "Activation of Glassy Carbon Electrodes by Alternating Current Electrochemical Treatment", *Analytica Chimica Acta*, vol. 167, 1985, pp. 325-334.

Wang, J., et al., "Amperometric Biosensing of Organic Peroxides with Peroxidase-Modified Electrodes", *Analytica Chimica Acta*, vol. 254, 1991, pp. 81-88.

Wang, J., et al., "Screen-Printable Sol-Gel Enzyme-Containing Carbon Inks", *Analytical Chemistry*, vol. 68, No. 15, 1996, pp. 2705-2708.

Wang, J., et al., "Sol-Gel-Derived Metal-Dispersed Carbon Composite Amperometric Biosensors", *Electroanalysis*, vol. 9, No. 1, 1997, pp. 52-55.

Williams, D. L., et al., "Electrochemical-Enzymatic Analysis of Blood Glucose and Lactate", *Analytical Chemistry*, vol. 42, No. 1, 1970, pp. 118-121.

Wilson, G. S., et al., "Progress Toward the Development of an Implantable Sensor for Glucose", *Clinical Chemistry*, vol. 38, No. 9, 1992, pp. 1613-1617.

Yabuki, S., et al., "Electro-Conductive Enzyme Membrane", *Journal of the Chemical Society, Chemical Communications*, 1989, pp. 945-946.

Yang, C., et al., "A Comparison of Physical Properties and Fuel Cell Performance of Nafion and Zirconium Phosphate/Nafion Composite Membranes," *Journal of Membrane Science*, vol. 237, 2004, pp. 145-161.

Yang, L., et al., "Determination of Oxidase Enzyme Substrates Using Cross-Flow Thin-Layer Amperometry", *Electroanalysis*, vol. 8, No. 8-9, 1996, pp. 716-721.

Yao, S. J., et al., "The Interference of Ascorbate and Urea in Low-Potential Electrochemical Glucose Sensing", *Proceedings of the Twelfth Annual International Conference of the IEEE Engineering in Medicine and Biology Society*, vol. 12, Part 2, 1990, pp. 487-489.

Yao, T., "A Chemically-Modified Enzyme Membrane Electrode as an Amperometric Glucose Sensor", *Analytica Chimica Acta*, vol. 148, 1983, pp. 27-33.

Ye, L., et al., "High Current Density 'Wired' Quinoprotein Glucose Dehydrogenase Electrode", *Analytical Chemistry*, vol. 65, No. 3, 1993, pp. 238-241.

Yildiz, A., et al., "Evaluation of an Improved Thin-Layer Electrode", *Analytical Chemistry*, vol. 40, No. 7, 1968, pp. 1018-1024.

Zamzow, K., et al., "New Wearable Continuous Blood Glucose Monitor (BGM) and Artificial Pancreas (AP)", *Diabetes*, vol. 39, 1990, pp. 5A-20.

Zhang, Y., et al., "Application of Cell Culture Toxicity Tests to the Development of Implantable Biosensors", *Biosensors & Bioelectronics*, vol. 6, 1991, pp. 653-661.

Zhang, Y., et al., "Elimination of the Acetaminophen Interference in an Implantable Glucose Sensor", *Analytical Chemistry*, vol. 66, No. 7, 1994, pp. 1183-1188.

Travenol Laboratories, Inc., An Introduction to "Eugly", Book 1, 1985, pp. 1-22.

International Search Report and Written Opinion of the International Searching Authority for PCT Application No. PCT/US2008/055501 filed Feb. 29, 2008 to Abbott Diabetes Care, Inc., mailed Sep. 2, 2008.

Chinese Patent Application No. 200880006612.4, Original Language and English Translation of Office Action mailed Feb. 9, 2011.

PCT Application No. PCT/US2008/055501, International Preliminary Report on Patentability and Written Opinion of the International Searching Authority mailed Sep. 11, 2009.

* cited by examiner

METHOD AND APPARATUS FOR PROVIDING ROLLING DATA IN COMMUNICATION SYSTEMS

BACKGROUND

Analyte, e.g., glucose monitoring systems including continuous and discrete monitoring systems generally include a small, lightweight battery powered and microprocessor controlled system which is configured to detect signals proportional to the corresponding measured glucose levels using an electrometer. RF signals may be used to transmit the collected data. One aspect of certain analyte monitoring systems include a transcutaneous or subcutaneous analyte sensor configuration which is, for example, at least partially positioned through the skin layer of a subject whose analyte level is to be monitored. The sensor may use a two or three-electrode (work, reference and counter electrodes) configuration driven by a controlled potential (potentiostat) analog circuit connected through a contact system.

An analyte sensor may be configured so that a portion thereof is placed under the skin of the patient so as to contact analyte of the patient, and another portion or segment of the analyte sensor may be in communication with the transmitter unit. The transmitter unit may be configured to transmit the analyte levels detected by the sensor over a wireless communication link such as an RF (radio frequency) communication link to a receiver/monitor unit. The receiver/monitor unit may perform data analysis, among other functions, on the received analyte levels to generate information pertaining to the monitored analyte levels.

Transmission of data over an RF communication link is often constrained to occur within a substantially short time duration. In turn, the time constraint in RF data communication imposes limits on the type and size of data that may be transmitted during the transmission time period.

In view of the foregoing, it would be desirable to have a method and apparatus for optimizing the RF communication link between two or more communication devices, for example, in a medical communication system.

SUMMARY OF THE INVENTION

Devices and methods for analyte monitoring, e.g., glucose monitoring, are provided. Embodiments include transmitting information from a first location to a second, e.g., using a telemetry system such as RF telemetry. Systems herein include continuous analyte monitoring systems and discrete analyte monitoring system.

In one embodiment, a method including retrieving a first data type, retrieving a second data type, transmitting a first data packet including the first data type and the second data type, updating the second data type, and generating a second data packet including the first data type and the updated second data type, is disclosed, as well as devices and systems for the same.

These and other objects, features and advantages of the present invention will become more fully apparent from the following detailed description of the embodiments, the appended claims and the accompanying drawings.

DETAILED DESCRIPTION

As summarized above and as described in further detail below, in accordance with the various embodiments of the present invention, there is provided a method and system for retrieving a first data type, retrieving a second data type, transmitting a first data packet including the first data type and the second data type, updating the second data type, and generating a second data packet including the first data type and the updated second data type.

Figure 1:
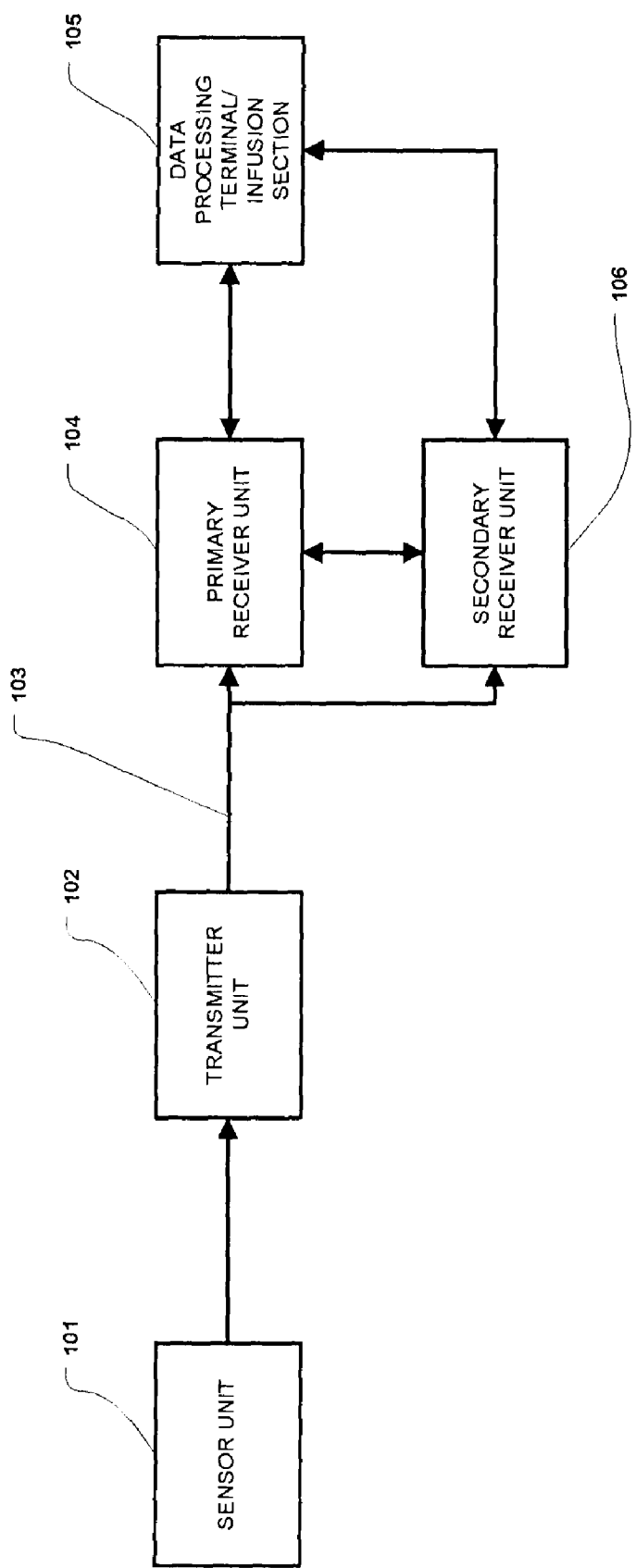
FIG. 1 illustrates a block diagram of a data monitoring and management system for practicing one or more embodiments of the present invention.

FIG. 1 illustrates a data monitoring and management system such as, for example, analyte (e.g., glucose) monitoring system 100 in accordance with one embodiment of the present invention. The subject invention is further described primarily with respect to a glucose monitoring system for convenience and such description is in no way intended to limit the scope of the invention. It is to be understood that the analyte monitoring system may be configured to monitor a variety of analytes, e.g., lactate, and the like.

Analytes that may be monitored include, for example, acetyl choline, amylase, bilirubin, cholesterol, chorionic gonadotropin, creatine kinase (e.g., CK-MB), creatine, DNA, fructosamine, glucose, glutamine, growth hormones, hormones, ketones, lactate, peroxide, prostate-specific antigen, prothrombin, RNA, thyroid stimulating hormone, and troponin. The concentration of drugs, such as, for example, antibiotics (e.g., gentamicin, vancomycin, and the like), digitoxin, digoxin, drugs of abuse, theophylline, and warfarin, may also be monitored. More than one analyte may be monitored by a single system, e.g. a single analyte sensor.

The analyte monitoring system 100 includes a sensor unit 101, a transmitter unit 102 coupleable to the sensor unit 101, and a primary receiver unit 104 which is configured to communicate with the transmitter unit 102 via a communication link 103. The primary receiver unit 104 may be further configured to transmit data to a data processing terminal 105 for evaluating the data received by the primary receiver unit 104. Moreover, the data processing terminal 105 in one embodiment may be configured to receive data directly from the transmitter unit 102 via a communication link which may optionally be configured for bi-directional communication. Accordingly, transmitter unit 102 and/or receiver unit 104 may include a transceiver.

Also shown in FIG. 1 is an optional secondary receiver unit 106 which is operatively coupled to the communication link and configured to receive data transmitted from the transmitter unit 102. Moreover, as shown in the Figure, the secondary receiver unit 106 is configured to communicate with the primary receiver unit 104 as well as the data processing terminal 105. Indeed, the secondary receiver unit 106 may be configured for bidirectional wireless communication with each or one of the primary receiver unit 104 and the data processing terminal 105. As discussed in further detail below, in one embodiment of the present invention, the secondary receiver unit 106 may be configured to include a limited number of functions and features as compared with the primary receiver unit 104. As such, the secondary receiver unit 106 may be configured substantially in a smaller compact housing or embodied in a device such as a wrist watch, pager, mobile phone, PDA, for example. Alternatively, the secondary receiver unit 106 may be configured with the same or substantially similar functionality as the primary receiver unit 104. The receiver unit may be configured to be used in conjunction with a docking cradle unit, for example for one or more of the following or other functions: placement by bedside, for re-charging, for data management, for night time monitoring, and/or bi-directional communication device.

In one aspect sensor unit 101 may include two or more sensors, each configured to communicate with transmitter unit 102. Furthermore, while only one, transmitter unit 102, communication link 103, and data processing terminal 105 are shown in the embodiment of the analyte monitoring system 100 illustrated in FIG. 1. However, it will be appreciated by one of ordinary skill in the art that the analyte monitoring system 100 may include one or more sensors, multiple transmitter units 102, communication links 103, and data processing terminals 105. Moreover, within the scope of the present invention, the analyte monitoring system 100 may be a continuous monitoring system, or semi-continuous, or a discrete monitoring system. In a multi-component environment, each device is configured to be uniquely identified by each of the other devices in the system so that communication conflict is readily resolved between the various components within the analyte monitoring system 100.

In one embodiment of the present invention, the sensor unit 101 is physically positioned in or on the body of a user whose analyte level is being monitored. The sensor unit 101 may be configured to continuously sample the analyte level of the user and convert the sampled analyte level into a corresponding data signal for transmission by the transmitter unit 102. In certain embodiments, the transmitter unit 102 may be physically coupled to the sensor unit 101 so that both devices are integrated in a single housing and positioned on the user's body. The transmitter unit 102 may perform data processing such as filtering and encoding on data signals and/or other functions, each of which corresponds to a sampled analyte level of the user, and in any event transmitter unit 102 transmits analyte information to the primary receiver unit 104 via the communication link 103.

In one embodiment, the analyte monitoring system 100 is configured as a one-way RF communication path from the transmitter unit 102 to the primary receiver unit 104. In such embodiment, the transmitter unit 102 transmits the sampled data signals received from the sensor unit 101 without acknowledgement from the primary receiver unit 104 that the transmitted sampled data signals have been received. For example, the transmitter unit 102 may be configured to transmit the encoded sampled data signals at a fixed rate (e.g., at one minute intervals) after the completion of the initial power on procedure. Likewise, the primary receiver unit 104 may be configured to detect such transmitted encoded sampled data signals at predetermined time intervals. Alternatively, the analyte monitoring system 100 may be configured with a bi-directional RF (or otherwise) communication between the transmitter unit 102 and the primary receiver unit 104.

Additionally, in one aspect, the primary receiver unit 104 may include two sections. The first section is an analog interface section that is configured to communicate with the transmitter unit 102 via the communication link 103. In one embodiment, the analog interface section may include an RF receiver and an antenna for receiving and amplifying the data signals from the transmitter unit 102, which are thereafter, demodulated with a local oscillator and filtered through a band-pass filter. The second section of the primary receiver unit 104 is a data processing section which is configured to process the data signals received from the transmitter unit 102 such as by performing data decoding, error detection and correction, data clock generation, and data bit recovery.

In operation, upon completing the power-on procedure, the primary receiver unit 104 is configured to detect the presence of the transmitter unit 102 within its range based on, for example, the strength of the detected data signals received from the transmitter unit 102 and/or a predetermined transmitter identification information. Upon successful synchronization with the corresponding transmitter unit 102, the primary receiver unit 104 is configured to begin receiving from the transmitter unit 102 data signals corresponding to the user's detected analyte level. More specifically, the primary receiver unit 104 in one embodiment is configured to perform synchronized time hopping with the corresponding synchronized transmitter unit 102 via the communication link 103 to obtain the user's detected analyte level.

Referring again to FIG. 1, the data processing terminal 105 may include a personal computer, a portable computer such as a laptop or a handheld device (e.g., personal digital assistants (PDAs)), and the like, each of which may be configured for data communication with the receiver via a wired or a wireless connection. Additionally, the data processing terminal 105 may further be connected to a data network (not shown) for storing, retrieving and updating data corresponding to the detected analyte level of the user.

Within the scope of the present invention, the data processing terminal 105 may include an infusion device such as an insulin infusion pump (external or implantable) or the like, which may be configured to administer insulin to patients, and which may be configured to communicate with the receiver unit 104 for receiving, among others, the measured analyte level. Alternatively, the receiver unit 104 may be configured to integrate or otherwise couple to an infusion device therein so that the receiver unit 104 is configured to administer insulin therapy to patients, for example, for administering and modifying basal profiles, as well as for determining appropriate boluses for administration based on, among others, the detected analyte levels received from the transmitter unit 102.

Additionally, the transmitter unit 102, the primary receiver unit 104 and the data processing terminal 105 may each be configured for bidirectional wireless communication such that each of the transmitter unit 102, the primary receiver unit 104 and the data processing terminal 105 may be configured to communicate (that is, transmit data to and receive data from) with each other via the wireless communication link 103. More specifically, the data processing terminal 105 may in one embodiment be configured to receive data directly from the transmitter unit 102 via the communication link 106, where the communication link 106, as described above, may be configured for bidirectional communication.

In this embodiment, the data processing terminal 105 which may include an insulin pump, may be configured to receive the analyte signals from the transmitter unit 102, and thus, incorporate the functions of the receiver 103 including data processing for managing the patient's insulin therapy and analyte monitoring. In one embodiment, the communication link 103 may include one or more of an RF communication protocol, an infrared communication protocol, a Bluetooth enabled communication protocol, an 802.11x wireless communication protocol, or an equivalent wireless communication protocol which would allow secure, wireless communication of several units (for example, per HIPPA requirements) while avoiding potential data collision and interference.

Figure 2:
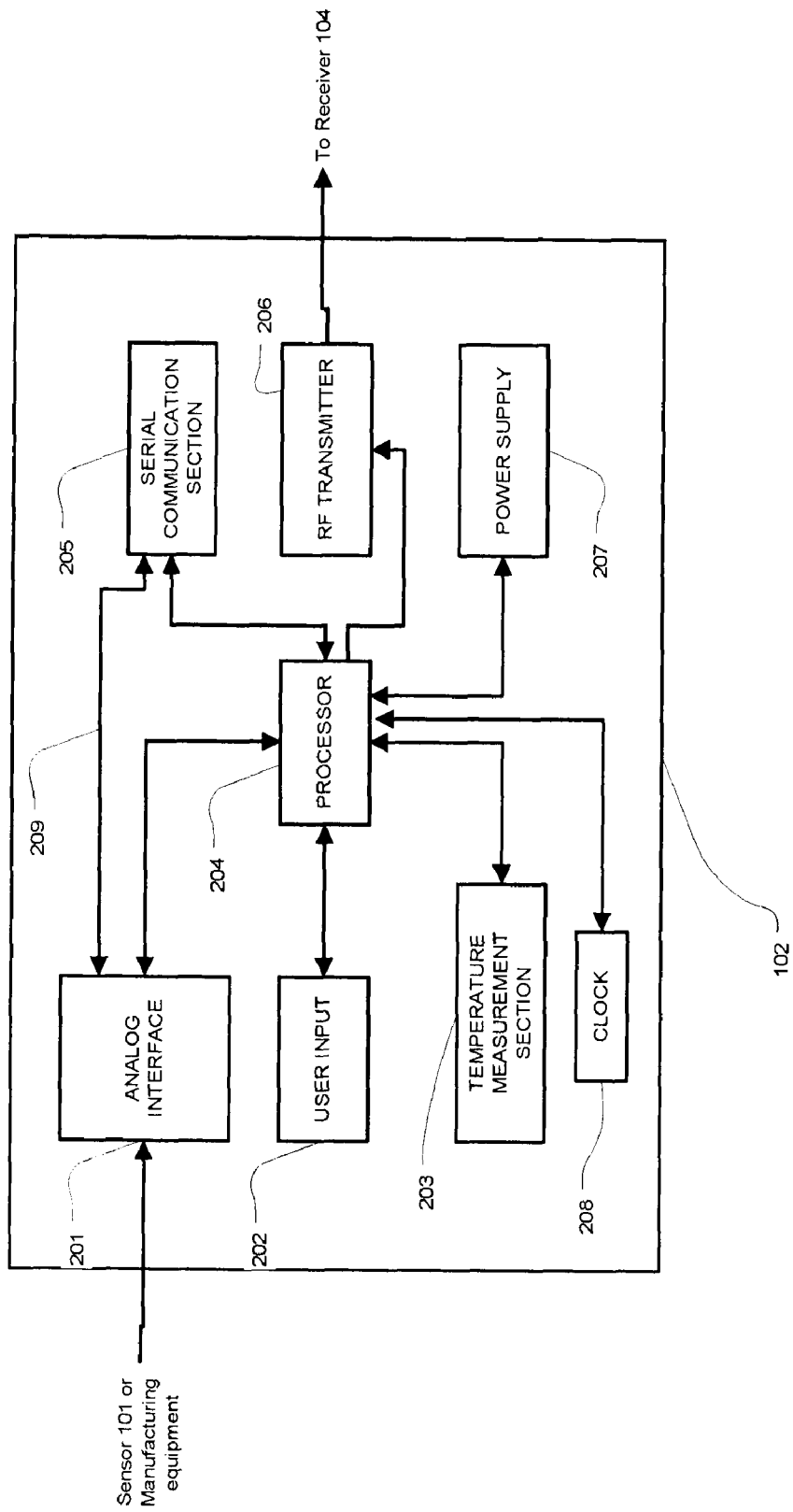
FIG. 2 is a block diagram of the transmitter unit of the data monitoring and management system shown in FIG. 1 in accordance with one embodiment of the present invention.

FIG. 2 is a block diagram of the transmitter of the data monitoring and detection system shown in FIG. 1 in accordance with one embodiment of the present invention. Referring to the Figure, the transmitter unit 102 in one embodiment includes an analog interface 201 configured to communicate with the sensor unit 101 (FIG. 1), a user input 202, and a temperature measurement section 203, each of which is operatively coupled to a transmitter processor 204 such as a central processing unit (CPU). As can be seen from FIG. 2, there are provided four contacts, three of which are electrodes—work electrode (W) 210, guard contact (G) 211, reference electrode (R) 212, and counter electrode (C) 213, each operatively coupled to the analog interface 201 of the transmitter unit 102 for connection to the sensor unit 101 (FIG. 1). In one embodiment, each of the work electrode (W) 210, guard contact (G) 211, reference electrode (R) 212, and counter electrode (C) 213 may be made using a conductive material that is either printed or etched or ablated, for example, such as carbon which may be printed, or a metal such as a metal foil (e.g., gold) or the like, which may be etched or ablated or otherwise processed to provide one or more electrodes. Fewer or greater electrodes and/or contact may be provided in certain embodiments.

Further shown in FIG. 2 are a transmitter serial communication section 205 and an RF transmitter 206, each of which is also operatively coupled to the transmitter processor 204. Moreover, a power supply 207 such as a battery is also provided in the transmitter unit 102 to provide the necessary power for the transmitter unit 102. Additionally, as can be seen from the Figure, clock 208 is provided to, among others, supply real time information to the transmitter processor 204.

In one embodiment, a unidirectional input path is established from the sensor unit 101 (FIG. 1) and/or manufacturing and testing equipment to the analog interface 201 of the transmitter unit 102, while a unidirectional output is established from the output of the RF transmitter 206 of the transmitter unit 102 for transmission to the primary receiver unit 104. In this manner, a data path is shown in FIG. 2 between the aforementioned unidirectional input and output via a dedicated link 209 from the analog interface 201 to serial communication section 205, thereafter to the processor 204, and then to the RF transmitter 206. As such, in one embodiment, via the data path described above, the transmitter unit 102 is configured to transmit to the primary receiver unit 104 (FIG. 1), via the communication link 103 (FIG. 1), processed and encoded data signals received from the sensor unit 101 (FIG. 1). Additionally, the unidirectional communication data path between the analog interface 201 and the RF transmitter 206 discussed above allows for the configuration of the transmitter unit 102 for operation upon completion of the manufacturing process as well as for direct communication for diagnostic and testing purposes.

As discussed above, the transmitter processor 204 is configured to transmit control signals to the various sections of the transmitter unit 102 during the operation of the transmitter unit 102. In one embodiment, the transmitter processor 204 also includes a memory (not shown) for storing data such as the identification information for the transmitter unit 102, as well as the data signals received from the sensor unit 101. The stored information may be retrieved and processed for transmission to the primary receiver unit 104 under the control of the transmitter processor 204. Furthermore, the power supply 207 may include a commercially available battery, which may be a rechargeable battery.

In certain embodiments, the transmitter unit 102 is also configured such that the power supply section 207 is capable of providing power to the transmitter for a minimum of about three months of continuous operation, e.g., after having been stored for about eighteen months such as stored in a low-power (non-operating) mode. In one embodiment, this may be achieved by the transmitter processor 204 operating in low power modes in the non-operating state, for example, drawing no more than approximately 1 µA of current. Indeed, in one embodiment, a step during the manufacturing process of the transmitter unit 102 may place the transmitter unit 102 in the lower power, non-operating state (i.e., post-manufacture sleep mode). In this manner, the shelf life of the transmitter unit 102 may be significantly improved. Moreover, as shown in FIG. 2, while the power supply unit 207 is shown as coupled to the processor 204, and as such, the processor 204 is configured to provide control of the power supply unit 207, it should be noted that within the scope of the present invention, the power supply unit 207 is configured to provide the necessary power to each of the components of the transmitter unit 102 shown in FIG. 2.

Referring back to FIG. 2, the power supply section 207 of the transmitter unit 102 in one embodiment may include a rechargeable battery unit that may be recharged by a separate power supply recharging unit (for example, provided in the receiver unit 104) so that the transmitter unit 102 may be powered for a longer period of usage time. Moreover, in one embodiment, the transmitter unit 102 may be configured without a battery in the power supply section 207, in which case the transmitter unit 102 may be configured to receive power from an external power supply source (for example, a battery) as discussed in further detail below.

Referring yet again to FIG. 2, the temperature measurement section 203 of the transmitter unit 102 is configured to monitor the temperature of the skin near the sensor insertion site. The temperature reading is used to adjust the analyte readings obtained from the analog interface 201. In certain embodiments, the RF transmitter 206 of the transmitter unit 102 may be configured for operation in the frequency band of 315 MHz to 322 MHz, for example, in the United States. Further, in one embodiment, the RF transmitter 206 is configured to modulate the carrier frequency by performing Frequency Shift Keying and Manchester encoding. In one embodiment, the data transmission rate is about 19,200 symbols per second, with a minimum transmission range for communication with the primary receiver unit 104.

Referring yet again to FIG. 2, also shown is a leak detection circuit 214 coupled to the guard electrode (G) 211 and the processor 204 in the transmitter unit 102 of the data monitoring and management system 100. The leak detection circuit 214 in accordance with one embodiment of the present invention may be configured to detect leakage current in the sensor unit 101 to determine whether the measured sensor data are corrupt or whether the measured data from the sensor 101 is accurate.

Description of sensor, calibration, (single point), and/or exemplary analyte systems that may be employed are described in, for example, U.S. Pat. Nos. 6,134,461, 6,175, 752, 6,121,611, 6,560,471, 6,746,582, and elsewhere.

Figure 3:
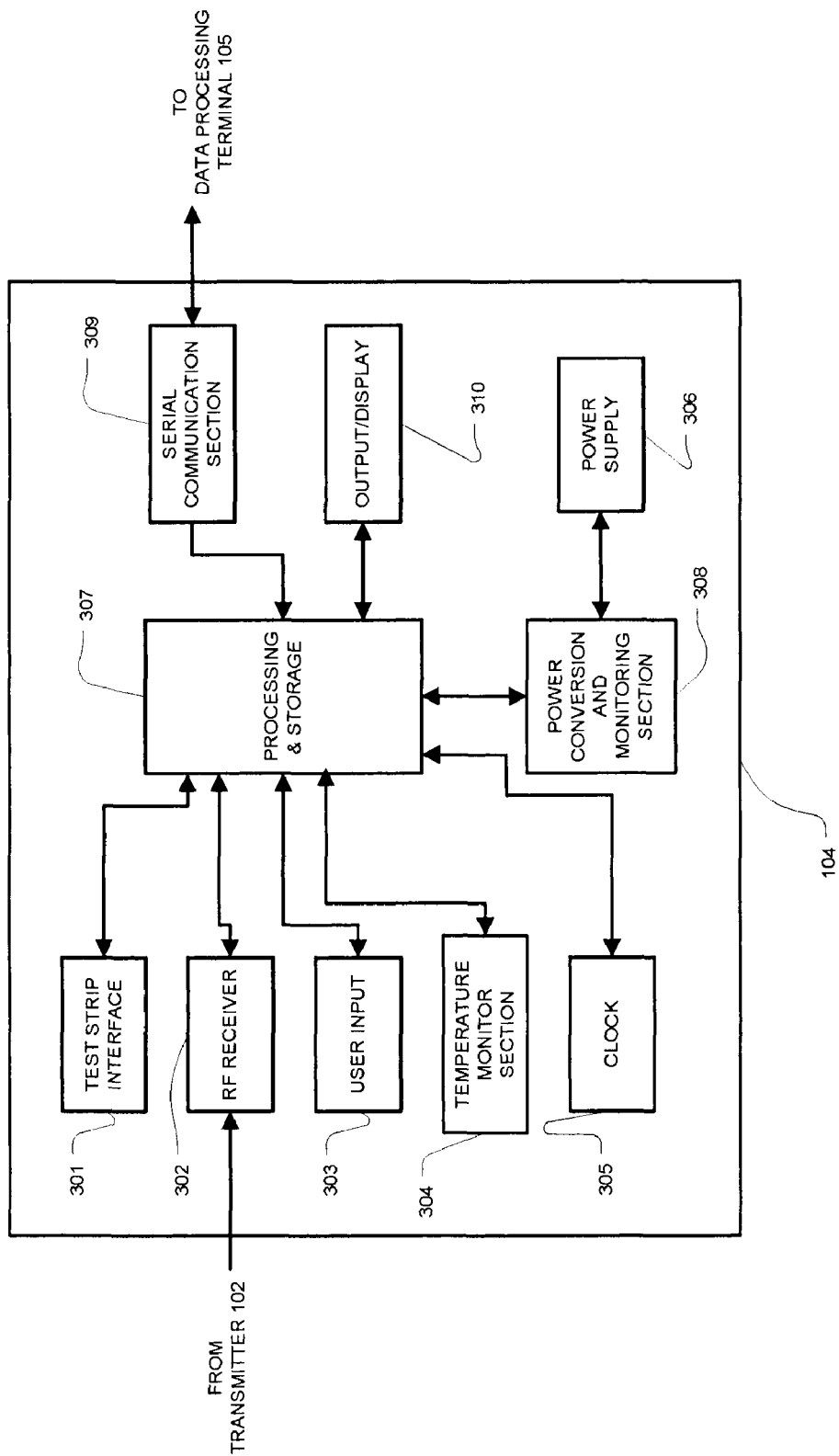
FIG. 3 is a block diagram of the receiver/monitor unit of the data monitoring and management system shown in FIG. 1 in accordance with one embodiment of the present invention.

FIG. 3 is a block diagram of the receiver/monitor unit of the data monitoring and management system shown in FIG. 1 in accordance with one embodiment of the present invention. Referring to FIG. 3, the primary receiver unit 104 includes an analyte test strip, e.g., blood glucose test strip, interface 301, an RF receiver 302, an input 303, a temperature monitor section 304, and a clock 305, each of which is operatively coupled to a receiver processor 307. As can be further seen from the Figure, the primary receiver unit 104 also includes a power supply 306 operatively coupled to a power conversion and monitoring section 308. Further, the power conversion and monitoring section 308 is also coupled to the receiver processor 307. Moreover, also shown are a receiver serial communication section 309, and an output 310, each operatively coupled to the receiver processor 307.

In one embodiment, the test strip interface 301 includes a glucose level testing portion to receive a manual insertion of a glucose test strip, and thereby determine and display the glucose level of the test strip on the output 310 of the primary receiver unit 104. This manual testing of glucose may be used to calibrate the sensor unit 101 (FIG. 1) or otherwise. The RF receiver 302 is configured to communicate, via the communication link 103 (FIG. 1) with the RF transmitter 206 of the transmitter unit 102, to receive encoded data signals from the transmitter unit 102 for, among others, signal mixing, demodulation, and other data processing. The input 303 of the primary receiver unit 104 is configured to allow the user to enter information into the primary receiver unit 104 as needed. In one aspect, the input 303 may include one or more keys of a keypad, a touch-sensitive screen, or a voice-activated input command unit. The temperature monitor section 304 is configured to provide temperature information of the primary receiver unit 104 to the receiver processor 307, while the clock 305 provides, among others, real time information to the receiver processor 307.

Each of the various components of the primary receiver unit 104 shown in FIG. 3 is powered by the power supply 306 which, in one embodiment, includes a battery. Furthermore, the power conversion and monitoring section 308 is configured to monitor the power usage by the various components in the primary receiver unit 104 for effective power management and to alert the user, for example, in the event of power usage which renders the primary receiver unit 104 in sub-optimal operating conditions. An example of such sub-optimal operating condition may include, for example, operating the vibration output mode (as discussed below) for a period of time thus substantially draining the power supply 306 while the processor 307 (thus, the primary receiver unit 104) is turned on. Moreover, the power conversion and monitoring section 308 may additionally be configured to include a reverse polarity protection circuit such as a field effect transistor (FET) configured as a battery activated switch.

The serial communication section 309 in the primary receiver unit 104 is configured to provide a bi-directional communication path from the testing and/or manufacturing equipment for, among others, initialization, testing, and configuration of the primary receiver unit 104. Serial communication section 309 can also be used to upload data to a computer, such as time-stamped blood glucose data. The communication link with an external device (not shown) can be made, for example, by cable, infrared (IR) or RF link. The output 310 of the primary receiver unit 104 is configured to provide, among others, a graphical user interface (GUI) such as a liquid crystal display (LCD) for displaying information. Additionally, the output 310 may also include an integrated speaker for outputting audible signals as well as to provide vibration output as commonly found in handheld electronic devices, such as mobile telephones presently available. In a further embodiment, the primary receiver unit 104 also includes an electro-luminescent lamp configured to provide backlighting to the output 310 for output visual display in dark ambient surroundings.

Referring back to FIG. 3, the primary receiver unit 104 in one embodiment may also include a storage section such as a programmable, non-volatile memory device as part of the processor 307, or provided separately in the primary receiver unit 104, operatively coupled to the processor 307. The processor 307 may be configured to synchronize with a transmitter, e.g., using Manchester decoding or the like, as well as error detection and correction upon the encoded data signals received from the transmitter unit 102 via the communication link 103.

Additional description of the RF communication between the transmitter 102 and the primary receiver 104 (or with the secondary receiver 106) that may be employed in embodiments of the subject invention is disclosed in pending application Ser. No. 11/060,365 filed Feb. 16, 2005 entitled "Method and System for Providing Data Communication in Continuous Glucose Monitoring and Management System" the disclosure of which is incorporated herein by reference for all purposes.

Referring to the Figures, in one embodiment, the transmitter 102 (FIG. 1) may be configured to generate data packets for periodic transmission to one ore more of the receiver units 104, 106, where each data packet includes in one embodiment two categories of data—urgent data and non-urgent data. For example, urgent data such as for example glucose data from the sensor and/or temperature data associated with the sensor may be packed in each data packet in addition to non-urgent data, where the non-urgent data is rolled or varied with each data packet transmission.

That is, the non-urgent data is transmitted at a timed interval so as to maintain the integrity of the analyte monitoring system without being transmitted over the RF communication link with each data transmission packet from the transmitter 102. In this manner, the non-urgent data, for example that are not time sensitive, may be periodically transmitted (and not with each data packet transmission) or broken up into predetermined number of segments and sent or transmitted over multiple packets, while the urgent data is transmitted substantially in its entirety with each data transmission.

Referring again to the Figures, upon receiving the data packets from the transmitter 102, the one or more receiver units 104, 106 may be configured to parse the received the data packet to separate the urgent data from the non-urgent data, and also, may be configured to store the urgent data and the non-urgent data, e.g., in a hierarchical manner. In accordance with the particular configuration of the data packet or the data transmission protocol, more or less data may be transmitted as part of the urgent data, or the non-urgent rolling data. That is, within the scope of the present disclosure, the specific data packet implementation such as the number of bits per packet, and the like, may vary based on, among others, the communication protocol, data transmission time window, and so on.

In an exemplary embodiment, different types of data packets may be identified accordingly. For example, identification in certain exemplary embodiments may include—(1) single sensor, one minute of data, (2) two or multiple sensors, (3) dual sensor, alternate one minute data, and (4) response packet. For single sensor one minute data packet, in one embodiment, the transmitter 102 may be configured to generate the data packet in the manner, or similar to the manner, shown in Table 1 below.

TABLE 1

Single sensor, one minute of data

| Number of Bits | Data Field |
|---|---|
| 8 | Transmit Time |
| 14 | Sensor1 Current Data |
| 14 | Sensor1 Historic Data |
| 8 | Transmit Status |
| 12 | AUX Counter |
| 12 | AUX Thermistor 1 |
| 12 | AUX Thermistor 2 |
| 8 | Rolling-Data-1 |

As shown in Table 1 above, the transmitter data packet in one embodiment may include 8 bits of transmit time data, 14 bits of current sensor data, 14 bits of preceding sensor data, 8 bits of transmitter status data, 12 bits of auxiliary counter data, 12 bits of auxiliary thermistor 1 data, 12 bits of auxiliary thermistor 1 data and 8 bits of rolling data. In one embodiment of the present invention, the data packet generated by the transmitter for transmission over the RF communication link may include all or some of the data shown above in Table 1.

Referring back, the 14 bits of the current sensor data provides the real time or current sensor data associated with the detected analyte level, while the 14 bits of the sensor historic or preceding sensor data includes the sensor data associated with the detected analyte level one minute ago. In this manner, in the case where the receiver unit 104, 106 drops or fails to successfully receive the data packet from the transmitter 102 in the minute by minute transmission, the receiver unit 104, 106 may be able to capture the sensor data of a prior minute transmission from a subsequent minute transmission.

Referring again to Table 1, the Auxiliary data in one embodiment may include one or more of the patient's skin temperature data, a temperature gradient data, reference data, and counter electrode voltage. The transmitter status field may include status data that is configured to indicate corrupt data for the current transmission (for example, if shown as BAD status (as opposed to GOOD status which indicates that the data in the current transmission is not corrupt)). Furthermore, the rolling data field is configured to include the non-urgent data, and in one embodiment, may be associated with the time-hop sequence number. In addition, the Transmitter Time field in one embodiment includes a protocol value that is configured to start at zero and is incremented by one with each data packet. In one aspect, the transmitter time data may be used to synchronize the data transmission window with the receiver unit 104, 106, and also, provide an index for the Rolling data field.

In a further embodiment, the transmitter data packet may be configured to provide or transmit analyte sensor data from two or more independent analyte sensors. The sensors may relate to the same or different analyte or property. In such a case, the data packet from the transmitter 102 may be configured to include 14 bits of the current sensor data from both sensors in the embodiment in which 2 sensors are employed. In this case, the data packet does not include the immediately preceding sensor data in the current data packet transmission. Instead, a second analyte sensor data is transmitted with a first analyte sensor data.

TABLE 2

Dual sensor data

| Number of Bits | Data Field |
|---|---|
| 8 | Transmit Time |
| 14 | Sensor1 Current Data |
| 14 | Sensor2 Current Data |
| 8 | Transmit Status |
| 12 | AUX Counter |
| 12 | AUX Thermistor 1 |
| 12 | AUX Thermistor 2 |
| 8 | Rolling-Data-1 |

In a further embodiment, the transmitter data packet may be alternated with each transmission between two analyte sensors, for example, alternating between the data packet shown in Table 3 and Table 4 below.

TABLE 3

Sensor Data Packet Alternate 1

| Number of Bits | Data Field |
|---|---|
| 8 | Transmitter Time |
| 14 | Sensor1 Current Data |
| 14 | Sensor1 Historic Data |
| 8 | Transmit Status |
| 12 | AUX Counter |
| 12 | AUX Thermistor 1 |
| 12 | AUX Thermistor 2 |
| 8 | Rolling-Data-1 |

TABLE 4

Sensor Data Packet Alternate 2

| Number of Bits | Data Field |
|---|---|
| 8 | Transmitter Time |
| 14 | Sensor1 Current Data |
| 14 | Sensor2 Current Data |
| 8 | Transmit Status |
| 12 | AUX Counter |
| 12 | AUX Thermistor 1 |
| 12 | AUX Thermistor 2 |
| 8 | Rolling-Data-1 |

As shown above in reference to Tables 3 and 4, the minute by minute data packet transmission from the transmitter 102 (FIG. 1) in one embodiment may alternate between the data packet shown in Table 3 and the data packet shown in Table 4. More specifically, the transmitter 102 may be configured in one embodiment transmit the current sensor data of the first sensor and the preceding sensor data of the first sensor (Table 3), as well as the rolling data, and further, at the subsequent transmission, the transmitter 102 may be configured to transmit the current sensor data of the first and the second sensor in addition to the rolling data.

In one embodiment, the rolling data transmitted with each data packet may include a sequence of various predetermined types of data that are considered not-urgent or not time sensitive. That is, in one embodiment, the following list of data shown in Table 6 may be sequentially included in the 8 bits of transmitter data packet, and not transmitted with each data packet transmission of the transmitter (for example, with each 60 second data transmission from the transmitter 102).

TABLE 6

Rolling Data

| Time Slot | Bits | Rolling-Data |
| --- | --- | --- |
| 0 | 8 | Mode |
| 1 | 8 | Glucose1 Slope |
| 2 | 8 | Glucose2 Slope |
| 3 | 8 | Ref-R |
| 4 | 8 | Hobbs Counter, Ref-R |
| 5 | 8 | Hobbs Counter |
| 6 | 8 | Hobbs Counter |
| 7 | 8 | Sensor Count |

As can be seen from Table 6 above, in one embodiment, a sequence of rolling data are appended or added to the transmitter data packet with each data transmission time slot. In one embodiment, there may be 256 time slots for data transmission by the transmitter 102 (FIG. 1), and where, each time slot is separately by approximately 60 second interval. For example, referring to the Table 6 above, the data packet in transmission time slot 0 (zero) may include operational mode data (Mode) as the rolling data that is appended to the transmitted data packet. At the subsequent data transmission time slot (for example, approximately 60 seconds after the initial time slot (0), the transmitted data packet may include the analyte sensor 1 calibration factor information (Glucose1 slope) as the rolling data. In this manner, with each data transmission, the rolling data may be updated over the 256 time slot cycle.

Referring again to Table 6, each rolling data field is described in further detail for various embodiments. For example, the Mode data may include information related to the different operating modes such as, but not limited to, the data packet type, the type of battery used, diagnostic routines, single sensor or multiple sensor input, type of data transmission (rf communication link or other data link such as serial connection). Further, the Glucose1-slope data may include an 8-bit scaling factor or calibration data for first sensor (scaling factor for sensor 1 data), while Glucose2-slope data may include an 8-bit scaling factor or calibration data for the second analyte sensor (in the embodiment including more than one analyte sensors).

In addition, the Ref-R data may include 12 bits of on-board reference resistor used to calibrate our temperature measurement in the thermistor circuit (where 8 bits are transmitted in time slot 3, and the remaining 4 bits are transmitted in time slot 4), and the 20-bit Hobbs counter data may be separately transmitted in three time slots (for example, in time slot 4, time slot 5 and time slot 6) to add up to 20 bits. In one embodiment, the Hobbs counter may be configured to count each occurrence of the data transmission (for example, a packet transmission at approximately 60 second intervals) and may be incremented by a count of one (1).

In one aspect, the Hobbs counter is stored in a nonvolatile memory of the transmitter unit 102 (FIG. 1) and may be used to ascertain the power supply status information such as, for example, the estimated battery life remaining in the transmitter unit 102. That is, with each sensor replacement, the Hobbs counter is not reset, but rather, continues the count with each replacement of the sensor unit 101 to establish contact with the transmitter unit 102 such that, over an extended usage time period of the transmitter unit 102, it may be possible to determine, based on the Hobbs count information, the amount of consumed battery life in the transmitter unit 102, and also, an estimated remaining life of the battery in the transmitter unit 102.

Figure 4:
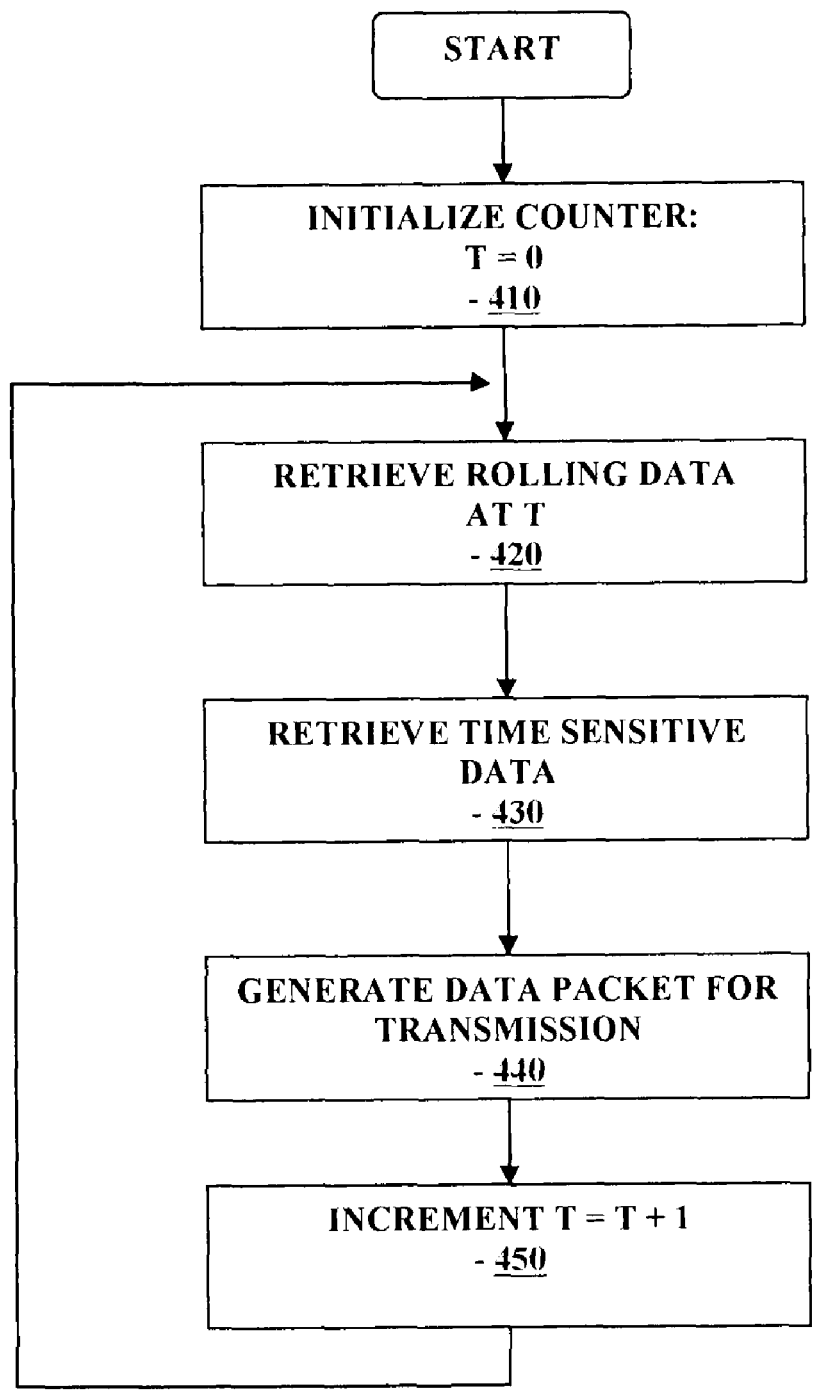
FIG. 4 is a flowchart illustrating data packet procedure including rolling data for transmission in accordance with one embodiment of the present invention.

FIG. 4 is a flowchart illustrating a data packet procedure including rolling data for transmission in accordance with one embodiment of the present invention. Referring to FIG. 4, in one embodiment, a counter is initialized (for example, to T=0) (410). Thereafter the associated rolling data is retrieved from memory device, for example (420), and also, the time sensitive or urgent data is retrieved (430). In one embodiment, the retrieval of the rolling data (420) and the retrieval of the time sensitive data (430) may be retrieved at substantially the same time.

Referring back to FIG. 4, with the rolling data and the time sensitive data, for example, the data packet for transmission is generated (440), an upon transmission, the counter is incremented by one (430) and the routine returns to retrieval of the rolling data (420). In this manner, in one embodiment, the urgent time sensitive data as well as the non-urgent data may be incorporated in the same data packet and transmitted by the transmitter 102 (FIG. 1) to a remote device such as one or more of the receivers 104, 106. Furthermore, as discussed above, the rolling data may be updated at a predetermined time interval which is longer than the time interval for each data packet transmission from the transmitter 102 (FIG. 1).

Figure 5:
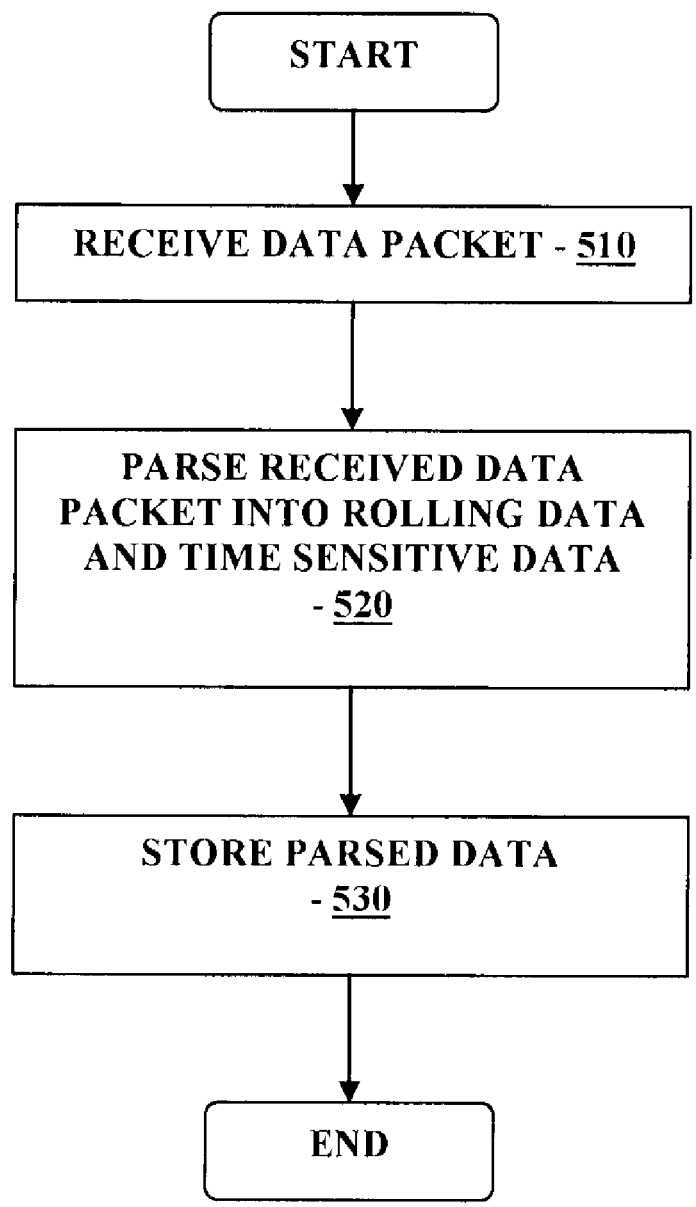
FIG. 5 is a flowchart illustrating data processing of the received data packet including the rolling data in accordance with one embodiment of the present invention.

FIG. 5 is a flowchart illustrating data processing of the received data packet including the rolling data in accordance with one embodiment of the present invention. Referring to FIG. 5, when the data packet is received (510) (for example, by one or more of the receivers 104, 106, in one embodiment, the received data packet is parsed so that the urgent data may be separated from the not-urgent data (520) (stored in, for example, the rolling data field in the data packet). Thereafter the parsed data is suitably stored in an appropriate memory or storage device (530).

In the manner described above, in accordance with one embodiment of the present invention, there is provided method and apparatus for separating non-urgent type data (for example, data associated with calibration) from urgent type data (for example, monitored analyte related data) to be transmitted over the communication link to minimize the potential burden or constraint on the available transmission time. More specifically, in one embodiment, non-urgent data may be separated from data that is required by the communication system to be transmitted immediately, and transmitted over the communication link together while maintaining a minimum transmission time window. In one embodiment, the non-urgent data may be parsed or broken up in to a number of data segments, and transmitted over multiple data packets. The time sensitive immediate data (for example, the analyte sensor data, temperature data etc), may be transmitted over the communication link substantially in its entirety with each data packet or transmission.

Accordingly, in one embodiment, there is provided a method including retrieving a first data type, retrieving a second data type, transmitting a first data packet including the first data type and the second data type, updating the second data type, and generating a second data packet including the first data type and the updated second data type.

In one aspect, the first data type may be associated with urgent data, and further, where the second data type may be associated with non-urgent data.

In another aspect, the first data type may include real time analyte data associated with the monitored analyte level of a patient, and further, where the analyte may include glucose. Moreover, in one aspect, the first data type may be related to glucose level information, and the second data type may be related to a predetermined scaling factor associated with the glucose level information.

In still another aspect, the second data type may include one or more of a component status information, a calibration data, or an analyte sensor count information.

Moreover, the second data type and the updated second data type may be different.

The method may also include encrypting the first data packet before transmission. Moreover, the method may also include encrypting the second data packet.

Furthermore, in still another aspect, the method may include transmitting the encrypted second data packet, where the first data packet transmission and the second data packet transmission may be separated by one of approximately 60 seconds, less than five minutes, five minutes, or greater than five minutes.

Additionally, each of the first and second data packets may include a transmit time count which is incremented by an integer value with each subsequent transmission.

A method in accordance with another embodiment may include receiving a data packet, parsing the received data packet such that a first data type and a second data type are retrieved from the received data packet, and wherein the first data type is urgent type data, and the second data type is non-urgent type data.

The urgent type data in one embodiment may include analyte sensor data, and further, where the analyte may include glucose. Moreover, in one aspect, the first data type may be related to glucose level information, and the second data type may be related to a predetermined scaling factor associated with the glucose level information. The method may further include storing the first data type and the second data type.

An apparatus in accordance with another embodiment of the present invention includes one or more processing units, and a memory for storing instructions which, when executed by the one or more processors, causes the one or more processing units to retrieve a first data type, retrieve a second data type, transmit a first data packet including the first data type and the second data type, update the second data type, and generate a second data packet including the first data type and the updated second data type.

In another aspect, the apparatus may also include an rf transmitter coupled to he one or more processing units, and configured to transmit the first data packet, and the second data packet.

In still another aspect, the apparatus may include a medical module operatively coupled to the one or more processing units and the memory.

The medical module may include a continuous glucose monitoring device.

Furthermore, there may be provided a housing, where the medical module, the one or more processing units and the memory are integrated substantially within the housing.

The various processes described above including the processes performed by the processor 204 in the software application execution environment in the transmitter 102 as well as any other suitable or similar processing units embodied in the analyte monitoring system 100 including the processes and routines described in conjunction with FIGS. 4-5, may be embodied as computer programs developed using an object oriented language that allows the modeling of complex systems with modular objects to create abstractions that are representative of real world, physical objects and their interrelationships. The software required to carry out the inventive process, which may be stored in a memory or storage unit (not shown) of the processor 204 or the transmitter 102, may be developed by a person of ordinary skill in the art and may include one or more computer program products.

Various other modifications and alterations in the structure and method of operation of this invention will be apparent to those skilled in the art without departing from the scope and spirit of the invention. Although the invention has been described in connection with specific preferred embodiments, it should be understood that the invention as claimed should not be unduly limited to such specific embodiments. It is intended that the following claims define the scope of the present invention and that structures and methods within the scope of these claims and their equivalents be covered thereby.

What is claimed is:

1. A computer implemented method for communicating rolling data in an analyte monitoring system, comprising:
retrieving with a processor a first data type from a storage device, wherein the first data type includes analyte sensor data obtained from an analyte sensor positioned in fluid contact with an interstitial fluid under a skin of a user;
retrieving with the processor a predetermined portion of the rolling data from the storage device, the rolling data comprising a plurality of parameters, wherein each predetermined portion of the rolling data is assigned a transmission time slot and includes at least one of the following parameters: operational mode data, analyte sensor slope data, reference resistor data for temperature measurement, power supply status data, analyte sensor calibration data, data transmission count data, or analyte sensor scaling factor data;
transmitting during a first transmission time slot a first data packet including the first data type and the predetermined portion of the rolling data assigned to the first transmission time slot to a remote location;
generating with the processor a second data packet including the first data type and the predetermined portion of the rolling data assigned to a second transmission time slot for transmission to the remote location; and
transmitting during the second transmission time slot the second data packet to the remote location subsequent to the first data packet transmission;
wherein each transmitted data packet comprises the first data type and the predetermined portion of the rolling data.

2. The method of claim 1 wherein the first data type is associated with urgent data, and further, wherein the rolling data is associated with non-urgent data.

3. The method of claim 1 wherein the analyte data includes real time analyte data associated with the monitored analyte level of a patient.

4. The method of claim 3 wherein the analyte includes glucose, and further, wherein the first data type is related to glucose level information, and the rolling data is related to a predetermined scaling factor associated with the glucose level information.

5. The method of claim 1 further including encrypting the first data packet before transmission.

6. The method of claim 1 further including encrypting the second data packet.

7. The method of claim 6 wherein transmitting the second data packet includes transmitting the encrypted second data packet.

8. The method of claim 1 wherein each of the first and second data packets include a transmit time count which is incremented by an integer value with each subsequent transmission.

9. The method of claim 1 wherein the first data packet transmission and the second data packet transmission are separated by one of approximately 60 seconds, less than approximately five minutes, approximately five minutes, or greater than approximately five minutes.

10. The method of claim 1 wherein the first data type includes current sensor data and historic sensor data.

11. The method of claim 10 wherein the first data type in the first data packet is current sensor data and the first data type in the second data packet is historic sensor data.

12. The method of claim 11 wherein the historic sensor data includes sensor data that immediately precedes the current sensor data.

13. A computer implemented method for communicating rolling data in an analyte monitoring system, comprising:
  receiving using a processor a first data packet over a data communication channel during a first time slot;
  parsing using the processor the received first data packet such that a first data type and a predetermined portion of the rolling data assigned to the first time slot are retrieved from the received first data packet;
  receiving using the processor a second data packet over the data communication channel during a second time slot; and
  parsing using the processor the received second data packet such that the first data type and the predetermined portion of the rolling data assigned to the second time slot are retrieved from the received second data packet;
    wherein the first data type is urgent type data, and the rolling data is non-urgent type data, wherein the rolling data comprises a plurality of parameters, wherein each predetermined portion of the rolling data is assigned a time slot and includes at least one of the following parameters:
  operational mode data, analyte sensor slope data, reference resistor data for temperature measurement, power supply status data, analyte sensor calibration data, data transmission count data, or analyte sensor scaling factor data, wherein each received data packet comprises the first data type and the predetermined portion of the rolling data, wherein the urgent type data includes analyte sensor data obtained form an analyte sensor positioned in fluid contact with an interstitial fluid under a skin of a user.

14. The method of claim 12 wherein the analyte includes glucose, and wherein the urgent type data includes glucose data related to a monitored glucose level of the patient.

15. The method of claim 13 further including storing the first data type and the rolling data.

16. The method of claim 13 wherein the rolling data includes a counter value associated with a power supply status, and further, wherein the counter value is incremented with each replacement of an analyte sensor.

17. The method of claim 16 wherein the power supply status includes an estimated battery life information.

18. An apparatus for communicating rolling data in an analyte monitoring system, comprising:
  one or more processing units;
  one or more analyte sensors in signal communication with the one or more processing units and positioned in fluid contact with an interstitial fluid under a skin layer of a patient, the one or more analyte sensors generating analyte data related to a monitored analyte level of the user; and
  a memory for storing instructions which, when executed by the one or more processing units, causes the one or more processing units to:
  retrieve a first data type, wherein the first data type includes the analyte data;
  retrieve a predetermined portion of the rolling data, the rolling data comprising a plurality of parameters, wherein each predetermined portion of the rolling data is assigned a transmission time slot;
  transmit during a first transmission time slot a first data packet including the first data type and the predetermined portion of the rolling data assigned to the first transmission time slot;
  generate a second data packet including the first data type and the predetermined portion of the rolling data assigned to the second transmission time slot; and
  transmit during the second transmission time slot the second data packet subsequent to the first data packet transmission;
  wherein each predetermined portion of the rolling data assigned to a transmission time slot includes at least one of the following parameters: operational mode data, analyte sensor slope data, reference resistor data for temperature measurement, power supply status information, analyte sensor calibration data, data transmission count information, and analyte sensor scaling factor data; and
  wherein the memory for storing instructions which, when executed by the one or more processing units, causes the one or more processing units to increment a counter value indicative of a power supply status of the apparatus.

19. The apparatus of claim 18 wherein the analyte data includes real time analyte data associated with the monitored analyte level of the user.

20. The apparatus of claim 19 wherein the analyte includes glucose.

21. The apparatus of claim 18 further including an rf transmitter coupled to the one or more processing units, and configured to transmit the first data packet, and the second data packet.

22. The apparatus of claim 18 further including a medical module operatively coupled to the one or more processing units and the memory.

23. The apparatus of claim 22 wherein the medical module includes a continuous glucose monitoring device.

24. The apparatus of claim 22 further including a housing, wherein the medical module, the one or more processing units and the memory are integrated substantially within the housing.

25. The apparatus of claim 18 wherein the power supply status of the apparatus includes estimated battery life remaining in the apparatus.

26. The apparatus of claim 18 further comprising one or more analyte sensors coupled thereto, wherein the counter value is not reset with each analyte sensor replacement, and wherein the one or more processing units are in signal communication with each analyte sensor positioned in fluid contact with the interstitial fluid under the skin layer of the patient.

27. The apparatus of claim 26 wherein the one or more analyte sensors includes a glucose sensor.

28. A computer implemented method for communicating data packets in an analyte monitoring system, comprising:
  receiving with a processor signals from an analyte sensor in fluid contact with an interstitial fluid under a skin layer for monitoring an analyte level in the fluid of a patient;

generating with the processor a plurality of data packets, each generated data packet including a first data portion corresponding to received real time analyte sensor data and a predetermined second data portion comprising a plurality of parameters, wherein each predetermined second data portion is assigned a transmission time slot and includes at least one of the following parameters:

operational mode data, analyte sensor slope data, reference resistor data for temperature measurement, power supply status data, analyte sensor calibration data, data transmission count data, and analyte sensor scaling factor data;

transmitting during a first transmission time slot a first data packet including the first data portion and the predetermined second data portion assigned to the first transmission time slot to a remote location; and transmitting during a second transmission time slot a second data packet to the remote location subsequent to the first data packet transmission;
    wherein each transmitted data packet comprises the first data portion and the predetermined second data portion.

29. The method of claim 28 wherein each data packet transmitted to the remote location includes at least one of the plurality of parameters, and further, wherein the same parameter is not included in two sequentially transmitted data packets to the remote location.

* * * * *